United States Patent
Park et al.

(10) Patent No.: US 11,542,511 B2
(45) Date of Patent: Jan. 3, 2023

(54) RECOMBINANT MICROORGANISM HAVING SIMULTANEOUS FERMENTATION ABILITY OF AT LEAST TWO SUGARS AND METHOD FOR PRODUCING DIOL USING SAME

(71) Applicant: GS CALTEX CORPORATION, Seoul (KR)

(72) Inventors: Jong-Myoung Park, Sejong (KR); Chelladurai Rathnasingh, Daejeon (KR); Hyo-Hak Song, Daejeon (KR)

(73) Assignee: GS CALTEX CORPORATION, Seoul (KR)

( * ) Notice: Subject to any disclaimer, the term of this patent is extended or adjusted under 35 U.S.C. 154(b) by 0 days.

(21) Appl. No.: 16/768,786

(22) PCT Filed: Nov. 30, 2018

(86) PCT No.: PCT/KR2018/015036
§ 371 (c)(1),
(2) Date: Jun. 1, 2020

(87) PCT Pub. No.: WO2019/108000
PCT Pub. Date: Jun. 6, 2019

(65) Prior Publication Data
US 2021/0171960 A1    Jun. 10, 2021

(30) Foreign Application Priority Data
Dec. 1, 2017    (KR) .................. 10-2017-0164591

(51) Int. Cl.
| | | |
|---|---|---|
| *C12N 15/74* | (2006.01) | |
| *C07K 14/26* | (2006.01) | |
| *C12N 9/10* | (2006.01) | |
| *C12N 9/12* | (2006.01) | |
| *C12N 9/90* | (2006.01) | |
| *C12N 9/92* | (2006.01) | |
| *C12P 7/18* | (2006.01) | |

(52) U.S. Cl.
CPC .............. *C12N 15/74* (2013.01); *C07K 14/26* (2013.01); *C12N 9/1022* (2013.01); *C12N 9/1205* (2013.01); *C12N 9/90* (2013.01); *C12N 9/92* (2013.01); *C12P 7/18* (2013.01); *C12Y 202/01001* (2013.01); *C12Y 202/01002* (2013.01); *C12Y 207/01017* (2013.01); *C12Y 501/03001* (2013.01); *C12Y 503/01005* (2013.01); *C12Y 503/01006* (2013.01)

(58) Field of Classification Search
None
See application file for complete search history.

(56) References Cited

U.S. PATENT DOCUMENTS

| 10,266,854 B2 * | 4/2019 | Lee ..................... C12N 9/0006 |
| 2016/0281096 A1 * | 9/2016 | Park ....................... C12P 7/18 |
| 2016/0298144 A1 * | 10/2016 | Isobe ...................... C12N 1/20 |

FOREIGN PATENT DOCUMENTS

CN    101457211 A    6/2009

OTHER PUBLICATIONS

Chica et al. Curr Opin Biotechnol. Aug. 2005;16(4):378-84. (Year: 2006).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Xiao-Jun Ji et al., "Elimination of carbon catabolite repression in Klebsiella oxytoca for efficient 2,3-butanediol production from glucose-xylose mixtures", Applied Microbiology and Biotechnology, 2011, vol. 89, 1119-1125, cited in NPL No. 4.
Xiao-Jun Ji et al., "Development of an industrial medium for economical 2,3-butanediolproduction through co-fermentation of glucose and xylose by Klebsiella oxytoca", Bioresource Technology, 2009, vol. 100, 5214-5218, cited in NPL No. 4.
Rodney J. Bothast et al., "Fermentation of L-Arabinose, D-Xywse and D-Glucose by Etiianowgenic Recombinant Klebsieiia Oxytoca Strain P2", Biotechnology Letters, Apr. 1994, vol. 16, No. 4, 401-406, cited in NPL No. 4.
International Search Report dated Mar. 5, 2019 for corresponding international application No. PCT/KR2018/015036, citing above references.
Michael E. Kovach et al., "Four new derivatives of the broad-host-range cloning vector pBBR1MCS, carrying different antibiotic-resistance cassettes", Gene, 1995, vol. 166, 175-176, substitute document for the cited reference in the Specification, Kovach et al., Biotechniques, vol. 199, 800-802 (currently unavailable).

* cited by examiner

*Primary Examiner* — Christian L Fronda
(74) *Attorney, Agent, or Firm* — Hauptman Ham, LLP

(57) ABSTRACT

The present invention relates to a recombinant microorganism which is capable of simultaneously fermenting at least two sugars in a lignocellulosic saccharified liquid, and also capable of generating diol.

7 Claims, 19 Drawing Sheets
Specification includes a Sequence Listing.

RECOMBINANT MICROORGANISM HAVING SIMULTANEOUS FERMENTATION ABILITY OF AT LEAST TWO SUGARS AND METHOD FOR PRODUCING DIOL USING SAME

CROSS-REFERENCE TO RELATED APPLICATION

The present application is a national stage filing under 35 U.S.C § 371 of PCT application number PCT/KR2018/015036 filed on Nov. 30, 2018 which is based upon and claims the benefit of priorities to Korean Patent Application No. 10-2017-0164591, filed on Dec. 1, 2017, in the Korean Intellectual Property Office. The disclosures of the above-listed applications are hereby incorporated by reference herein in their entireties.

FIELD

The present disclosure relates to a recombinant microorganism having simultaneous fermentation ability of mixed sugars, and a method for producing diols using the same.

DESCRIPTION OF RELATED ART

Diol is a compound that is not only widely used in industry, but also used as a chemical intermediate of various types, and has a great usefulness. For example, 2,3-butanediol may be used as a precursor in producing 1,3-butadiene as a major raw material for synthetic rubber, and methyl ethyl ketone (MEK) as a solvent and thus is a chemical material having high industrial potential. Further, 2,3-butanediol has an exceptionally low freezing point and may be used directly as an anti-freezing agent, and has a high octane number and may be used as an octane booster in combination with conventional gasoline. Further, 1,3-propane diol may be used as a monomer for a polymer such as polyester or polyurethane. Further, 1,3-propane diol may be used as an additive for improving properties of cosmetics and personal hygiene products. In particular, in polytrimethylene terephthalate (PTT) as a linear aromatic polyester as produced via polymerization of 1,3-propanediol and terephthalic acid, an unique twist (referred to a kink) occurring on a semi-crystal molecular structure is present on a polymer chain, thereby to exhibit excellent morphological stability. Due to this structural property, the PTT may be applied to a wide variety of fields, such as textiles, packaging and films, non-woven structures, and engineering plastics.

The diols may be produced via chemical synthesis or microorganism fermentation. However, the chemical synthesis process has a problem that environmental pollutants are generated in a process or a synthesis cost is high. To the contrary, production of diol via the fermentation of microorganisms from renewable resources is environmentally friendly, but causes an increase in grain price, low strain fermentation yield, and low productivity and thus is not advantageous for industrial use.

For example, a cellulosic biomass (wood, empty fruit bunch (EFB)), and herbaceous and woody based (hereinafter collectively referred to as "lignocellulosic") biomass such as corn stalk, rice straw, etc. are non-edible biomass. Thus, when using the cellulosic biomass and the lignocellulosic biomass, diols may be produced at low cost compared to a case when using edible biomass (grains, etc.). Thus, the cellulosic biomass and the lignocellulosic biomass for diol production may be advantageously used as' an industrial biomaterial. However, the lignocellulosic-derived biomass contains a mixture of pentose and hexose. In this connection, based on a catabolite repression mechanism, microorganisms use hexose first for metabolism and then pentose for metabolism. Therefore, a sugar consumption rate is slow, so that the fermentation time increases and productivity decreases. Further, when pentose such as xylose remains in a fermentation broth, diol separation and purification becomes difficult.

Accordingly, the present inventors have studied microorganisms capable of metabolizing efficiently lignocellulosic biomass and thus have invented recombinant microorganisms having excellent simultaneous fermentation ability of pentose and hexose.

DISCLOSURE

Technical Purposes

A purpose of the present disclosure is to provide a recombinant microorganism having excellent simultaneous fermentation ability of pentose and hexose.

Another purpose of the present disclosure is to produce diols using the recombinant microorganism.

Technical Solutions

To achieve the purpose, the present disclosure provides a recombinant microorganism having simultaneous fermentation ability of at least two sugars in lignocellulosic hydrolysate, wherein recombinant microorganism has diol production ability.

Further, the present disclosure provides a method for producing a diol, the method including:

preparing a medium containing at least two sugars;

inoculating the recombinant microorganism into the medium; and culturing the recombinant microorganism in the medium.

Technical Effects

The microorganisms having simultaneous fermentation ability of mixed sugars and the method for producing diols using the same may be realized.

BRIEF DESCRIPTIONS OF DRAWINGS

FIG. 1 schematically shows hexose and pentose metabolism pathways of *Klebsiella oxytoca*.

Figure 1:
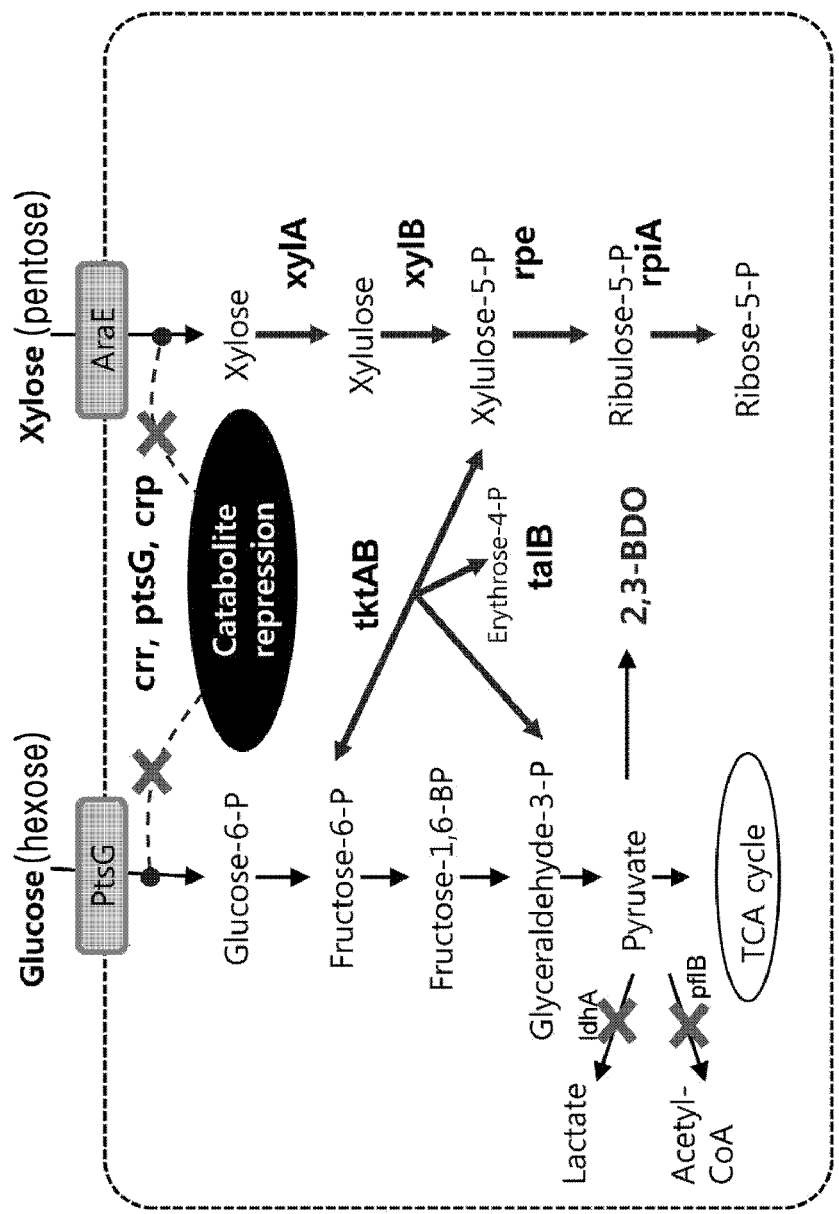

Symbols used in the figures indicate:
■: glucose
♦: xylose
●: 2,3 butanediol
▲: lactate

DETAILED DESCRIPTIONS

The present disclosure relates to
a recombinant microorganism having simultaneous fermentation ability of at least two sugars in lignocellulosic hydrolysate,
wherein recombinant microorganism has diol production ability.

Further, the present disclosure relates to a method for producing a diol, the method including:
preparing a medium comprising at least two sugars;
inoculating the recombinant microorganism into the medium; and
culturing the recombinant microorganism in the medium.

Hereinafter, the present disclosure will be described in detail.

Lignocellulosic Hydrolysate

A recombinant microorganism according to the present disclosure is resistant to lignocellulosic hydrolysate. Further, the recombinant microorganism according to the present disclosure has simultaneous fermentation ability of at least two sugars in the lignocellulosic hydrolysate. The lignocellulosic hydrolysate is a hydrolysate obtained by hydrolyzing lignocellulosic raw materials (e.g. wood, empty fruit bunch (EFB), corn stalk, sugar cane stalk, reed, *Miscanthus sinensis*, rice straw, etc.). Preferably, the lignocellulosic hydrolysate is a hydrolysate obtained by hydrolyzing the lignocellulosic raw material and then removing lignin. The lignocellulosic hydrolysate comprises mixed sugars. The mixed sugars contain at least two sugars. Preferably, the hydrolysate contains pentose such as xylose, mannose, galactose, arabinose, cellobiose, hexose such as glucose, and disaccharides. In particular, a content of each of glucose and xylose therein is high.

Lignocellulosic Hydrolysate Resistance

The recombinant microorganism according to the present disclosure is resistant to the lignocellulosic hydrolysate. The recombinant microorganism being resistant to the lignocellulosic hydrolysate may mean that the recombinant microorganism may grow in a hydrolysate-containing medium, and that growth inhibition of the microorganisms is not caused by ingredients in the hydrolysate.

Simultaneous Fermentation Ability

The recombinant microorganism according to the present disclosure has simultaneous fermentation ability of at least two sugars in the lignocellulosic hydrolysate. The simultaneous fermentation ability means that the recombinant microorganism does not ferment one sugar in a preceding manner than another sugar. The recombinant microorganisms according to the present disclosure have the simultaneous fermentation ability of at least two sugars, so that metabolism of a first sugar is prevented from being inhibited by a second sugar when the first and second sugars are subjected to simultaneous fermentation. In this connection, the phenomenon that metabolism of the first sugar is inhibited by the second sugar refers to catabolite repression. Thus, the recombinant microorganisms according to the present disclosure may have inhibited catabolite repression.

Simultaneous Fermentation Ability of Recombinant Microorganism

The recombinant microorganism according to the present disclosure has simultaneous fermentation ability of at least two sugars the in lignocellulosic hydrolysate. Preferably, the recombinant microorganism according to the present disclosure has the simultaneous fermentation ability of glucose and at least one sugar selected from a group consisting of xylose, arabinose and cellobiose. More preferably, the recombinant microorganism according to the present disclosure has a simultaneous fermentation percentage of xylose of 90% or greater, preferably, 95% or greater.

Simultaneous fermentation percentage of sugar (%)={(total input sugar amount (g)−residual sugar amount after fermentation (g))/total input sugar amount (g)}×100

Example) Simultaneous Fermentation Percentage of Xylose (%)

Simultaneous fermentation percentage of xylose={(total input xylose amount (g)−residual xylose amount after fermentation (g))/(total input xylose amount (g))}×100

Diol

The diol according to the present disclosure has 5 or smaller carbon atoms. Preferably, the diol according to the present disclosure is butanediol. More preferably, the diol according to the present disclosure is 2,3-butanediol.

Recombinant Microorganism

The present disclosure is directed to recombinant microorganisms having simultaneous fermentation ability of at least two sugars in the lignocellulosic hydrolysate, and having diol production ability. The recombinant microorganism is resistant to lignocellulosic hydrolysate. More preferably, the recombinant microorganism is resistant to a microorganism growth inhibitory substance in the lignocellulosic hydrolysate. Further, the recombinant microorganism has the simultaneous fermentation ability of hexose and pentose, and preferably has simultaneous fermentation ability of glucose and xylose.

The recombinant microorganism is preferably recombinant *Klebsiella*. More preferably, the recombinant microorganism according to the present disclosure is recombinant *Klebsiella oxytoca*.

The catabolite repression may be more inhibited in the recombinant microorganisms according to the present disclosure than in a wild-type microorganism. Preferably, a glucose-specific phosphotransferase enzyme IIA component of PTS (phosphotransferase system) or a glucose-specific phosphotransferase enzyme IIBC component of PTS may be more inhibited in the recombinant microorganism according to the present disclosure than in the wild-type microorganism.

A pathway along which xylose is converted to xylulose and then to xylulose-5-P or ribulose-5-P or ribose-5-P or fructose-6-P or erythrose-4-P or glyceraldehyde-3-P may be more activated in the recombinant microorganism according to the present disclosure than in the wild-type microorganism. Preferably, the recombinant microorganism according to the present disclosure may have enhanced activity of at least one enzyme selected from a group consisting of xylose isomerase, xylulokinase, D-ribulose-5-phosphate 3-epimerase, ribose 5-phosphate isomerase, transaldolase, and transketolase.

The recombinant microorganism according to the present disclosure has preferably inhibited activity of a cAMP receptor of a receptor protein cAMP (cyclic adenosine monophosphate). More preferably, the recombinant microorganism according to the present disclosure may have a mutation in a gene for encoding a cAMP-activated global transcription factor, so that expression of the gene is inhibited, or a mutated gene is overexpressed to inhibit the cAMP receptor activity.

In the recombinant microorganism according to the present disclosure, a pathway along which pyruvate is converted to lactate is preferably inhibited. Lactate dehydrogenase regulates the conversion of pyruvate to lactate. Inhibiting the lactate dehydrogenase may allow the pathway along which pyruvate is converted to lactate may be inhibited. The inhibition of the lactate dehydrogenase may be achieved via expression inhibition of lactate dehydrogenase, inhibition of lactate dehydrogenase enzyme activity, and the like. For example, deletion of ldhA as a gene for encoding the lactate dehydrogenase, or causing of mutation in the gene (mutation via modification, substitution or deletion of some bases of the gene or introduction of some bases to the gene to inhibit normal gene expression), or regulation of gene expression in a transcription or translation process may be appropriately selected by those skilled in the art to inhibit the lactate dehydrogenase.

Further, it is desirable that in the recombinant microorganism according to the present disclosure, a pathway along which pyruvate is converted to acetyl coenzyme A and formic acid is inhibited. Pyruvate-formate lyase catalyzes conversion of pyruvate to acetyl coenzyme A and formic acid in a facultive anaerobic condition (pathway 1).

pyruvate→acetyl coenzyme A+formic acid       <Pathway 1>

Inhibiting the pyruvate-formate lyase may allow a pathway along which pyruvate is converted to acetyl coenzyme A and a pathway along which pyruvate is converted to formic acid to be inhibited. Inhibition of the pyruvate-formate lyase may be achieved via expression inhibition of pyruvate-formate lyase, enzyme activity inhibition of pyruvate-formate lyase, and the like. For example, deleting of pflB as a gene for encoding the pyruvate-formate lyase, or causing of mutation in the gene (mutation via modification, substitution or deletion of some bases of the gene or introduction of some bases to the gene to inhibit normal gene expression), regulation of gene expression in a transcription process or a translation process may be appropriately selected by a person skilled in the art to inhibit the pyruvate-formate lyase.

FIG. 1 shows pathways that are more enhanced or inhibited in the recombinant *Klebsiella oxytoca* according to the present disclosure compared to the wild-type strain, and shows genes of an enzyme used to control the pathways. ldhA and pflB genes were removed to reduce by-products such as lactate, formate and ethanol. A pathway (crr, ptsG, crp) involved in the catabolite repression mechanism was inhibited, while a pathway (xylA, xylB, rpe, rpiA, tktAB, talB) involved in uptake and metabolism of xylose (pentose) was amplified and expressed.

Medium Comprising at Least Two Sugar

It is preferred that a medium comprising at least two sugars is a medium containing lignocellulosic-derived hydrolysate. The medium may contain glucose and at least one sugar selected from a group consisting of xylose, arabinose and cellobiose. In this connection, glucose and xylose may be contained in the hydrolysate in a weight ratio of 5.5:4.5 to 9:1. Preferably, glucose and xylose may be contained in the hydrolysate in a weight ratio of 5.5:4.5 to 8.0:2.0.

Diol Production Ability of Recombinant Microorganism

The diol production ability of the recombinant microorganism according to the present disclosure was calculated as follows.

Diol productivity (g/L/h): amount of diol produced per unit time and unit volume (in this connection, in batch and fed-batch methods, the diol productivity is based on an exponential phase; in continuous culture, the diol productivity is calculated based on a cumulative amount of diols produced in an entire phase).

2,3-butanediol productivity (g/L/h): amount of 2,3-butanediol produced per unit time and unit volume (in this connection, in batch and fed-batch methods, the 2,3-butanediol productivity is based on an exponential phase; in continuous culture, the 2,3-butanediol productivity is calculated based on a cumulative amount of 2,3-butanediol produced in an entire phase)

Yield (%): {2,3-butanediol production amount (g)/carbon source (g)}×100

Concentration (g/L): amount of metabolites produced per unit volume

EXAMPLES

Advantages and features according to the present disclosure, and a method for achieving them will be clarified with reference to embodiments described below in detail. However, the present disclosure is not limited to the embodiments disclosed below, but will be implemented in various different forms. The embodiments are provided to allow the disclosure to be complete, and to completely inform the skilled person to the art of the scope of the disclosure. The present disclosure is only defined by a scope of the claims.

<Material and Method>

A *Klebsiella oxytoca* KCTC 12132BP strain (deposited into Korea Research Institute of Bioscience and Biotechnology on Feb. 8, 2012) was used as a wild-type strain.

Sugar analysis was performed using liquid chromatography. In this connection, a mobile phase was embodied as a 0.01N $H_2SO_4$ solution, and a column was embodied as Aminex87H from the Bio-Rad company.

Wood-derived hydrolysate used in an Experimental Example according to the present disclosure was produced by a following method.

A waste wood was finely chopped and added to a reactor containing 70% sulfuric acid, and was stirred at about 100° C. for 30 minutes for reaction. Thus, pretreatment was done. Then, water was appropriately added to the pretreated slurry in which in turn was hydrolyzed. The hydrolyzed solution contained glucose and xylose derived from cellulose and hemicelluloses. That is, several sugars were present therein in a form of a mixture (The mixture of the sugars is hereinafter referred to as "mixed sugars"). When the hydrolyzed solution was compressed to about 3 bar using a filter press, the mixed sugars were separated from lignin such that the mixed sugars were contained in liquid while lignin was present in a solid state inside the filter Thus, the lignin was removed from the hydrolyzed solution. Then, sulfuric acid was separated from the remaining solution (containing the mixed sugars) using anion exchange resin to produce wood-derived hydrolysate having a concentration of about 100 g/L of the mixed sugars. The wood-derived hydrolysate thus produced was again concentrated such that a concentration of the mixed sugars reached about 200 g/L. Thus obtained concentrate was used as a culture medium for continuous culture.

*Miscanthus sinensis*-derived hydrolysate used in Experimental Example according to the present disclosure was produced by a following method.

*Miscanthus sinensis* was finely chopped and added to a reactor containing 70% sulfuric acid, and was stirred at about 100° C. for 30 minutes for reaction. Thus, pretreatment was done. Then, water was appropriately added to the pretreated slurry in which in turn was hydrolyzed. The hydrolyzed solution contained glucose and xylose derived from cellulose and hemicelluloses. That is, several sugars were present therein in a form of a mixture (The mixture of the sugars is hereinafter referred to as "mixed sugars"). Then, sulfuric acid was separated from the hydrolyzed solution (containing the mixed sugars) using anion exchange resin to produce *Miscanthus sinensis*-derived hydrolysate having a concentration of about 100 g/L of the mixed sugars. The *Miscanthus sinensis*-derived hydrolysate thus produced was again concentrated such that a concentration of the mixed sugars reached about 200 g/L. Thus obtained concentrate was used as a culture medium for continuous culture.

<Experimental Example 1> Preparation of Recombinant Strain

<Comparative Example 1> Preparation of *K. oxytoca* ΔldhA ΔpflB

To clone lactate dehydrogenase and pyruvate formate lyase of *Klebsiella oxytoca*, homologous portions of target genes ldhA (SEQ ID NO: 1) and pflB (SEQ ID NO: 2) were amplified via PCR (Table 1).

In this connection, the amplified DNA fragment may contain an antibiotic resistant gene, etc., in order to increase probability of recombination of the target genes. Further, the amplified DNA fragment may further contain a sacB gene for encoding a levansucrase enzyme in order to remove the antibiotic resistant gene that was later recombined into a chromosome.

TABLE 1

| SEQ ID NO | Sequence |
|---|---|
| 1 | ATGAAAATCGCTGTGTATAGTACAAAACAGTACGACAAGAAGT ATCTGCAGCATGTTAATGATGCATATGGCTTTGAACTGGAGTT TTTTGACTTCCTGCTAACCGAAAAAACCGCCAAAACCGCCAAC GGCTGTGAAGCGGTGTGTATCTTCGTAAACGATGACGGTAGCC GCCCGGTACTTGAAGAACTGAAAGCCCACGGCGTGCAGTACAT CGCGCTGCGCTGCGCGGGGTTCAACAACGTTGACCTCGATGCC GCCAAAGAGCTGGGCCTGCGGGTGGTGCGCGTCCCGGCCTACT CGCCGGAAGCGGTCGCTGAGCACGCGATCGGCATGATGATGTC GCTGAACCGCCGCATTCACCGTGCCTATCAGCGCACCCGCGAC GCGAACTTCTCTCTGGAAGGGCTGACCGGTTTCACCATGCACG GTAAAACCGCCGGCGTTATTGGCACCGGTAAAATCGGCGTCGC CGCGCTGCGCATTCTTAAAGGCTTCGGTATGCGTCTGCTGGCG TTTGATCCCTACCCAAGCGCCGCCGCGCTGGATATGGCGTGG AGTATGTCGATCTTGAAACCCTGTACCGGGAGTCCGATGTTAT CTCACTGCACTGCCCACTGACCGATGAAAACTACCATTTGCTG AACCATGCCGCGTTCGATCGCATGAAAGACGGGGTGATGATCA TCAACACCAGCCGCGGCGCGCTCATCGATTCGCAGGCAGCGAT CGACGCCCTGAAGCATCAGAAAATTGGCGCGCTGGGGATGGAC GTGTATGAGAACGAACGCGATCTGTTCTTTGAAGATAAGTCTA ATGACGTGATTCAGGATGATGTGTTCCGCCGTCTCTCCGCCTG CCATAACGTCCTGTTTACCGGTCACCAGGCGTTTCTGACCGCG GAAGCGTTGATCAGCATTTCGCAAACCACCCTCGACAACCTGC GTCAAGTGGATGCAGGCGAAACCTGTCCTAACGCACTGGTCTG A |
| 2 | ATGTCCGAGCTTAATGAAAAGTTAGCCACAGCCTGGGAAGGTT TTGCGAAAGGTGACTGGCAGAACGAAGTCAACGTCCGCGACTT CATCCAGAAAAACTATACCCCGTACGAAGGTGACGAGTCCTTC CTGGCTGGCGCAACTGACGCGACCACCAAGCTGTGGGACACCG TAATGGAAGGCGTTAAACAGGAAAACCGCACTCACGCGCCTGT TGATTTTGATACTTCCCTTGCATCCACCATCACTTCTCATGAC GCTGGCTACATCGAGAAGGTCTCGAGAAAATCGTTGGTCTGC AGACTGAAGCTCCGCTGAAACGCGCGATTATCCCGTTCGGCGG CATCAAAATGGTCGAAGGTTCCTGCAAAGCGTACGATCGCGAG CTGGACCCGATGCTGAAGAAAATCTTCACTGAATACCGTAAAA CTCACAACCAGGGCGTGTTTGACGTTTACACCAAAGACATGCT GAACTGCCGTAAATCTGGTGTTCTGACCGGTCTGCCGGATGCC TATGGCCGTGGTCGTATCATCGGTGACTACCGTCGCGTTGCGC TGTACGGTATCGACTTCCTGATGAAAGACAAATACGCTCAGTT CGTTTCTCTGCAAGAGAAACTGGAAAACGGCGAAGATCTGGAA GCAACCATCCGTCTGCGCGAAGAAATCTCTGAACAGCACCGCG CGCTGGGTCAGATCAAAGAAATGGCGGCTAAATATCGGCTGGA TATCTCTGGTCCTGCTACCACCGCTCAGGAAGCTATCCAGTGG ACCTACTTCGGTTACCTGGCTGCCGTAAAATCTCAGAACGGCG CGGCAATGTCCTTCGGTCGTACCTCCAGCTTCCTGGACATCTT CATCGAACGTGACCTGAAAGCCGGTAAAATCACCGAGCAAGAC GCACAGGAAATGATTGACCACCTGGTCATGAAACTGCGTATGG TTCGTTTCCTGCGTACCCCTGAATATGATGAACTGTTCTCTGG CGACCCGATCTGGGCAACAGAATCTATCGGCGGTATGGGCGTT GACGGCGTACTCTGGTCACCAAAAACAGCTTCCGTTTCCTGA ACAGCCTGTACACCATGGGCCGTCTCCGGAGCCGAACATCAC CATTCTGTGGTCTGAAAAACTGCCGCTGAGCTTCAAAAAATAC GCCGCGAAAGTGTCCATCGATACCTCTTCTCTGCAGTACGAGA ACGATGACCTGATGCGTCCTGACTTCAACAACGATGACTACGC TATCGCTTGCTGCGTAAGCCCGATGGTTGTTGGTAAGCAAATG CAGTTCTTCGGCGCGCGTGCTAACCTGGCGAAAACCATGCTGT ACGCAATCAACGGCGGCGTTGATGAAAAACTGAAAATGCAGGT TGGTCCTAAATCTGAACCGATCAAAGGCGACGTTCTGAACTTC GACGAAGTGATGGACCGCATGGATCACTTCATGGACTGGCTGG CTAAACAGTACGTCACTGCGCTGAACATCATCCACTACATGCA CGACAAGTACAGCTACGAAGCTTCCCTGATGGCGCTGCACGAC CGTGATGTTATCCGCACCATGGCATGTGGTATCGCAGGTCTTT CCGTTGCGGCTGACTCCCTGTCTGCAATCAAATATGCGAAAGT TAAACCGATTCGTGACGAAAACGGTCTGGCTGTCGACTTCGAA ATCGAAGGCGAATACCCGCAGTTTGGTAACAACGACTCTCGCG TCGATGATATGGCCGTTGACCTGGTTGAACGTTTCATGAAGAA AATTCAGAAACTGCACACCTACCGCAACGCTATCCCGACTCAG TCCGTTCTGACCATCACCTCTAACGTTGTGTATGGTAAGAAAA CCGGCAACACCCCTGACGGTCGTCGCGTGGCGCTCCGTTCGG ACCAGGTGCTAAGCCGATGCACGGCCGTGACCAGAAAGGCGCT GTTGCCTCTCTGACCTCCGTTGCAAAACTGCCGTTTGCTTACG CGAAAGATGGTATTTCTTACACCTTCTCTATCGTGCCGAACGC |

TABLE 1-continued

| SEQ ID NO | Sequence |
|---|---|
| | GCTGGGTAAAGACGACGAAGTTCGTAAAACTAACCTCGCCGGC<br>CTGATGGATGGTTACTTCCACCACGAAGCGTCCATCGAAGGCG<br>GTCAGCATCTGAACGTCAACGTTATGAACCGCGAAATGCTGCT<br>CGACGCGATGGAAAACCCGGAAAAATATCCGCAGCTGACCATC<br>CGCGTATCCGGCTACGCAGTACGTTTTAACTCCCTGACTAAAG<br>AACAGCAGCAGGACGTTATTACTCGTACCTTCACTCAGACCAT<br>GTAA |

The prepared DNA fragments were transferred to *Klebsiella oxytoca* KCTC 12132BP using electroporation (25 uF, 200 Ω, 18 kV/cm). In this connection, a DNA fragment containing a homologous portion of the ldhA gene was transferred thereto, thereby to produce a recombinant *Klebsiella oxytoca* from which the ldhA gene was removed. Thereafter, a DNA fragment containing a homologous portion of the pflB gene was transferred to the recombinant *Klebsiella oxytoca* from which the ldhA gene was removed.

As a result, a recombinant *Klebsiella oxytoca* (*K. oxytoca* ΔldhA ΔpflB) from which the target genes ldhA and pflB were removed was produced.

<Present Example 1> Preparation of *K. oxytoca* ΔldhA ΔpflB Δcrr

To clone a glucose-specific phosphotransferase enzyme HA component of PTS of the *Klebsiella oxytoca*, a homologous portion of a target gene crr (SEQ ID NO: 3) was amplified via PCR.

TABLE 2

| SEQ ID NO | Sequence |
|---|---|
| 3 | ATGGGTTTGTTCGATAAATTGAAATCTCTGGTTTCTGATGACA<br>AAAAGACACCGGAACTATTGAGATTGTTGCCCCGCTCTCTGG<br>CGAGATCGTCAACATTGAAGACGTGCCGGATGTAGTTTTCGCG<br>GAAAAAATTGTGGGTGATGGCATTGCTATCAAACCTACTGGCA<br>ACAAAATGGTTGCGCCGGTAGATGGTACCATCGGTAAAATTTT<br>TGAAACCAACCATGCTTTTTCAATCGAATCTGATAGCGGCATT<br>GAACTGTTCGTTCACTTCGGTATTGATACCGTTGAACTGAAAG<br>GCGAAGGCTTCAAACGTATCGCTGAAGAAGGCCAGCGCGTGAA<br>AGTCGGCGACCCGGTTATCGAATTCGATCTGCCGCTGCTGGAA<br>GAGAAAGCCAAGTCTACCCTGACTCCGGTTGTTATCTCCAACA<br>TGGACGAGATCAAAGAGCTGATCAAACTGTCCGGTAGCGTAAC<br>CGTGGGTGAAACTCCGGTTATCCGCATCAAGAAGTAA |

In this connection, the amplified DNA fragment may contain an antibiotic resistant gene, etc., in order to increase probability of recombination of the target genes. Further, the amplified DNA fragment may further contain a sacB gene for encoding a levansucrase enzyme in order to remove the antibiotic resistant gene that was later recombined into a chromosome.

A DNA fragment containing a homologous portion of the prepared crr gene was transferred to *K. oxytoca* ΔldhA ΔpflB of <Comparative Example 1> using electroporation (25 uF, 200 Ω, 18 kV/cm).

As a result, a recombinant *Klebsiella oxytoca* (*K. oxytoca* ΔldhA ΔpflB Δcrr) from which the target gene crr was further removed was produced.

<Present Example 2> Preparation of *K. oxytoca* ΔldhA ΔpflB ΔptsG

To clone a glucose-specific phosphotransferase enzyme IIBC component of PTS of *Klebsiella oxytoca*, a homologous portion of ptsG (SEQ ID NO: 4) as a target gene was amplified via PCR (Table 3).

In this connection, the amplified DNA fragment may contain an antibiotic resistant gene, etc., in order to increase probability of recombination of the target genes. Further, the amplified DNA fragment may further contain a sacB gene for encoding a levansucrase enzyme in order to remove the antibiotic resistant gene that was later recombined into a chromosome.

TABLE 3

| SEQ ID NO | Sequence |
|---|---|
| 4 | ATGTTTAAGAATGCATTTGCTAACCTGCAGAAGGTCGGTAAAT<br>CGCTGATGCTGCCGGTATCCGTACTGCCTATCGCAGGTATCCT<br>GCTGGGCGTCGGTTCCGCAAACTTCAGCTGGCTGCCAGCCGTA<br>GTTTCCCACGTCATGGCGGAAGCGGGCGGTTCGGTCTTCGCTA<br>ACATGCCGCTGATCTTTGCTATCGGTGTCGCACTTGGCTTCAC<br>TAACAACGACGGCGTATCCGCTCTGGCATCGGTCGTCGCTTAC<br>GGCATCATGGTGAAAACCATGTCCGTGGTTGCACCTCTGGTCC<br>TGCATTTACCTGCTGAAGAGATTGCGGCTAAACACCTGGCGGA<br>TACTGGCGTACTCGGCGGTATTATCTCCGGTGCCATCGCAGCG<br>TACATGTTCAACCGCTTCTACCGCATCAAATTGCCTGAGTATC<br>TGGGCTTCTTTGCGGGCAAGCGTTTTGTGCCAATTATCTCCGG<br>TCTGGCAGCGATCTTCACTGGTGTGATCCTGTCCTTTATCTGG<br>CCGCCGATCGGTACCGCAATCCAGACTTTCTCCCAGTGGGCTG<br>CTTACCAGAACCCGGTTGTGGCGTTCGGTATCTACGGCTTCAT<br>TGAACGCTGCCGGTGCCGTTTGGTCTGCACCACATCTGGAACG<br>TTCCTTTCCAGATGCAGATTGGTGAATACACCAACGCAGCCGG<br>TCAGGTCTTCCACGGCGATATTCCGCGCTACATGGCAGGCGAC<br>CCGACCGCGGGCAAACTGTCCGGCGGCTTCCTGTTCAAAATGT<br>ACGGTCTGCCGGCCGCTGCTATCGCTATCTGGCACTCTGCTAA<br>ACCAGAAAACCGCGCAAAAGTGGGCGGTATCATGATCTCCGCA<br>GCGCTGACCTCGTTCCTGACCGGTATCACCGAGCCGATCGAGT<br>TCTCCTTTATGTTCGTTGCGCCGATCCTGTACGTTATCCATGC<br>GATTCTGGCAGGCCTGGCCTTCCCGATCTGTATCCTGCTGGGT<br>ATGCGTGACGGTACTTCGTTCTCTCATGGTCTGATCGACTTCA<br>TCGTACTGTCCGGCAACAGCAGCAAACTGTGGCTGTTCCCGAT<br>AGTCGGCATCTGCTATGCGATCGTTTACTACGTGGTGTTCCGC<br>GTTCTGATCAAAGCGCTGGATCTGAAAACCCCGGGTCGTGAAG<br>ATGCAACCGAAGACAGCAAAGCTGGCGCCACCAGCGAAATGGC<br>TCCGGCACTGATTGCCGCTTTCGGCGGTAAAGAGAACATTACT<br>AACCTTGACGCATGTATCACCCGTCTGCGCGTGAGCGTAGCGG<br>ATGTGGCGAAAGTTGATCAGGCTGGCCTGAAAAAACTGGGTGC<br>CGCAGGCGTGGTTGTTGCAGGTTCAGGCGTTCAGGCTATTTTC<br>GGTACCAAATCCGATAACCTGAAAACTGAAATGGATGAATACA<br>TCCGCAGCAACTAA |

A DNA fragment containing a homologous portion of the prepared ptsG gene was transferred to *K. oxytoca* ΔldhA ΔpflB of <Comparative Example 1> using electroporation (25 uF, 200 Ω, 18 kV/cm).

As a result, a recombinant *Klebsiella oxytoca* (*K. oxytoca* ΔldhA ΔpflB ΔptsG) from which the target gene ptsG was further removed was produced.

<Present Example 3> Preparation of *K. oxytoca* ΔldhA ΔpflB+pGSC−xylAB

Preparation of Overexpressed Plasmid

To create a recombinant vector that amplifies a target gene expression of *Klebsiella oxytoca*, a gene to be amplified was cloned into pBBR1MCS (Kovach et al., Biotechniques, 800-802, 1994) plasmid containing a restriction enzyme site, a multiple cloning site (MCS) and a chloramphenicol resistant gene. Then, the plasmid was cloned into bacteria, and, then, the gene expression was amplified based on a replication mechanism of the plasmid in a cell.

To clone a gene (xylA, SEQ ID NO: 5) for encoding D-xylose isomerase enzyme of *Klebsiella oxytoca* and a gene (xylB, SEQ ID NO: 6) for encoding xylulokinase enzyme of *Klebsiella oxytoca*, target genes xylA and xylB were amplified via PCR, respectively. In this connection, the amplification was performed using a primer containing a restriction enzyme site (XbaI, ApaI, etc.) present at the multiple cloning site of the plasmid (Table 4).

TABLE 4

| SEQ ID NO | Sequence |
|---|---|
| 5 | ATGCAGACCTATTTTGACCAGCTCGATCGCGTTCGTTATGAAG<br>GCCCGAAATCCGCTAACCCACTGGCTTTCCGTCATTACAACCC<br>GGATGAGCTGGTGCTGGGCAAACGGATGGAAGACCATTTACGC<br>TTTGCGGCCTGCTACTGGCACACCTTCTGCTGGAACGGTGCCG<br>ATATGTTCGGCGTGGGCTCCTTTAACCGCCCGTGGCAGCAGCC<br>GGGTGAAGCAATGGAAATGGCGAAACGTAAAGCCGATGTCGCT<br>TTTGAGTTTTTCCATAAACTGAACGTACCGTACTACTGCTTCC<br>ACGACGTCGACGTTTGTCCTGAAGGGGGATCGCTGAAAGAGTA<br>TGCCAATAACTTCGCACAAATGGTTGATGTGCTTGCGGAAAAA<br>CAGCAGCAAAGCGGCGTCAAGCTGCTGTGGGGCACGGCAAACT<br>GCTTTACGAACCCGCGTTACGGCGCCGGTGCGGCAACCAATCC<br>GGATCCGGAAGTGTTCAGCTGGGCGGCGACCGAGGTGGTGACC<br>GCGATGGATGCGACCCACAAACTGGGCGGTGAAAACTAGGTCC<br>TGTGGGGCGGTCGCGAAGGCTATGAAACCCTGCTGAACACCGA<br>CCTGCGTCAGGAACGGGAGCAGATTGGCCGCTTCATGCAGCTG<br>GTCGTGGAGCATAAACATAAAATCGGCTTCCAGGGTACGCTAC<br>TGATTGAACCGAAACCGCAGGAGCCCACCAAGCATCAGTACGA<br>TTACGACGCGTCTACCGTCTACGGCTTCCTGAAACAGTTCGGC<br>CTGGAAAAAGAGATCAAGCTGAATATCGAAGCGAACCACGCGA<br>CGCTGGGCGGGCACACGTTCCACCACGAAATTGCTACCGCCAT<br>CGCCCTCGGCCTGTTTGGTTCCGTTGACGCTAACCGGGGCGAC<br>CCGCAGCTGGGCTGGGATACTGACCAGTTCCCGAACAGCGTTG<br>AAGAGAACGGGCTTGTGATGTACGAAATCCTTAAAGCGGGCGG<br>CTTCACCACCGGCGGCCTGAACTTTGATGCTAAAGTGCGTCGT<br>CAGAGCACCGACAAATACGAGCTGTTCTACGGCCACATCGGTG<br>CGATGGACACCATGGCGCTGGCGCTGAAAGTCGCTGCCCGTAT<br>GATTGAAGGCGGCGAGCTGGATAAACGCGTTGCCAAACGCTAT<br>GCCGGCTGGAACGGCGAGCTGGGTCAGCAGATCCTCAAAGGCC<br>AGATGAACCTGGCGGACATCGCCCAGTATGCCACTCAGCATAA<br>CCTGGCGCCGCAGCACCAGAGCGGCCATCAGGAACTGCTTGAA<br>AACGTGGTTAACCGCTACCTCTTTGATCGCTGA |
| 6 | ATGTATATCGGGATTGATCTCGGCACCTCGGGCGTTAAGGCCA<br>TTCTGCTCAACGAGCAGGGCGAGGTCGTGGCTTCGCACACCGA<br>AAAGCTCAACGTGTCGCGTCCGCACCCTTTATGGTCTGAACAA<br>GATCCTGAGCACTGGTGGCTGGCGACGGACCGCGCGATGAAAG<br>CGTTGGGCGCGGAGCACTCTTTGCGCGCGGTTAAAGCGTTGGG<br>CATTGCGGGTCAGATGCACGGCGCGACGCTGCTCGATAAGCAA<br>CAGCGCGTCTTGCGCCCGGCGATCTTGTGGAATGATGGCCGCT<br>GCGGCGAGGAGTGTGCGCTGCTGGAGGAGGAAGTCAGCCGTTC<br>GCGACAGATCACCGGTAATCTGATGATGCCGGGATTTACCGCG<br>CCGAAGCTGTTGTGGGTGCAACGTCACGAGCCTGAGATTTTTA<br>GGCAAGTCGATAAGGTTCTGCTGCCAAAAGATTATTTACGTTT<br>GCGTATGACCGGTGAGTTTGCCAGCGATATGTCCGATGCCGCC<br>GGAACGATGTGGATGGACGTGGCGCGCCGCGACTGGAGCGATG<br>AAATGCTCGCCGCCTGTGGGTTGAGCCGCGATAACATGCCAGC<br>GCTTTTCGAAGGATGCGAAGTGACGGGCTCGCTGCGTCCGGCC<br>GTCGCGCAAGCGTGGAATATGCCGGAAGTATTGGTGGTGGCCG<br>GCGGCGGCGACAACGCGGCGGGAGCGGTTGGCGTAGGTATGGC<br>GGATGCGGGCCAGGCGGATGCTGTCGCTGGGGACCTCGGGCGTC<br>TACTTTGGCGTCAGCGACGGCTTTCTTAGCAAACCGGAAAGCG<br>CCGTTCACAGCTTCTGCCACGCGTTGCCTGGACGCTGGCATCT<br>GATGTCGGTCATGCTGAGCGCGGCTTCCTGCCTTGATTGGGCG<br>GCGACATTAACTGGCCTGGGCACGGTTCCGGCGCTGATTGCGG<br>CAGCGGAAGCGGCGAACGACGATGCCGATCCGGTCTGGTTCTT<br>GCCTTATCTCTCGGGTGAACGCACGCCGCACAACAATCCGCAG<br>GCGAAAGGCGTCTTTTTCGGCCTGACTCATCAACACGGTCCGG<br>CGGAGCTGGCGCGGGCGGTGCTGGAGGGAGTTGGTTATGCTCT<br>GGCGGACGGCATGGATGTGGTTCACGCCTGCGGCGTCAAACCG<br>GAGAGCGTCACGCTGATTGGCGGCGGCGCGCAGCGCCTACT<br>GGCGGCAAATGCTGGCGGATATAAGCGGCCAGCAGCTTGATTT<br>CCGCACCGGCGGCGATGTCGGCACCGGCTTGGCGCGGCGCGG<br>CTGGCGCAGCTGGCGCTGCATCGAAATGTCGCGTTTTCCGATC<br>TGCTCCCGCAGCTCCCGCTGGAACAGGCTCATCTTCCGGATGC<br>CGAACGCTTTGCGCGTTACGCACCTCGTAGGGAAACTTTCCGC<br>CAGATTTATCAGCAGCTTTTACCGCTGATGTCCTGA |

The DNA fragment and the plasmid containing the respective genes were treated with the restriction enzyme, located at the multiple cloning site in the same manner.

Then, the DNA fragment and the plasmid were ligated with each other using T4 DNA ligase to produce pGSC-xylAB plasmid.

Amplification of Expression of Xylose Isomerase Enzyme and Xylulokinase Enzyme

The produced pGSC-xylAB plasmid was cloned into K. oxytoca ΔldhA ΔpflB as the recombinant Klebsiella oxytoca of <Comparative Example 1> using electroporation (25 uF, 200 Ω, 18 kV/cm). Thus, K. oxytoca ΔldhA ΔpflB+pGSC-xylAB as a recombinant Klebsiella oxytoca having amplified expression of the xylAB gene was produced.

After performing the electroporation, the K. oxytoca ΔldhA ΔpflB+pGSC-xylAB was cultured at 30° C. for 1 hour and thus was stabilized. Thereafter, the stabilized K. oxytoca ΔldhA ΔpflB+pGSC-xylAB was spread into a LB complex solid medium containing chloramphenicol and was cultured therein at 37° C. Thereafter, colonies grown in the solid medium containing chloramphenicol were collected. Then, the plasmid contained in the collected colonies was separated (Miniprep). Then, it was identified whether the gene was cloned, using electroporation.

<Present Example 4> Preparation of K. oxytoca ΔldhA ΔpflB+pGSC-rpe

Preparation of Overexpressed Plasmid

To create a recombinant vector that amplifies target gene expression of Klebsiella oxytoca, a gene to be amplified was cloned into pBBR1MCS (Kovach et al., Biotechniques, 800-802, 1994) plasmid containing a restriction enzyme site, a multiple cloning site (MCS) and a chloramphenicol resistant gene. Then, the plasmid was cloned into bacteria, and, then, the gene expression was amplified based on a replication mechanism of the plasmid in a cell.

To clone a gene (rpe, SEQ ID NO: 7) for encoding D-ribulose-5-phosphate 3-epimerase of Klebsiella oxytoca, a target gene rpe was amplified via PCR. In this connection, the amplification was performed using a primer containing a restriction enzyme site (XbaI, ApaI, etc.) present at the multiple cloning site of the plasmid (Table 5).

TABLE 5

| SEQ ID NO | Sequence |
|---|---|
| 7 | ATGAAGCAGTATTTGATTGCCCCTTCGATTCTGTCGGCTGATT<br>TTGCCCGTCTGGGCGAGGACACCGCCAATGCGTTGGCTGCGGG<br>TGCGGATGTTGTGCACTTTGACGTGATGGACAACCACTACGTGC<br>CGAATCTGACCATTGGCCCGATGGTGCTGAAATCACTGCGAAA<br>TTACGGTATCACTGCGCCGATTGACGTGCATTTGATGGTCAAG<br>CCGGTTGACCGCATCGTCCCTGATTTTGCCGCCGCGGGCGCCA<br>GCATCATTACTTTCCATCCGGAAGCTTCCGAACACGTTGACCG<br>CAGGCTGCAGCTTATCAAAGAGCACGGCTGCAAAGCCGGTTTG<br>GTGTTTAACCCGGCGACCTCCCTGAGCTACCTTGATTACGTAA<br>TGGATAAGCTGGATGTTATTCTGCTGATGTCCGTCAACCCTGG<br>CTTTGGCGGTCAGTCTTTTATTCCGCACACCCTGGAAAAACTG<br>CGTGAAGTTCGTCGTCGCATTGATGAATCCGGCTACGACATCC<br>GTCTGGAAGTCGACGGCGGCGTAAAAGTCAGCAATATCGCTGA<br>GATTGCCGCCGCCGGTGCGGATATGTTTGTTGCTGGGTCGGCC<br>ATTTTCGATCAGCCTGACTACAAAAAAGTGGTCGATCAAATGC<br>GCAGCGAATTAGCAAAGGTTAGCCATGGATAA |

The plasmid and the DNA fragment containing the rpe gene were treated with the restriction enzyme present at the multiple cloning site in the same manner. Then, the plasmid and the DNA fragment were ligated with each other using T4 DNA ligase, thereby to produce pGSC-rpe plasmid.

Amplification of Expression of D-Ribulose-5-Phosphate 3-Epimerase Enzyme

The produced pGSC-rpe plasmid was cloned into *K. oxytoca* ΔldhA ΔpflB as the recombinant *Klebsiella oxytoca* of <Comparative Example 1> using electroporation (25 uF, 200 Ω, 18 kV/cm). Thus, *K. oxytoca* ΔldhA ΔpflB+pGSC-rpe as a recombinant *Klebsiella oxytoca* having amplified expression of the rpe gene was produced.

After performing the electroporation, the *K. oxytoca* ΔldhA ΔpflB+pGSC-rpe was cultured at 30° C. for 1 hour and thus was stabilized. Thereafter, the stabilized *K. oxytoca* ΔldhA ΔpflB+pGSC-rpe was spread into a LB complex solid medium containing chloramphenicol and was cultured therein at 37° C. Thereafter, colonies grown in the solid medium containing chloramphenicol were collected. Then, the plasmid contained in the collected colonies was separated (Miniprep). Then, it was identified whether the gene was cloned, using electroporation.

<Present Example 5> Preparation of *K. oxytoca* ΔldhA ΔpflB+pGSC-rpiA

Preparation of Overexpressed Plasmid

To create a recombinant vector that amplifies target gene expression of *Klebsiella oxytoca*, a gene to be amplified was cloned into pBBR1MCS (Kovach et al., Biotechniques, 800-802, 1994) plasmid containing a restriction enzyme site, a multiple cloning site (MCS) and a chloramphenicol resistant gene. Then, the plasmid was cloned into bacteria, and, then, the gene expression was amplified based on a replication mechanism of the plasmid in a cell.

To clone a gene (rpiA, SEQ ID NO: 8) for encoding ribose 5-phosphate isomerase of *Klebsiella oxytoca*, a target gene rpiA was amplified via PCR. In this connection, the amplification was performed using a primer containing a restriction enzyme site (XbaI, ApaI, etc.) present at the multiple cloning site of the plasmid (Table 6).

TABLE 6

| SEQ ID NO | Sequence |
|---|---|
| 8 | ATGAAGCAGTATTTGATTGCCCCTTCGATTCTGTCGGCTGATT TTGCCCGTCTGGGCGAGGACACCGCCAATGCGTTGGCTGCGGG TGCGGATGTTGTGCACTTTGACGTGATGGACAACCACTACGTG CCGAATCTGACCATTGGCCCGATGGTGCTGAAATCACTGCGAA ATTACGGTATCACTGCGCCGATTGACGTGCATTTGATGGTCAA GCCGGTTGACCGCATCGTCCCTGATTTTGCCGCCGCGGGCGCC AGCATCATTACTTTCCATCCGGAAGCTTCCGAACACGTTGACC GCACGCTGCAGCTTATCAAAGAGCACGGCTGCAAAGCCGGTTT GGTGTTTAACCCGGCGACCTCCCTGAGCTACCTTGATTACGTA ATGGATAAGCTGGATGTTATTCTGCTGATGTCCGTCAACCCTG GCTTTGGCGGTCAGTCTTTTATTCCGCACACCCTGGAAAAACT GCGTGAAGTTCGTCGTCGCATTGATGAATCCGGCTACGACATC CGTCTGGAAGTCGACGGCGGCGTAAAAGTCAGCAATATCGCTG AGATTGCCGCCGCCGGTGCGGATATGTTTGTTGCTGGGTCGGC CATTTTCGATCAGCCTGACTACAAAAAAGTGGTCGATCAAATG CGCAGCGAATTAGCAAAGGTTAGCCATGGATAA |

The plasmid and the DNA fragment containing the rpiA gene were treated with the restriction enzyme present at the multiple cloning site in the same manner. Then, the plasmid and the DNA fragment were ligated with each other using T4 DNA ligase, thereby to produce pGSC-rpiA plasmid.

Amplification of Expression of Ribose 5-Phosphate Isomerase Enzyme

The produced pGSC-rpiA plasmid was cloned into *K. oxytoca* ΔldhA ΔpflB as the recombinant *Klebsiella oxytoca* of <Comparative Example 1> using electroporation (25 uF, 200 Ω, 18 kV/cm). Thus, *K. oxytoca* ΔldhA ΔpflB+pGSC-rpiA as a recombinant *Klebsiella oxytoca* having amplified expression of rpiA gene was produced.

After performing the electroporation, the *K. oxytoca* ΔldhA ΔpflB+pGSC-rpiA was cultured at 30° C. for 1 hour and thus was stabilized. Thereafter, the stabilized *K. oxytoca* ΔldhA ΔpflB+pGSC-rpiA was spread into a LB complex solid medium containing chloramphenicol and was cultured therein at 37° C. Thereafter, colonies grown in the solid medium containing chloramphenicol were collected. Then, the plasmid contained in the collected colonies was separated (Miniprep). Then, it was identified whether the gene was cloned, using electroporation.

<Present Example 6> Preparation of *K. oxytoca* ΔldhA ΔpflB+pGSC-talB

Preparation of Overexpressed Plasmid

To create a recombinant vector that amplifies target gene expression of *Klebsiella oxytoca*, a gene to be amplified was cloned into pBBR1MCS (Kovach et al., Biotechniques, 800-802, 1994) plasmid containing a restriction enzyme site, a multiple cloning site (MCS), and a chloramphenicol resistant gene. Then, the plasmid was cloned into bacteria, and, then, the gene expression was amplified based on a replication mechanism of the plasmid in a cell.

To clone a gene (talB, SEQ ID NO: 9) for encoding transaldolase B of *Klebsiella oxytoca*, a target gene talB was amplified via PCR. In this connection, the amplification was performed using a primer containing a restriction enzyme site (XbaI, ApaI, etc.) present at the multiple cloning site of the plasmid (Table 7).

TABLE 7

| SEQ ID NO | Sequence |
|---|---|
| 9 | ATGACGGATAAATTGACCTCTCTGCGTCAGTACACCACTGTCG TAGCTGATACCGGAGATATCGCGGCAATGAAGCTGTATCAGCC TCAGGACGCCACGACTAACCCTTCTTTGATTCTCGGCGCGGCT CAGATCCCTGAGTACCGTAAGCTGATCGATGACGCTGTTGCCT GGGCTCGCGGCCAGAGCAGCGACCGCGCGCAGCAGATTATCGA TGCTTCCGATAAGCTGGCGGTGAACATTGGTCTTGAAATCCTT AAGCTGATCCCTGGCCGTATTTCCACCGAAGTCGATGCTCGCC TGTCCTATGACACCGAGGCATCTATCGCCAAAGCTAAGCGCCT TATCAAGCTGTACAACGATGCCGGCATCGGCAAGGATCGCATT CTGATCAAACTGGCTTCGACCTGGCAGGGCATCCGCGCCGCTG AGCAGCTGGAAAAAGAAGGCATCAACTGCAACCTGACGCTGCT GTTCTCCTTCGCTCAGGCACGTGCCTGCGCCGAAGCGGGCGTA TTCCTGATTTCTCCGTTCGTTGGCCGTATCCTCGACTGGTACA AAGCCAATACCGATAAGAAAGAGTACGCGCCGGCAGAAGATCC GGGCGTGGTTTCGGTAAGCGAAATCTACGAATACTACAAACAG CACGGCTACGAGACGGTGGTTATGGGCGCAAGCTTCCGTAACC TCGGCGAGATCCTGGAGCTGGCTGGCTGTGACCGCCTGACTAT CGCTCCGGCCCTGCTGAAAGAGCTGGCGGAAAGCGAAGGCGCT ATCGAGCGTAAACTGGCCTTTAGCGGCGAAGTTAAAGCGCGTC CGGCTCGTATCACCGAATCCGAGTTCCTGTGGCAGCACAACCA GGATCCGATGGCGGTAGACAAACTGGCGGAAGGTATCCGCAAG TTTGCGATCGACCAGGAAAAACTGGAAAAAATGATCGGCGATC TGCTGTAA |

The plasmid and the DNA fragment containing the talB gene were treated with the restriction enzyme present at the multiple cloning site in the same manner. Then, the plasmid and the DNA fragment were ligated with each other using T4 DNA ligase, thereby to produce pGSC-talB plasmid.

Amplification of Expression of Transaldolase B Enzyme

The produced pGSC-talB plasmid was cloned into *K. oxytoca* ΔldhA ΔpflB as the recombinant *Klebsiella oxytoca* of <Comparative Example 1> using electroporation (25 uF, 200 Ω, 18 kV/cm). As a result, *K. oxytoca* ΔldhA ΔpflB+ pGSC-talB as a recombinant *Klebsiella oxytoca* having amplified expression of the talB gene was produced.

After performing the electroporation, the *K. oxytoca* ΔldhA ΔpflB+pGSC-talB was cultured at 30° C. for 1 hour and thus was stabilized. Thereafter, the stabilized *K. oxytoca* ΔldhA ΔpflB+pGSC-talB was spread into a LB complex solid medium containing chloramphenicol and was cultured therein at 37° C. Thereafter, colonies grown in the solid medium containing chloramphenicol were collected. Then, the plasmid contained in the collected colonies was separated (Miniprep). Then, it was identified whether the gene was cloned, using electroporation.

<Present Example 7> Preparation of *K. oxytoca* ΔldhA ΔpflB+pGSC-tktAB

Preparation of Overexpressed Plasmid

To create a recombinant vector that amplifies target gene expression of *Klebsiella oxytoca*, a gene to be amplified was cloned into pBBR1MCS (Kovach et al., Biotechniques, 800-802, 1994) plasmid containing a restriction enzyme site, a multiple cloning site (MCS), and a chloramphenicol resistant gene. Then, the plasmid was cloned into bacteria, and, then, the gene expression was amplified based on a replication mechanism of the plasmid in a cell.

To simultaneously clone a gene tktA (SEQ ID NO: 10) and a tktB (SEQ ID NO: 11) for encoding transketolase of *Klebsiella oxytoca* (hereinafter, a combination of the two genes being referred to as "tktAB"), a target gene tktAB (SEQ ID NO: 12) was amplified via PCR (Table 8). In this connection, the amplification was performed using a primer containing a restriction enzyme site (XbaI, ApaI, etc.) present at the multiple cloning site of the plasmid.

TABLE 8

| SEQ ID NO | Sequence |
|---|---|
| 10 | ATGTCCTCACGTAAAGAGCTTGCTAACGCTATTCGTGCGCTGA GCATGGACGCAGTACAGAAAGCCAAATCCGGTCACCCGGGTGC CCCGATGGGTATGGCTGACATTGCCGAAGTCCTGTGGCGTGAT TTCCTGAATCATAACCCGCAGAACCCGTCCTGGCCGACCGCG ACCGTTTTGTCCTGTCCAACGGCCACGGTTCCATGCTGATTTA CAGCTTGCTGCACCTCACCGGTTATGATCTGCCGATTGAAGAG CTGAAGAACTTCCGTCAGCTGCACTCTAAAACGCCGGGTCACC CGGAAGTCGGCTACACCGCGGGCGTGGAAACCACTACCGGTCC GCTGGGGCAGGGTATTGCGAATGCGGTTGGTATGGCCATCGCG GAGAAAACTCTGGCGGCGCAGTTCAACCGCCCGGGCCACGACA TTGTTGACCACTTCACCTACGCGTTCATGGGCGACGGCTGGAT GATGGAAGGTATCTCTCACGAGGTATGCTCCCTGGCCGGTACC CTGAAGCTTGGCAAGCTGGTGGCGTTCTATGACGACAACGGCA TCTCTATCGACGGTCATGTAGAAGGTTGGTTCACCGATGACAC CGCGAAGCGTTTTGAAGCCTACGGCTGGCACGTGGTGCGCGGC GTTGACGGCCACGATGCTGACTCGATTAAACGCGCGGTAGAAG AAGCGCGTGCGGTCACCGACAAACCGTCCCTGCTGATGTGCAA AACCATTATTGGTTTCGGTTCGCCGAACAAAGCCGGTACCCAC GACTCCCACGGCGCGCCGCTGGGCGACGCGGAAATCGCGCTGA CCCGCGAAGCGCTCGGCTGGAAACACCCGGCATTTGAAATCCC GTCTGAAATCTATGCCCAGTGGGATGCCAAAGAAGCCGGCCAG GCGAAAGAGTCCGCGTGGAACGAGAAATTTGCCGCCTACGCCA AAGCCTTCCCGCAGGAAGCCGCCGAGTTTACTCGTCGTATGAA AGGCGACATGCCGGCTGACTTCGATGCGAAAGCGAACGAGTTC ATCGCGAAGCTGCAGGCTAACCCGGCAGAAATCGCCAGCCGTA AAGCATCTCAGAACGCCATTGAAGCCTTCGGCCCGCTGCTGCC TGAGTTCCTTGGCGGTTCCGCTGACCTGGCGCCAAGTAACCTG ACCCTGTGGTCCGGTTCTAAAGCGATCAAGGAAGACACTGCCG GTAACTACATCCACTACGGCGTGCGCGAATTCGGTATGACCGC GATTGCCAAGGGTATCGCTCTGCACGGCGGTTTCCTGCCGTAC ACCTCTACCTTCCTGATGTTCGTCGAGTATGCGCGTAACGCGG TACGTATGGCCGCGCTGATGAAACAGCGTCAGGTAATGGTCTA CACCCACGACTCCATCGGTCTGGGCGAAGACGGCCCGACTCAC CAGCCGGTAGAGCAGGTGGCTTCCCTGCGCGTCACGCCGAAGA TGTCCACATGGGGTCCGTGCGACCAGGTGGAATCCGCCATCGC GTGGAAATATGGCGTTGAGCGTCAGGACGGCCCGACCGCGCTG ATTCTGTCCCGTCAGAACCTGGCGCAGCAGGAGCGTACTGAAG AGCAGCTGGCGAACGTTGCCCGCGGCGGCTACGTGCTGAAGGA TTGTGCCGGTCAGCCGGAACTGATCTTCATCGCCACCGGCTCT GAAGTTGAGCTGGCGGTTGCCGCTTACGAAAAATTGACTGCCG AAGGCGTGAAGGCGCGCGTGGTTTCCATGCCGTCCACCGAGGC GTTCGACAAGCAGGATGCCGCTTACCGTGAAGCCGTGCTGCCG AAAGCCGTCTCTGCGCGCGTAGCTATCGAAGCGGGTATCGCCG ACTACTGGTTCAAATACGTGGGCCTGAACGGCGCGATCGTTGG CATGACCACTTTCGGTGAGTCTGCGCCGGCGGAGCTGCTGTTT GAAGAGTTTGGCTTCACCGTGGATAACGTTGTCGCCAAAGCGA AAGCACTGCTGTAG |
| 11 | ATGTCCCGTAGAGAACTCGCTAACGCCATCCGCGCCCTGAGTA TGGATGCAGTCCAGAAAGCCAACTCCGGCCACCCCGGCGCGCC GATGGGCATGGCCGATATCGCAGAGGTGCTGTGGAACGATTTC CTTAAGCACAATCCTGAAAACCCGCAATGGTACGATCGCGACC GCTTTATTCTCTCCAACGGCCACGCGTCGATGCTGCTCTACAG CCTGCTGCATCTGACGGGCTATGACTTGCCCATCGAAGAGATA AAAAACTTCCGTCAGTTGCATTCCAAAACGCCGGCGCACCCGG AAATCGGCTATACCCCGGGGGTTGAAACCACCACCGGGCCGCT GGGGCAAGGGCTGGCGAACGCGGTGGGCTGGCTATCGCCGAG CGTACGCTGGCGGCGCAGTTTAATCAGCCAGACCATGAGATCG TCGATCACTTTACCTACGTGTTTATGGGCGATGGCTGTCTGAT GGAGGGGATTTCTCACGAAGTCTGCTCTCTGGCGGGTACGTTA GGACTGCGTAAGCTCATCGGCTTCTACGACCACAACGGTATTT CCATTGATGGCGAAACCAAAGGCTGGTTTACCGATGACACGGC AAAACGCTTCGAGGCCTATCACTGGCATGTGGTTCATGAAATT GACGGCCACGATCCCGAAGCCGTGAAGAAAGCGATTCTGGAAG CCCAGAGCGTGAAGGATAAACCTTCGCTGATTATCTGCCGTAC GGTAATAGGTTTTGGTTCACCGAATAAAGCCGGGAAAGAAGAG GCCCACGGCGCCGCGCTGGGCGAACAGGAAGTGGCGCTGGCGC GCCAGCAGCTGGGCTGGCATCATCCGGCGTTTGAGATCCCGAA AGAGATCTACCGCGCCTGGGACGCGCGTGAAAAGGGACAAAAA GCGCAGAAAAGCTGGGAGGAGAAGTTTGCCGCCTATCAGCAGG TCCATCCTCAGCTGGCAGCTGAGTTTACGCGGCGCATGAGCGG CGGACTGCCTGAGTCGTGGGATGAAACAACGCGGAAATATATC GCTGAGCTGCAGGCCAACCCGGCGAAAATCGCCACGCGTAAGG CTTCGCAAAACGCCCTTGATGCCTACGGCCCGCATCTACCAGA ACTGTTGGGCGGCTCCGCTGACCTCGCGCCAAGTAACCTGACT ATCTGGAAAGGTTCCACTTCGCTGAAAGAAGATCCGGCGGGCA ACTATATTCACTACGGCGTAGGTGAATTCGGGATGACGGCCAT CGCCAACGGCATCGCCCACCACGGCGGGTTTCTACCTTATACT GCCACCTTCCTGATGTTCGTCGAATATGCCCGCAACGCGGCGC GTATGGCGGCGTTGATGAAAGCGCGGCAAATCATGGTCTATAC CCACGACTCCATCGGTCTCGGCGAAGATGGTCCGACGCACCAG GCGGTAGAACAGCTGGCCAGCCTGCGCCTGACGCCAAACTTGA GCACCTGCCGCCATGCGATCAGGTCGAGGCCGCGGTGGCGTG GAAACTGGCGGTAGAGCGTCATAGCGGGCCGACGGCGCTAATT CTCTCAAGGCAAAATCTGGCACAAATGGCGCGCACGCCGGAAC AGGTACAGAATATCGCCCGCGGCGGCTACGTACTGAAGGACGC CGGCGGCAAGCCGGACCTGATCCTGATAGCCACCGGTTCAGAG GTCGAGATCACCGTACTGGCCGCAGAAAAGCTGCTGGCCAAAG GGGTGAACGTGCGCGTGGTCTCCCTGCCATCGACCGACGTATT TGATGCCCAGGATGAAGCCTATCGGGAGTCCGTACTGCCATCA GACGTCAGCGCCCGCGTTGCCGTGGAGGCAGGGATCGCCGACT ACTGGTATAAATATGTGGGACTCAAAGGAAAAATTGTCGGTAT GACCGGCTACGGTGAATCGGCCCCGGCCGATAAACTTTTCCCT TACTTCGGCTTCACCGTTGAGCATATCGTCAACGTAGGGGACG AGGTACAGAACGGGTAA |
| 12 | ATGTCCTCACGTAAAGAGCTTGCTAACGCTATTCGTGCGCTGA GCATGGACGCAGTACAGAAAGCCAAATCCGGTCACCCGGGTGC CCCGATGGGTATGGCTGACATTGCCGAAGTCCTGTGGCGTGAT TTCCTGAATCATAACCCGCAGAACCCGTCCTGGGCCGACCGCG ACCGTTTTGTCCTGTCCAACGGCCACGGTTCCATGCTGATTTA CAGCTTGCTGCACCTCACCGGTTATGATCTGCCGATTGAAGAG CTGAAGAACTTCCGTCAGCTGCACTCTAAAACGCCGGGTCACC CGGAAGTCGGCTACACCGCGGGCGTGGAAACCACTACCGGTCC GCTGGGGCAGGGTATTGCGAATGCGGTTGGTATGGCCATCGCG GAGAAAACTCTGGCGGCGCAGTTCAACCGCCCGGGCCACGACA TTGTTGACCACTTCACCTACGCGTTCATGGGCGACGGCTGCAT GATGGAAGGTATCTCTCACGAGGTATGCTCCCTGGCCGGTACC CTGAAGCTTGGCAAGGGGTGGCGTTCTATGACGACAACGGCAT CTCTATCGACGGTCATGTAGAAGGTTGGTTCACCGATGACACC GCGAAGCGTTTTGAAGCCTACGGCTGGCACGTGGTGCGCGGC |

TABLE 8-continued

| SEQ ID NO | Sequence |
|---|---|
| | TTGACGGCCACGATGCTGACTCGATTAAACGCGCGGTAGAAGA<br>AGCGCGTGCGGTCACCGACAAACCGTCCCTGCTGATGTGCAAA<br>ACCATTATTGGTTTCGGTTCGCCGAACAAAGCCGGTACCCACG<br>ACTCCCACGGCGCGCCGCTGGGCGACGCGGAAATCGCGCTGAC<br>CCGCGAAGCGCTCGGCTGGAAACACCCGGCATTTGAAATCCCG<br>TCTGAAATCTATGCCCAGTGGGATGCCAAAGAAGCCGGCCAGG<br>CGAAAGAGTCCGCGTGGAACGAGAAATTTGCCGCCTACGCCAA<br>AGCCTTCCCGCAGGAAGCCGCCGAGTTTACTCGTCGTATGAAA<br>GGCGACATGCCGGCTGACTTCGATGCGAAAGCGAACGAGTTCA<br>TCGCGAAGCTGCAGGCTAACCCGGCGAAAATCGCCAGCCGTAA<br>AGCATCTCAGAACGCCATTGAAGCCTTCGGCCCGCTGCTGCCT<br>GAGTTCCTTGGCGGTTCCGCTGACCTGGCGCCAAGTAACCTGA<br>CCCTGTGGTCCGGTTCTAAAGCGATCAACGAAGACACTGCCGG<br>TAACTACATCCACTACGGCGTGCGCGAATTCGGTATGACCGCG<br>ATTGCCAACGGTATCGCTCTGCACGGCGGTTTCCTGCCGTACA<br>CCTCTACCTTCCTGATGTTCGTCGAGTATGCGCGTAACGCGGT<br>ACGTATGGCCGCGCTGATGAAACAGCGTCAGGTAATGGTCTAC<br>ACCCACGACTCCATCGGTCTGGGCGAAGACGGCCGCGACTCACC<br>AGCCGGTAGAGCAGGTGGCTTCCCTGCGCGTCACGCCGAACAT<br>GTCCACATGGCGTCCGTGCGACCAGGTGGAATCCGCCATCGCG<br>TGGAAATATGGCGTTGAGCGTCAGGACGGCCCGACCGCGCTGA<br>TTCTGTCCCGTCAGAACCTGGCGCCAGCAGGAGCGTACTGAAGA<br>GCAGCTGGCGAACGTTGCCCGCGGCGGCTACGTGCTGAAGGAT<br>TGTGCCGGTCAGCCGGAACTGATCTTCATCGCCACCGGCTCTG<br>AAGTTAGCTGGCGGTTGCCGCTTACGAAAAATTGACTGCCGAA<br>GGCGTGAAGGCGCGCGGTGTTTCCATGCCGTCCACCGACGCGT<br>TCGACAAGCAGGATGCCGCTTACCGTGAAGCCGTGCTGCCGAA<br>AGCCGTCTCTGCGCGCGTAGCTATCGAAGCGGGTATCGCCGAC<br>TACTGGTTCAAATACGTGGGCCTGAACGGCGCGATCGTTGGCA<br>TGACCACTTTCGGTGAGTCTGCGCCGGCGGAGCTGCTGTTTGA<br>AGAGTTTGGCTTCACCGTGGATAACGTTGTCGCCAAAGCGAAA<br>GCACTGCTGTAGATGTCCCGTAGAGAACTCGCTAACGCCATCC<br>GCGCCCTGAGTATGGATGCAGTCCAGAAAGCCAACTCCGGCCA<br>CCCCGGCGCGCCGATGGGCATGGCCGATATCGCAGAGGTGCTG<br>TGGAACGATTTCCTTAAGCACAATCCTGAAAACCCGCAATGGT<br>ACGATCGCGACCGCTTTATTCTCTCCAACGGCCACGCGTCGAT<br>GCTGCTCTACAGCCTGCTCCATCTGACGGGCTATGACTTGCCC<br>ATCGAAGAGATAAAAACTTCCGTCAGTTGCATTCCAAAACGC<br>CGGGGCACCCGGAAATCGGCTATACCCCGGGGGTTGAAACCAC<br>CACCGGGCCGCTGGGGCAAGGGCTGGCGAACGCGGTGGGGCTG<br>GCTATCGCCGAGCGTACGCTGGCGGCGCAGTTTAATCAGCCAG<br>ACCATGAGATCGTCGATCACTTTACCTACGTGTTTATGGGCGA<br>TGGCTGTCTGATGGAGGGGATTTCTCACGAAGTCTGCTCTCTG<br>GCGGGTACGTTAGGACTGGGTAAGCTCATCGGCTTCTACGACC<br>ACAACGGTATTTCCATTGATGGCGAAACCAAAGGCTGGTTTAC<br>CGATGACACGGCAAAACGCTTCGAGGCCTATCACTGGCATGTG<br>GTTCATGAAATTGACGGCCACGATCCCGAAGCCGTGAAGAAAG<br>CGATTCTGGAAGCCCAGAGCGTGAAGGATAAACCTTCGCTGAT<br>TATCTGCCGTACGGTAATAGGTTTTGGTTCACCGAATAAAGCC<br>GGGAAGAAGAGGCGCACGGCGCCGCGCTGGGCGAACAGGAAG<br>TGGGGCTGGCGCGCCAGCAGCTGGGCTGGCATCATCCGGCGTT<br>TGAGATCCCGAAAGAGATCTACCGCGCCTGGGACGCGCGTGAA<br>AAGGGACAAAAGCGCAGAAAAGCTGGGAGGAGAAGTTTGCCG<br>CCTATCAGCAGGTCCATCCTCAGCTGGCAGCTGAGTTTACGCG<br>GCGCATGAGCGGCGGACTGCCTGAGTCGTGGGATGAAACAACG<br>CGGAAATATATCGCTGAGCTGCAGGCCAACCCGGCGAAAATCG<br>GCACGCGTAAGGCTTCGCAAAACGCGCTTGATGCCTAGGGCCC<br>GCATCTACCAGAACTGTTGGGCGGCTCCGCTGACCTCGCGCCA<br>AGTAACCTGACTATCTGGAAAGGTTCGACTTCGCTGAAAGAAG<br>ATCCGGCGGGCAACTATATTCACTACGGCGTACGTGAATTCGG<br>GATGACGGCCATCGCCAACGGCATCGCCCACCACGGCGGGTTT<br>CTACCTTATACTGCCACCTTCCTGATGTTCGTCGAATATGCCC<br>GCAAGGCGGCGCGTATGCGGCGTTGATGAAAGCGCGGCAAAT<br>CATGGTCTATAGCCACGACTCCATCGGTCTCGGCGAAGATGGT<br>CCGACGCACCAGGCGGTAGAACAGCTGGCCAGCCTGCGCCTGA<br>CGCCAAACTTCAGCACCTGGCGACCATGCGATCAGGTCGAGGC<br>CGCGGTGGCGTGGAAACTGGCGGTAGAGCGTCATAGCGGGCCG<br>ACGGCGCTAATTCTCTCAAGGCAAATCTGGCACAAATGGCGC<br>GCACGCCGGAACAGGTACAGAATATCGCCCGCGGCGGCTACGT<br>ACTGAAGGACGCCGGCGGCAAGCCGGACCTGATCCTGATAGCC<br>ACCGGTTCAGAGGTCGAGATCACCGTACTGGCCGCAGAAAAGA<br>GCTGGCCAAAGGGGTGAACGTGCGCGTGGTCTCCCTGCCATCG<br>ACCGACGTATTTGATGCCCAGGATGAAGCCTATCGGGAGTCCG<br>TACTGCCATCAGACGTCAGCGCCCGCGTTGCCGTGGAGGCAGG<br>GATCGCCGACTACTGGTATAAATATGTGGGACTCAAAGGAAAA |
| 5 | ATTGTCGGTATGACCGGCTACGGTGAATCGGCCCCGGCCGATA<br>AACTTTTCCCTTACTTCGGCTTCACCGTTGAGCATATCGTCAA<br>CGTAGGGGACGAGGTACAGAACGGGTAA |

The plasmid and the DNA fragment containing the tktAB gene were treated with the restriction enzyme present at the multiple cloning site in the same manner. Then, the plasmid and the DNA fragment were ligated with each other using T4 DNA ligase, thereby to produce pGSC-tktAB plasmid.

Amplification of Expression of Transketolase Enzyme

The produced pGSC-tktAB plasmid was cloned into *K. oxytoca* ΔldhA ΔpflB as the recombinant *Klebsiella oxytoca* of <Comparative Example 1> using electroporation (25 uF, 200 Ω, 18 kV/cm). Thus, *K. oxytoca* ΔldhA ΔpflB+pGSC-tktAB as a recombinant *Klebsiella oxytoca* having amplified expression of the talB gene was produced.

After performing the electroporation, the *K. oxytoca* ΔldhA ΔpflB+pGSC-tktAB was cultured at 30° C. for 1 hour and thus was stabilized. Thereafter, the stabilized *K. oxytoca* ΔldhA ΔpflB+pGSC-tktAB was spread into a LB complex solid medium containing chloramphenicol and was cultured therein at 37° C. Thereafter, colonies grown in the solid medium containing chloramphenicol were collected. Then, the plasmid contained in the collected colonies was separated (Miniprep). Then, it was identified whether the gene was cloned, using electroporation.

<Present Example 8> Preparation of *K. oxytoca* ΔldhA ΔpflB+pGSC-crp(in)01

Preparation of Overexpressed Plasmid

A recombinant plasmid was used to amplify expression of a gene in which a partial DNA sequence of crp as a gene for encoding a cAMP-activated global transcription factor as *Klebsiella oxytoca*-derived cAMP receptor protein was modified.

To create a recombinant vector that amplifies target gene expression of *Klebsiella oxytoca*, a gene to be amplified was cloned into pBBR1MCS (Kovach et al., Biotechniques, 800-802, 1994) plasmid containing a restriction enzyme site, a multiple cloning site (MCS), and a chloramphenicol resistant gene. Then, the plasmid was cloned into bacteria, and, then, the gene expression was amplified based on a replication mechanism of the plasmid in a cell.

To clone crp(in)01 as a gene for encoding the cAMP-activated global transcription factor as the cAMP receptor protein of *Klebsiella oxytoca*, a target gene crp(in)01 (SEQ ID NO: 13) was amplified via PCR. The crp(in)01 gene is a modification of a portion of a DNA sequence of a crp gene involved in the catabolite repression. Because the partial sequence thereof is modified, the catabolite repression does not work in the crp(in)01 gene. Thus, glucose (C6) and xylose (C5) are metabolized simultaneously, thereby increasing 2,3-butanediol productivity. In this connection, the amplification was performed using a primer containing the modified DNA sequence at a restriction enzyme site (XbaI, ApaI, etc.) present at the multiple cloning site of the plasmid (Table 9).

TABLE 9

| SEQ ID NO | Sequence |
|---|---|
| 13 | ATGGTGCTTGGCAAACCGCAAACAGACCCTACCCTTGAATGGT<br>TCTTGTCTCATTGCCACATTCATAAGTACCCATCAAAGAGCAC<br>GCTGATCCACCAGGGTGAGAAAGCAGAAACGTTGTACTACATC<br>GTTAAAGGCTCCGTGGCTGTACTCATCAAGGATGAAGAAGGTA<br>AAGAGATGATCCTCTCTTACCTCAATCAGGGCGATTTCATCGG<br>TGAATTAGGCTTGTTTGAAGAAGGCCAGGAGCGTAGCGCTTGG<br>GTACGTGCGAAAACCGCATGTGAAGTGGCCGAAATCTCCTACA<br>AAAAATTCCGTCAGCTGATCCAGGTTAACCCGGACCTCCTGAT<br>GCGTCTCTCTTCGCAGATGGCTCGTCGTCTGCAGGTCATCTCT<br>GAGAAAGTGGGTAACCTCGCCTTCCTCGACGTTACCGGTCGTA<br>TCACCCAGACGCTGCTGAACCTGGCTAAACAGCCGGATGCGAT<br>GACCCACCCGGACGGTATGCAAATTAAAATTACCCGCCAGGAA<br>ATCGGTCAGATCGTCGGATGCTCCCGCGAGACCGTTGGCCGTA<br>TCCTGAAAATGCTGGAAGATCAAAACCTGATCTCCGCGCACGG<br>TAAAACTATCGTCGTCTACGGTACCCGTTAA |

The plasmid and the DNA fragment containing the crp (in)01 gene were treated with the restriction enzyme present at the multiple cloning site in the same manner. Then, the plasmid and the DNA fragment were ligated with each other using T4 DNA ligase, thereby to produce pGSC-crp(in)01 plasmid. Then, the pGSC-crp(in)01 plasmid was used as an overexpressed plasmid.

Amplification of Expression of cAMP-Activated Global Transcription Factor

Expression of crp(in)01 as a gene for encoding the *Klebsiella oxytoca*-derived cAMP-activated global transcription factor was amplified.

The produced pGSC-crp(in)01 plasmid was cloned into *K. oxytoca* ΔldhA ΔpflB as the recombinant *Klebsiella oxytoca* of <Comparative Example 1> using electroporation (25 uF, 200 Ω, 18 kV/cm). Thus, *K. oxytoca* ΔldhA ΔpflB+ pGSC-crp(in)01 as a recombinant *Klebsiella oxytoca* having amplified expression of the crp(in)01 gene was produced.

After performing the electroporation, the *K. oxytoca* ΔldhA ΔpflB+pGSC-crp(in)01 was cultured at 30° C. for 1 hour and thus was stabilized. Thereafter, the stabilized *K. oxytoca* ΔldhA ΔpflB+pGSC-crp(in)01 was spread into a LB complex solid medium containing chloramphenicol and was cultured therein at 37° C. Thereafter, colonies grown in the solid medium containing chloramphenicol were collected. Then, the plasmid contained in the collected colonies was separated (Miniprep). Then, it was identified whether the gene was cloned, using electroporation.

<Present Example 9> Preparation of *K. oxytoca* ΔldhA ΔpflB+pGSC-crp(in)02

Preparation of Overexpressed Plasmid

A recombinant plasmid was used to amplify expression of a gene in which a partial DNA sequence of crp as a gene for encoding a cAMP-activated global transcription factor derived from *Klebsiella oxytoca* was modified.

To create a recombinant vector that amplifies target gene expression of *Klebsiella oxytoca*, a gene to be amplified was cloned into pBBR1MCS (Kovach et al., Biotechniques, 800-802, 1994) plasmid containing a restriction enzyme site, a multiple cloning site (MCS), and a chloramphenicol resistant gene. Then, the plasmid was cloned into bacteria, and, then, the gene expression was amplified based on a replication mechanism of the plasmid in a cell.

To clone crp(in)02 as a gene for encoding the cAMP-activated global transcription factor as the cAMP receptor protein of *Klebsiella oxytoca*, a target gene crp(in)02 (SEQ ID NO: 14) was amplified via PCR. The crp(in)02 gene is a modification of a portion of a DNA sequence of a crp gene involved in the catabolite repression. Because the partial sequence thereof is modified, the catabolite repression does not work in the crp(in)02 gene. Thus, glucose (C6) and xylose (C5) are metabolized simultaneously, thereby increasing 2,3-butanediol productivity. In this connection, the amplification was performed using a primer containing the modified DNA sequence at a restriction enzyme site (XbaI, ApaI, etc.) present at the multiple cloning site of the plasmid (Table 10).

TABLE 10

| SEQ ID NO | Sequence |
|---|---|
| 14 | ATGGTGCTTGGCAAACCGCAAACAGACCCTACCCTTGAATGGT<br>TCTTGTCTCATTGCCACATTCATAAGTACCCATCAAAGAGCAC<br>GCTGATCCACCAGGGTGAGAAAGCAGAAACGTTGTACTACATC<br>GTTAAAGGCTCCGTGGCTGTACTCATCAAGGATGAAGAAGGTA<br>AAGAGATGATCCTCTCTTACCTCAATCAGGGCGATTTCATCGG<br>TGCATTAGGCTTGTTTGAAGAAGGCCAGGAGCGTAGCGCTTGG<br>GTACGTGCGAAAACCGCATGTGAAGTGGCCGAAATCTCCTACA<br>AAAAATTCCGTCAGCTGATCCAGGTTAACCCGGACATCCTGAT<br>GCGTCTCTCTTCGCAGATGGCTCGTCGTCTGCAGGTCACGTCT<br>GAGAAAGTGGGTAACCTCGCCTTCCTCGACGTTACCGGTCGTA<br>TCACCCAGACGCTGCTGAACCTGGCTAAACAGCCGGATGCGAT<br>GACCCACCCGGACGGTATGCAAATTAAAATTACCCGCCAGGAA<br>ATCGGTCAGATCGTCGGATGCTCCCGCGAGACCGTTGGCCGTA<br>TCCTGAAAATGCTGGAAGATCAAAACCTGATCTCCGCGCACGG<br>TAAAACTATCGTCGTCTACGGTACCCGTTAA |

The plasmid and the DNA fragment containing the crp (in)02 gene were treated with the restriction enzyme present at the multiple cloning site in the same manner. Then, the plasmid and the DNA fragment were ligated with each other using T4 DNA ligase, thereby to produce pGSC-crp(in)02 plasmid. Then, the pGSC-crp(in)02 plasmid was used as an overexpressed plasmid.

Amplification of Expression of cAMP-Activated Global Transcription Factor

Expression of crp(in)02 as a gene for encoding the *Klebsiella oxytoca*-derived cAMP-activated global transcription factor was amplified.

The produced pGSC-crp(in)02 plasmid was cloned into *K. oxytoca* ΔldhA ΔpflB as the recombinant *Klebsiella oxytoca* of <Comparative Example 1> using electroporation (25 uF, 200 Ω, 18 kV/cm). Thus, *K. oxytoca* ΔldhA ΔpflB+ pGSC-crp(in)02 as a recombinant *Klebsiella oxytoca* having amplified expression of the crp(in)02 gene was produced.

After performing the electroporation, the *K. oxytoca* ΔldhA ΔpflB+pGSC-crp(in)02 was cultured at 30° C. for 1 hour and thus was stabilized. Thereafter, the stabilized *K. oxytoca* ΔldhA ΔpflB+pGSC-crp(in)02 was spread into a LB complex solid medium containing chloramphenicol and was cultured therein at 37° C. Thereafter, colonies grown in the solid medium containing chloramphenicol were collected. Then, the plasmid contained in the collected colonies was separated (Miniprep). Then, it was identified whether the gene was cloned, using electroporation.

<Experimental Example 2> Evaluation of Simultaneous Fermentation Ability of Glucose and Xylose in Batch Fermentation The simultaneous fermentation performance of glucose and xylose by the *Klebsiella oxytoca* KCTC 12132BP as the wild-type strain, and the recombinant *K. oxytoca* of each of Comparative Example 1 and Present Examples 1 to 9 in a batch fermentation method was evaluated. These strains were inoculated into 250 ml of a complex medium containing 9 g/L glucose (50 mM glucose) and were cultured for 16 hours at 37° C., and then the culture solution was inoculated into 3 L complex medium. The fermentation conditions were as follows: aerobic condition (micro-aerobic condition; aerobic speed 1 vvm, stirring speed 550 rpm), 60 g/L initial glucose concentration, 40 g/L initial xylose concentration, pH 6.5, and culture temperature of 37° C. For adjustment of pH during the fermentation, 5N NaOH was used. The wild-type and the recombinant Klebsiella were sampled during the fermentation. A growth speed thereof was evaluated by measuring OD600 (optical density) of each of the collected samples. Each of the collected samples was centrifuged at 13,000 rpm for 10 minutes, and then metabolite and 2,3-butanediol concentration of a supernatant were analyzed using liquid chromatography (HPLC).

In this connection, the recombinant strains of Present Examples 3 to 9 were cultured in the medium having 25 mg/L of chloramphenicol added thereto.

Figure 2:
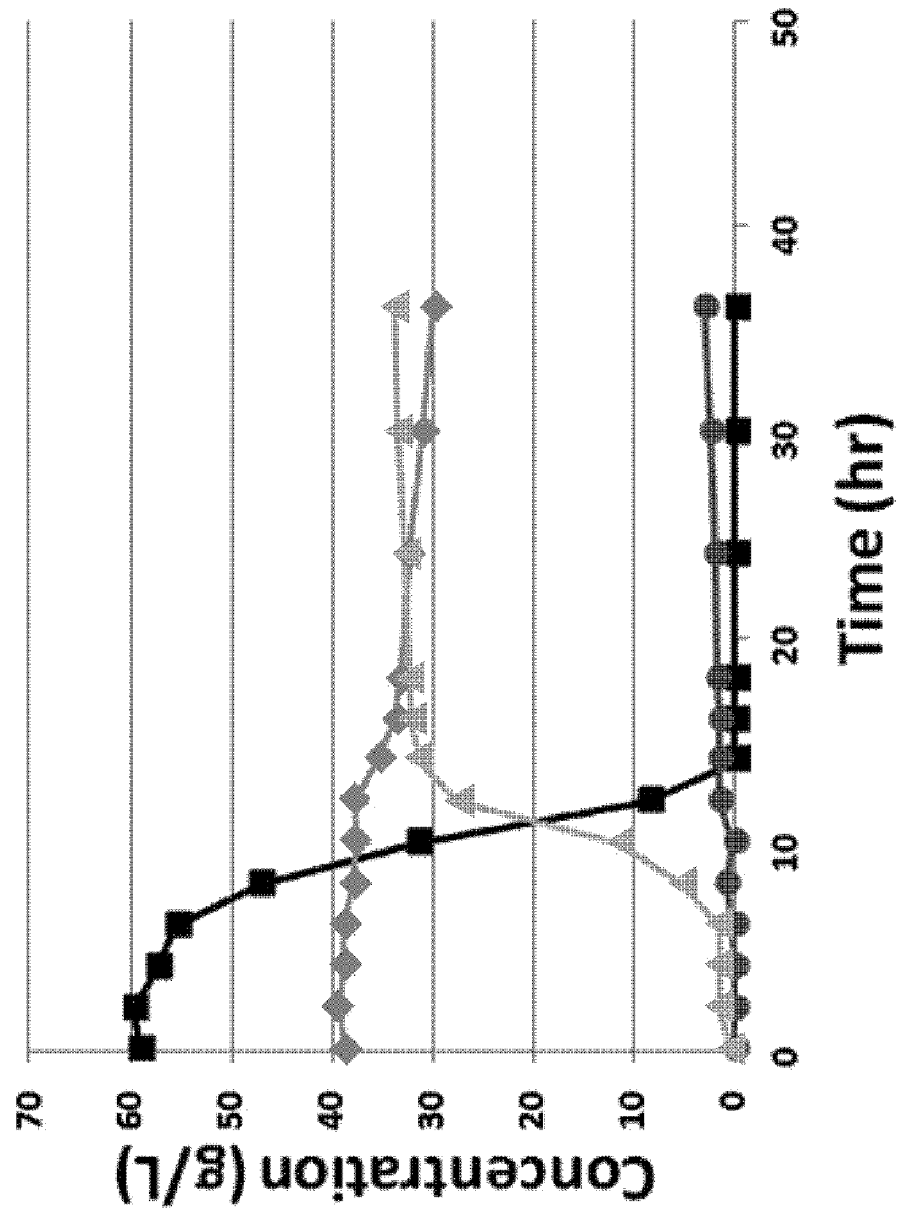
FIG. 2 shows simultaneous fermentation ability of glucose and xylose by *Klebsiella oxytoca* KCTC 12132BP.
Figure 3:
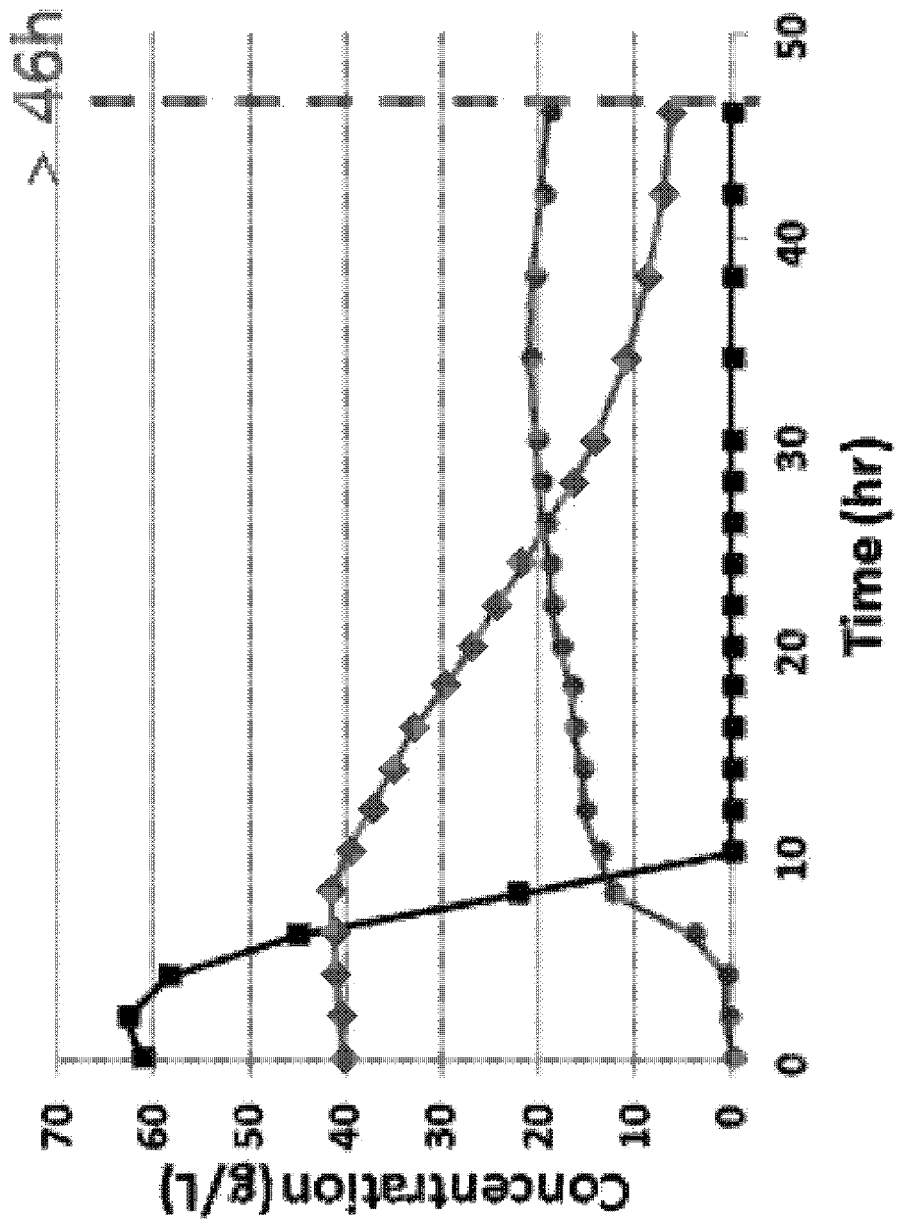
FIG. 3 shows simultaneous fermentation ability of glucose and xylose by a recombinant strain of Comparative Example 1.
Figure 4:
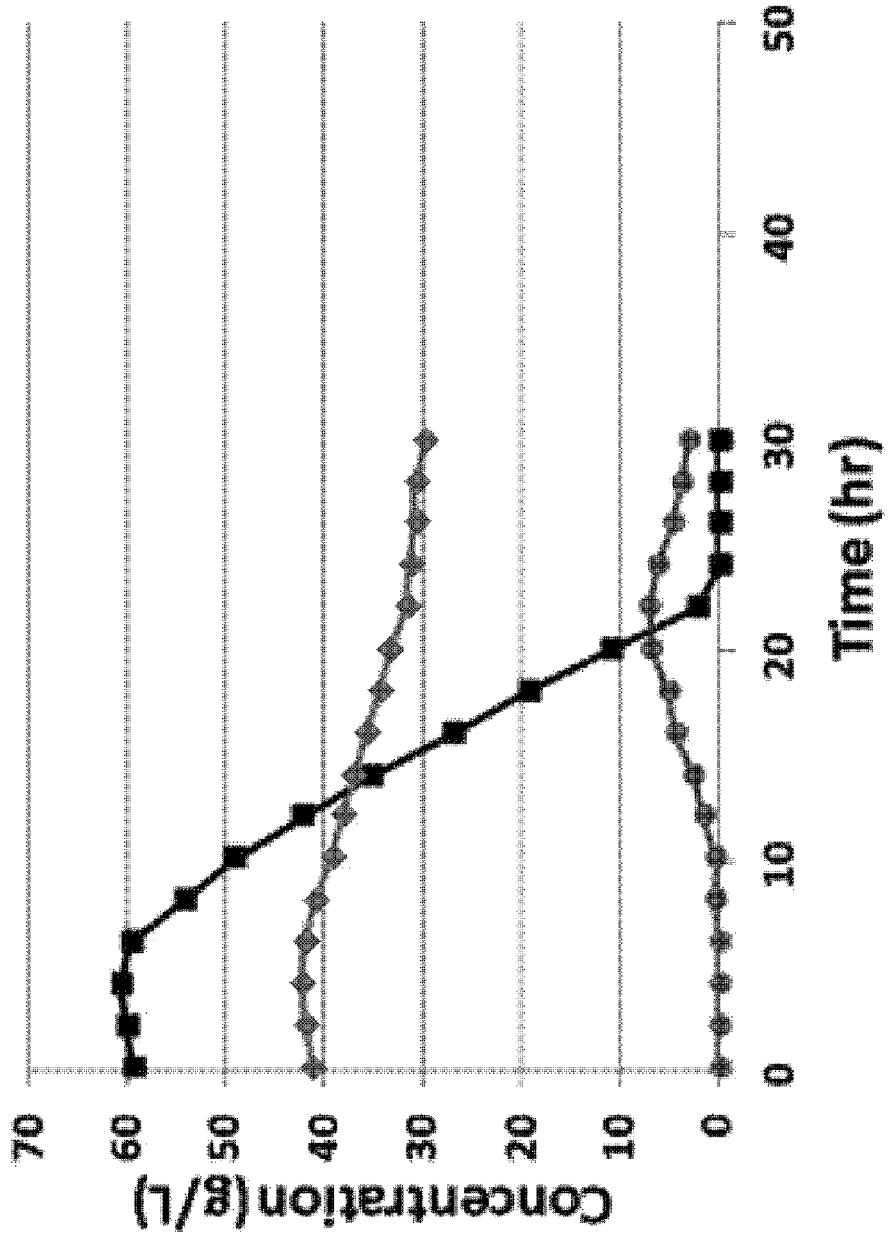
FIG. 4 shows simultaneous fermentation ability of glucose and xylose by a recombinant strain of Present Example 1.
Figure 5:
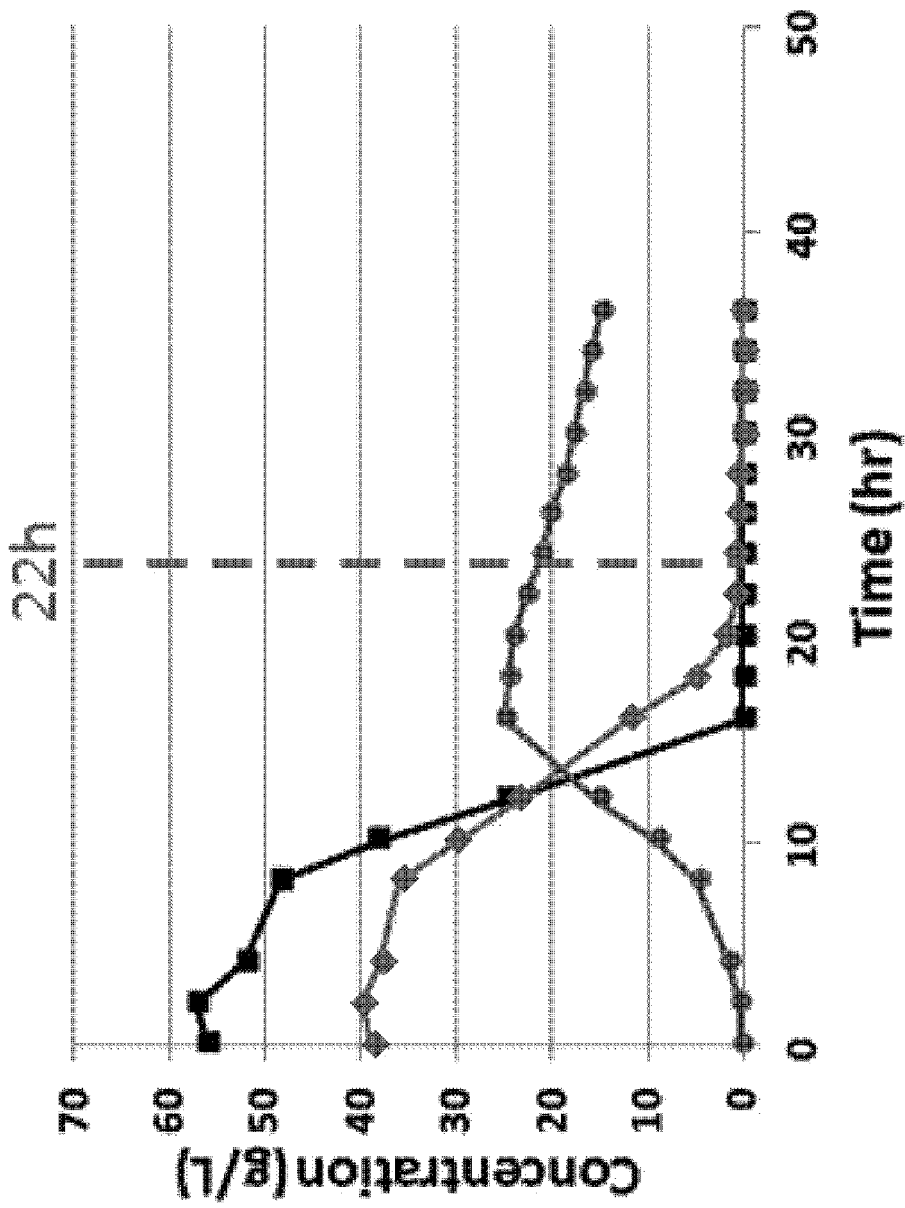
FIG. 5 shows simultaneous fermentation ability of glucose and xylose by a recombinant strain of Present Example 2.
Figure 6:
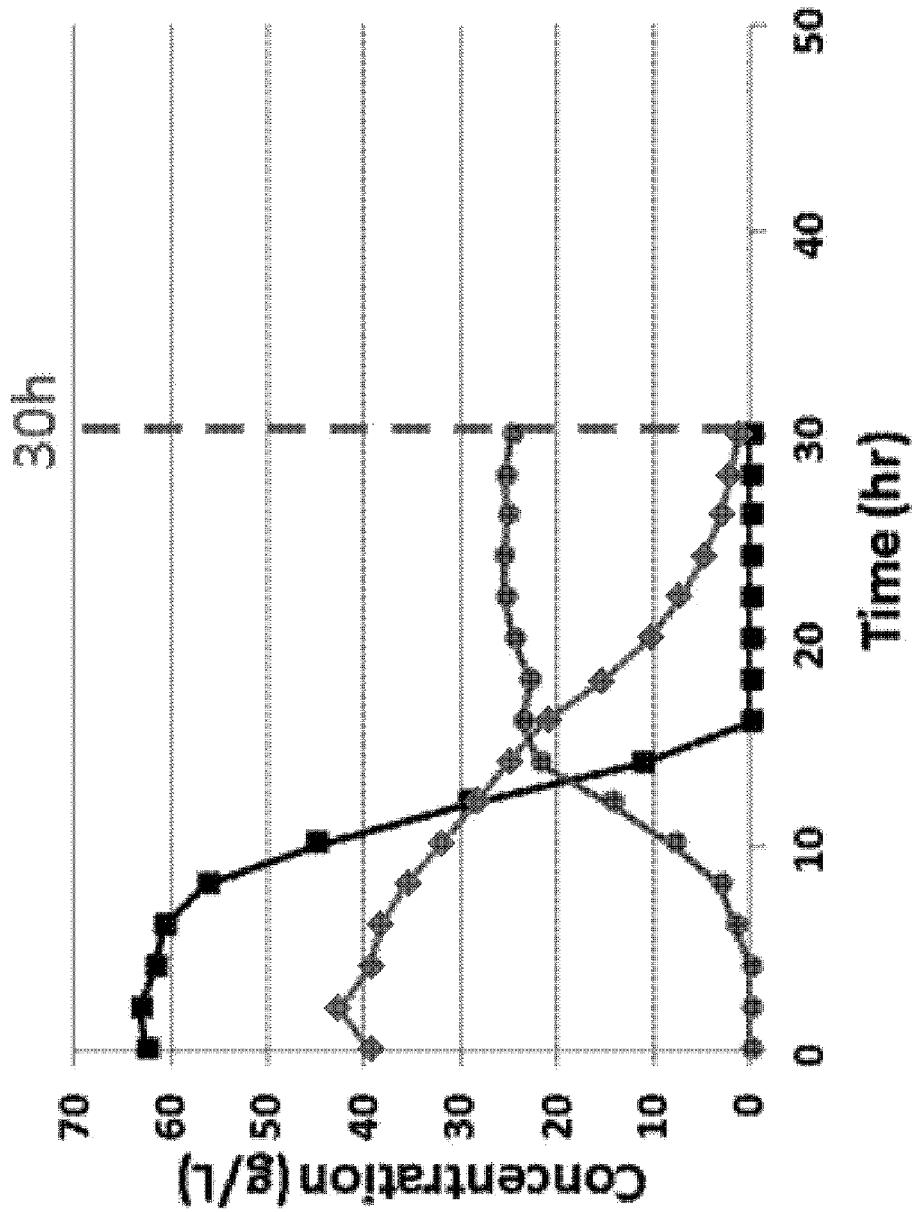
FIG. 6 shows simultaneous fermentation ability of glucose and xylose by a recombinant strain of Present Example 3.
Figure 7:
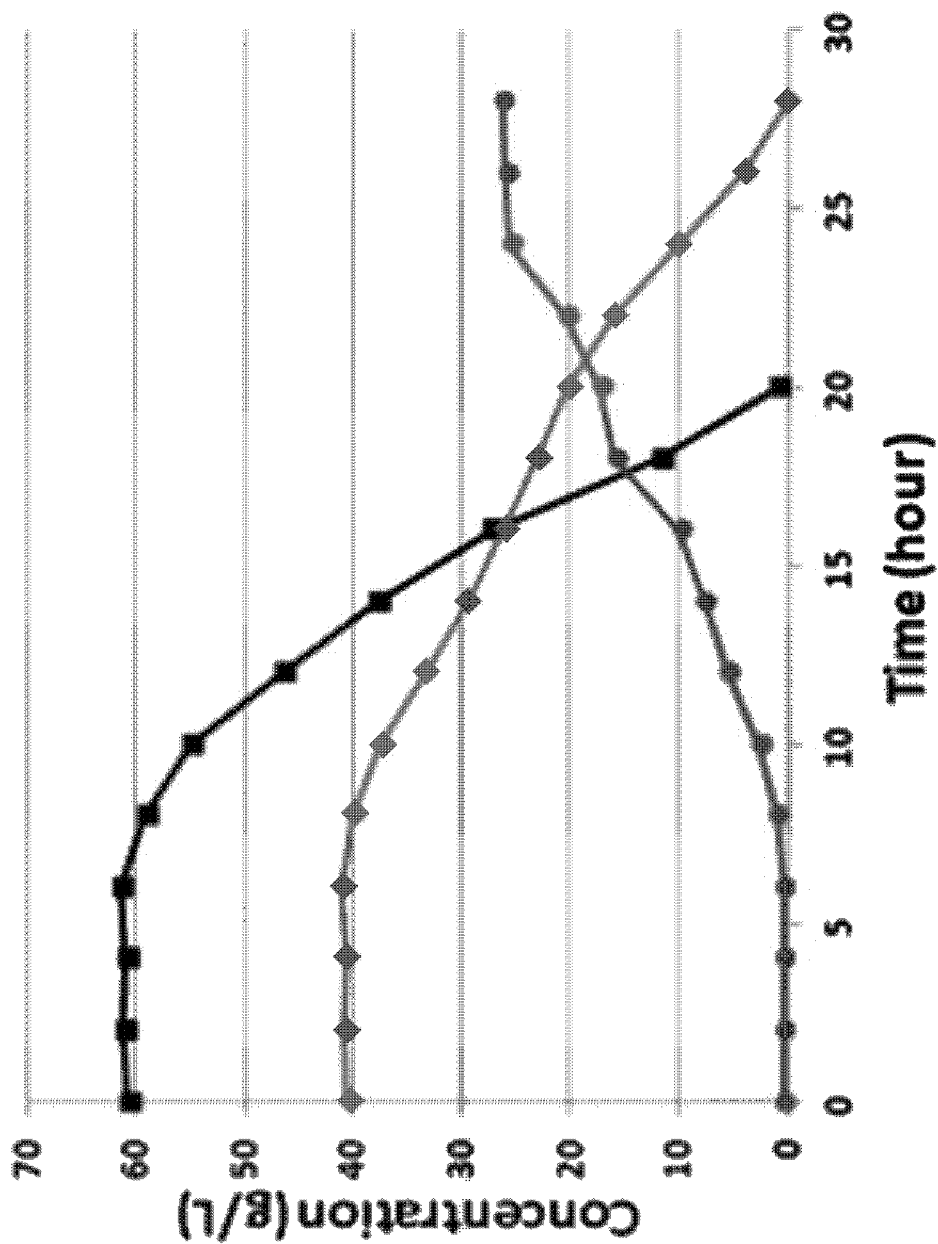
FIG. 7 shows simultaneous fermentation ability of glucose and xylose by a recombinant strain of Present Example 4.
Figure 8:
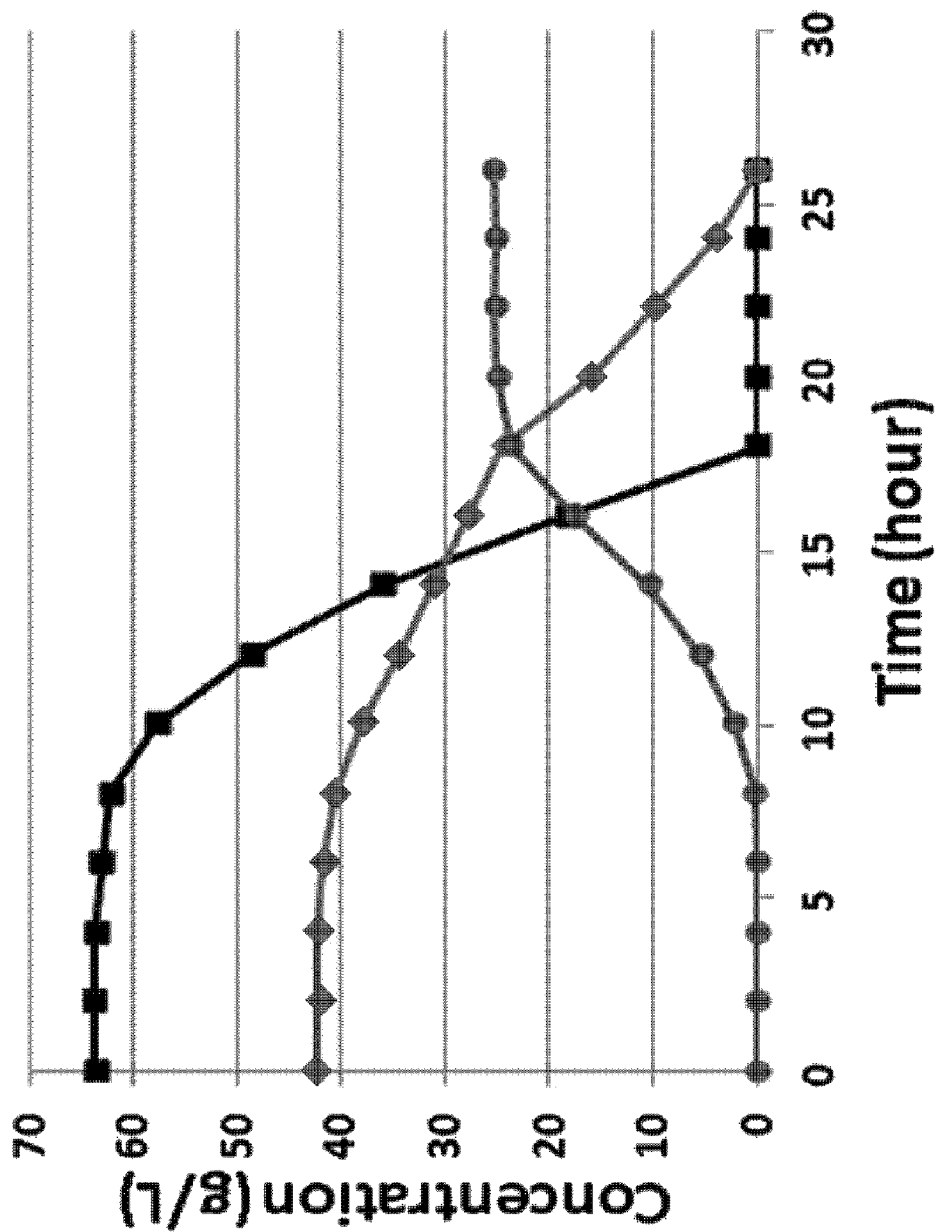
FIG. 8 shows simultaneous fermentation ability of glucose and xylose by a recombinant strain of Present Example 5.
Figure 9:
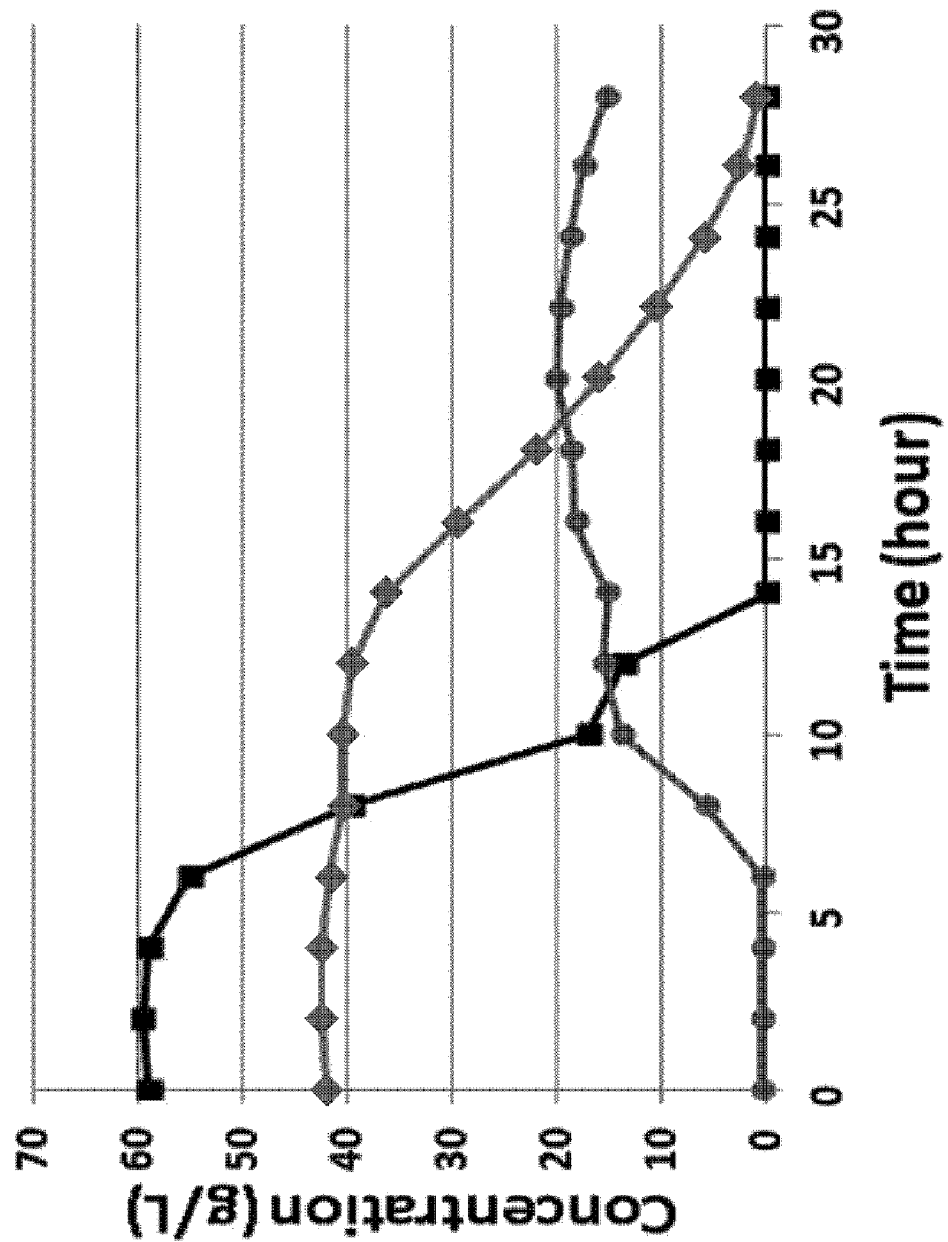
FIG. 9 shows simultaneous fermentation ability of glucose and xylose by a recombinant strain of Present Example 6.
Figure 10:
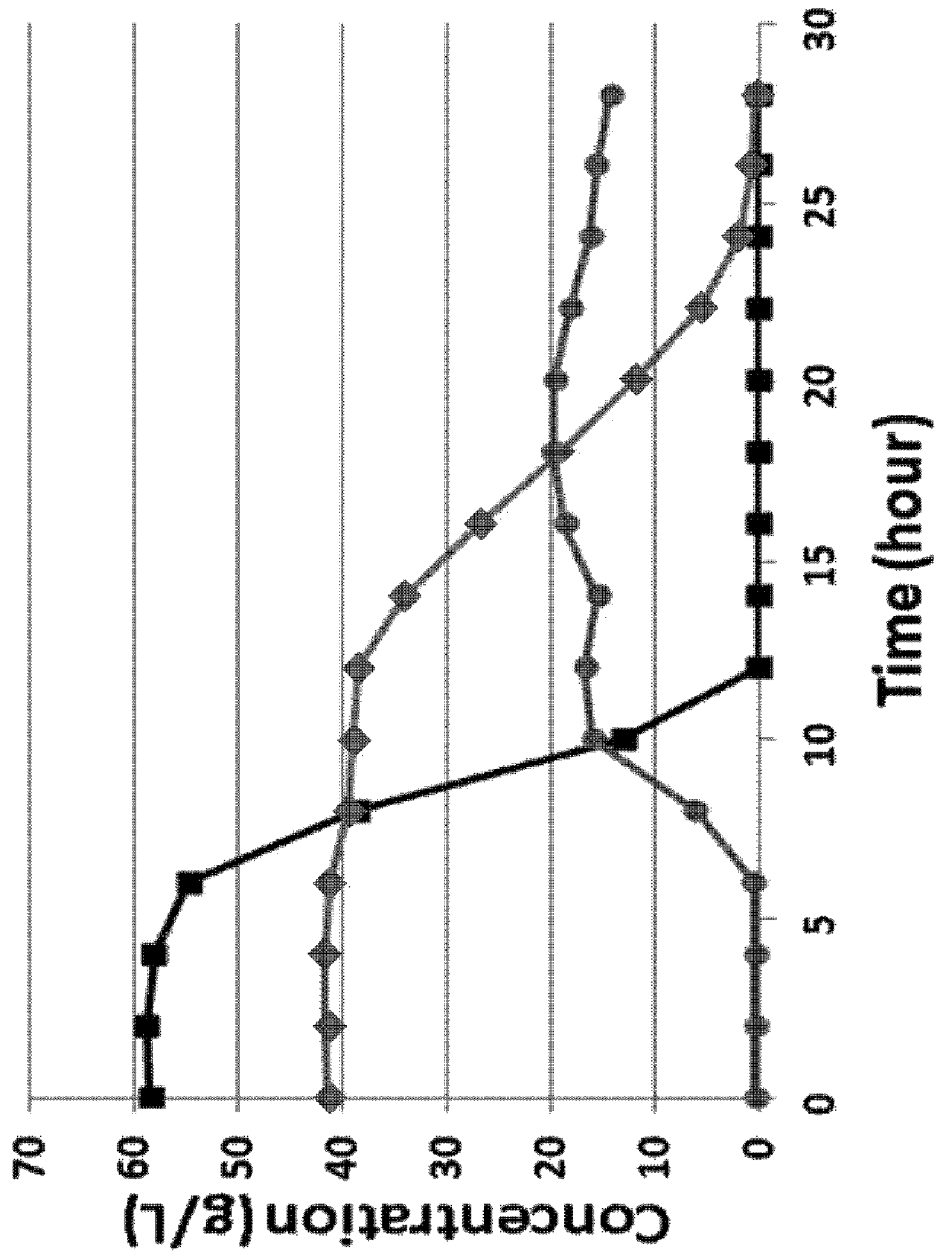
FIG. 10 shows simultaneous fermentation ability of glucose and xylose by a recombinant strain of Present Example 7.
Figure 11:
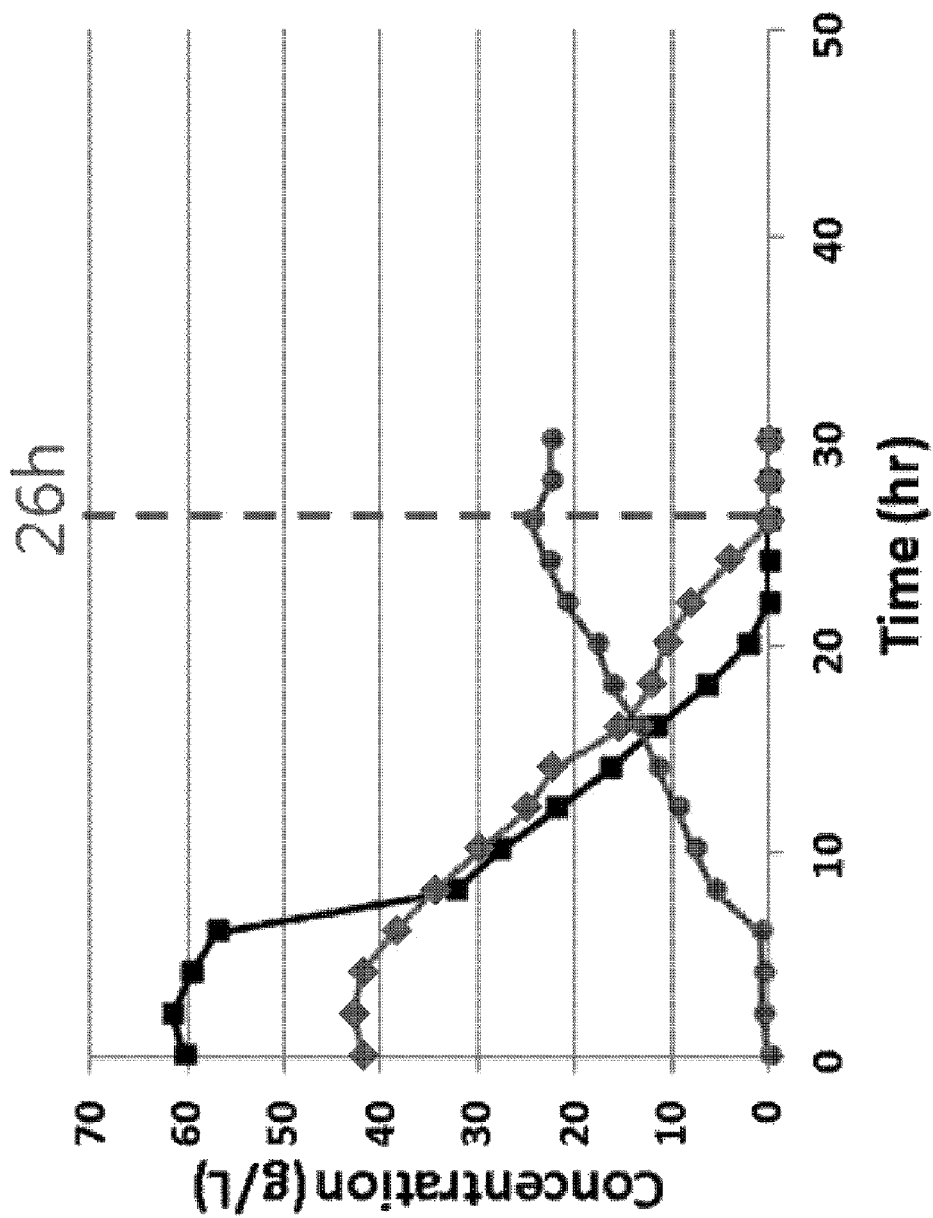
FIG. 11 shows simultaneous fermentation ability of glucose and xylose by a recombinant strain of Present Example 8.
Figure 12:
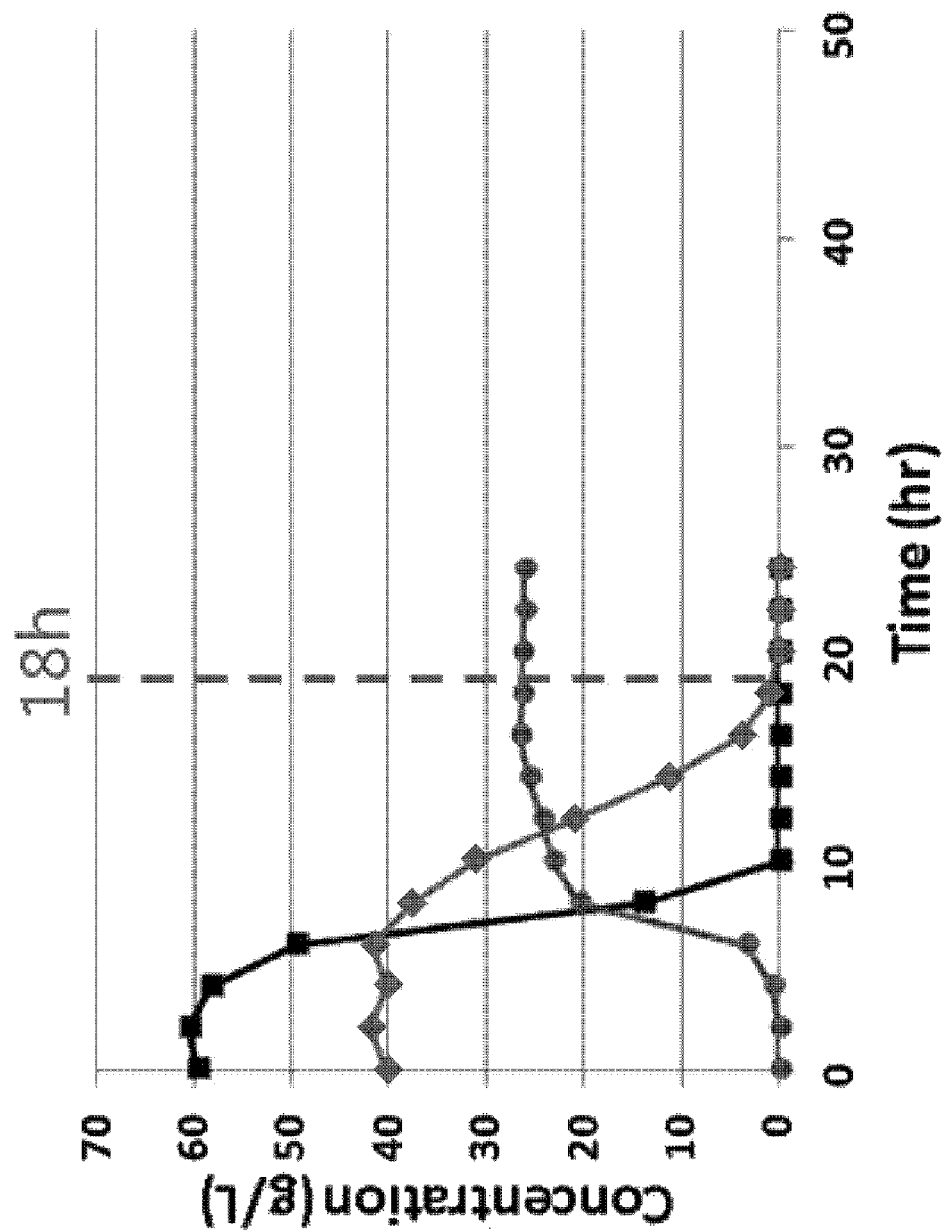
FIG. 12 shows simultaneous fermentation ability of glucose and xylose by a recombinant strain of Present Example 9.

As a result, the recombinant strains of Present Examples 1 to 9 were found to have excellent simultaneous fermentation ability of glucose and xylose. In detail, due to the catabolite repression, the wild-type strain metabolized the glucose and then metabolized the xylose. Thus, a fermentation time was found to be quite large (FIG. 2). Further, the strain of Comparative Example 1 was found to consume glucose and then consume xylose due to the catabolite repression mechanism (FIG. 3). However, the recombinant strains of Present Example 1 and Present Example 2 metabolized glucose and xylose simultaneously (FIG. 4: Present Example 1, FIG. 5: Present Example 2). In the recombinant strains of Present Examples 3 to 7, xylose metabolism-related genes were overexpressed to improve the consumption of xylose (FIG. 6: Present Example 3, FIG. 7: Present Example 4, FIG. 8: Present Example 5, FIG. 9: Present Example 6, FIG. 10: Present Example 7). The recombinant strains of Present Examples 8 and 9 also metabolized glucose and xylose at the same time. This may be due to the fact that the catabolite repression mechanism was inhibited due to overexpression of the mutated crp gene, resulting in simultaneous metabolism of glucose and xylose (FIG. 11: Present Example 8, FIG. 12: Present Example 9) (Table 11). Further, fermentation by-products of these strains are shown in Table 12 below.

TABLE 11

| strain(Klebsiella) | 2,3-butanediol concentration (g/L) | Yield (g/g total) | 2,3-butanediol productivity (g/L/h) | simultaneous fermentation ability of hexose and pentose |
|---|---|---|---|---|
| Wild-type | 3.0 | 0.04 | <0.1 | X |
| Comparative Example 1 | 20.9 | 0.20 | <0.4 | X |
| Present Example 1 | 7.1 | 0.11 | 0.3 | ○ |
| Present Example 2 | 24.9 | 0.30 | 1.6 | ○ |
| Present Example 3 | 25.5 | 0.27 | 1.5 | ○ |
| Present Example 4 | 26.2 | 0.26 | 1.1 | ○ |
| Present Example 5 | 25.3 | 0.24 | 1.3 | ○ |
| Present Example 6 | 20.0 | 0.24 | 1.0 | ○ |
| Present Example 7 | 19.7 | 0.24 | 1.1 | ○ |
| Present Example 8 | 24.5 | 0.24 | 1.0 | ○ |
| Present Example 9 | 26.2 | 0.26 | 1.3 | ○ |

TABLE 12

| Unit (g/L) | acetoin | ethanol | succinate | lactate | formate | acetate |
|---|---|---|---|---|---|---|
| Wild-type | 0 | 1.34 | 0.27 | 33.9 | 0.16 | 1.48 |
| Comparative Example 1 | 14.9 | 0.56 | 0.14 | 0.04 | 0.14 | 3.21 |
| Present Example 1 | 8.1 | 0 | 0.95 | 0.06 | 0.06 | 2.41 |
| Present Example 2 | 11.3 | 1.12 | 0.02 | 0.04 | 0.15 | 2.07 |
| Present Example 3 | 11.3 | 0.21 | 0 | 0.17 | 0.07 | 2.4 |
| Present Example 4 | 10.6 | 0.49 | 0 | 0.12 | 0 | 2.4 |
| Present Example 5 | 11.7 | 0 | 0 | 0.11 | 0.05 | 0.51 |
| Present Example 6 | 11.3 | 0.43 | 0.56 | 0.09 | 0.25 | 0.38 |
| Present Example 7 | 12.8 | 0.15 | 0.37 | 0.05 | 0.2 | 0.63 |
| Present Example 8 | 11.7 | 0.28 | 0.95 | 0.08 | 0.98 | 2.61 |
| Present Example 9 | 13.4 | 0.68 | 0 | 0 | 0.13 | 3.1 |

<Experimental Example 3> Evaluation of Simultaneous Fermentation Ability of Glucose and Xylose Based on Lignocellulosic Biomass Type The simultaneous fermentation ability of glucose and xylose by the recombinant strain according to the present disclosure based on the type of the lignocellulosic biomass and a sugar percentage in the hydrolysate was evaluated.

<3-1> Evaluation of Simultaneous Fermentation Ability of Glucose and Xylose when Using Simulated Liquid The simultaneous fermentation performance of glucose and xylose by the recombinant K. oxytoca of each of Comparative Example 1 and Present Example 3 in a batch fermentation using simulated liquid was evaluated. These strains were inoculated into 250 ml of a complex medium containing 9 g/L glucose (50 mM glucose) and were cultured for 16 hours at 37° C., and then the culture solution was inoculated into 3 L complex medium. The fermentation conditions were as follows: aerobic condition (micro-aerobic condition; aerobic speed 1 vvm, stirring speed 550 rpm), 60 g/L initial glucose concentration, 40 g/l, initial xylose concentration, pH 6.5, and culture temperature of 37° C. (glucose and xylose being mixed in a weight ratio of 6:4). For adjustment of pH during the fermentation, 5N NaOH was used. Each recombinant Klebsiella was sampled during the fermentation. A growth speed thereof was evaluated by measuring OD600 (optical density) of each of the collected samples. Each of the collected samples was centrifuged at 13,000 rpm for 10 minutes, and then metabolite and 2,3-butanediol concentration of a supernatant were analyzed using liquid chromatography (HPLC).

In this connection, the recombinant strain of Present Example 3 was cultured in the medium having 25 mg/L of chloramphenicol added thereto.

Figure 13:
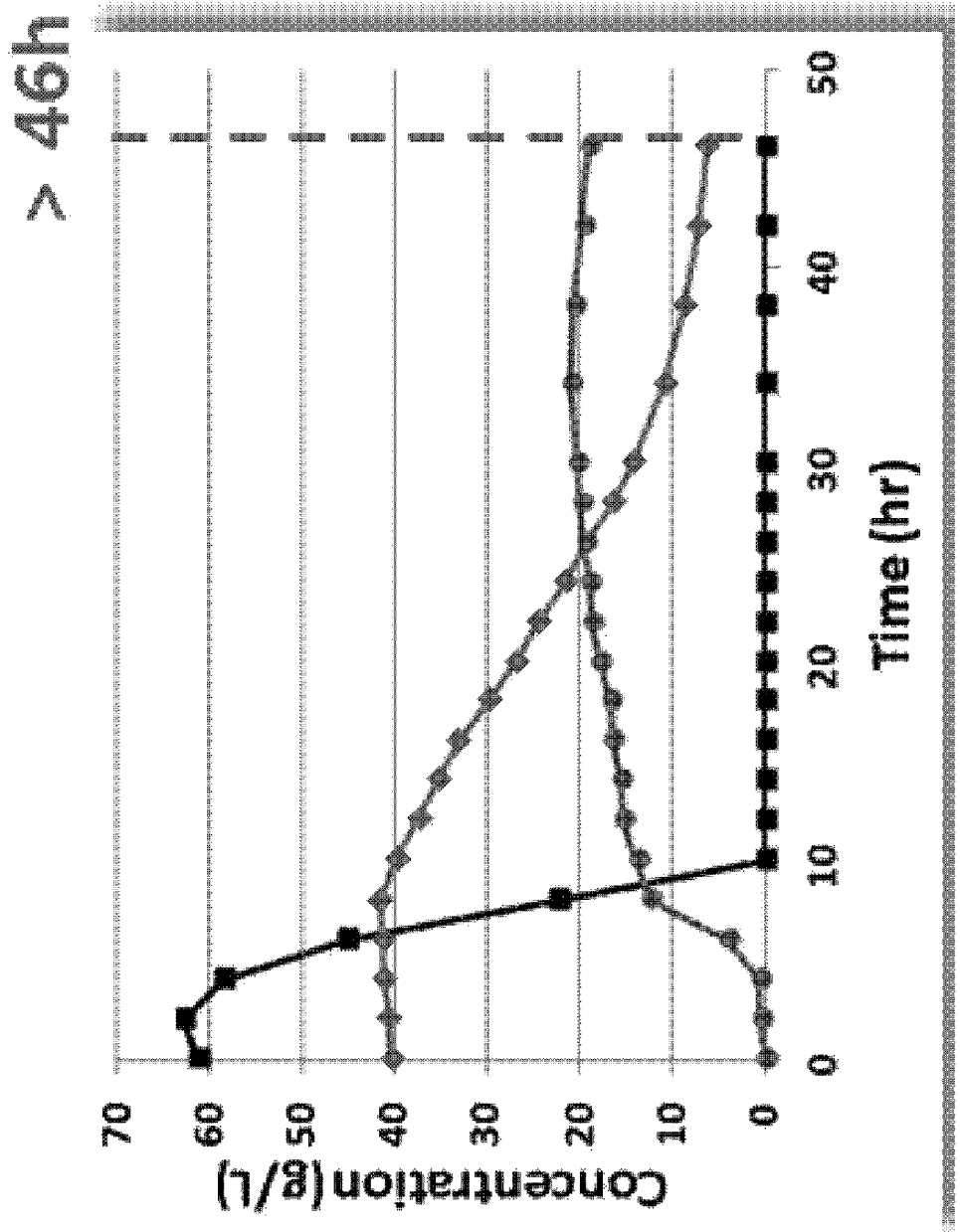
FIG. 13 shows a result of batch culture of a recombinant strain of Comparative Example 1 using simulated liquid.
Figure 14:
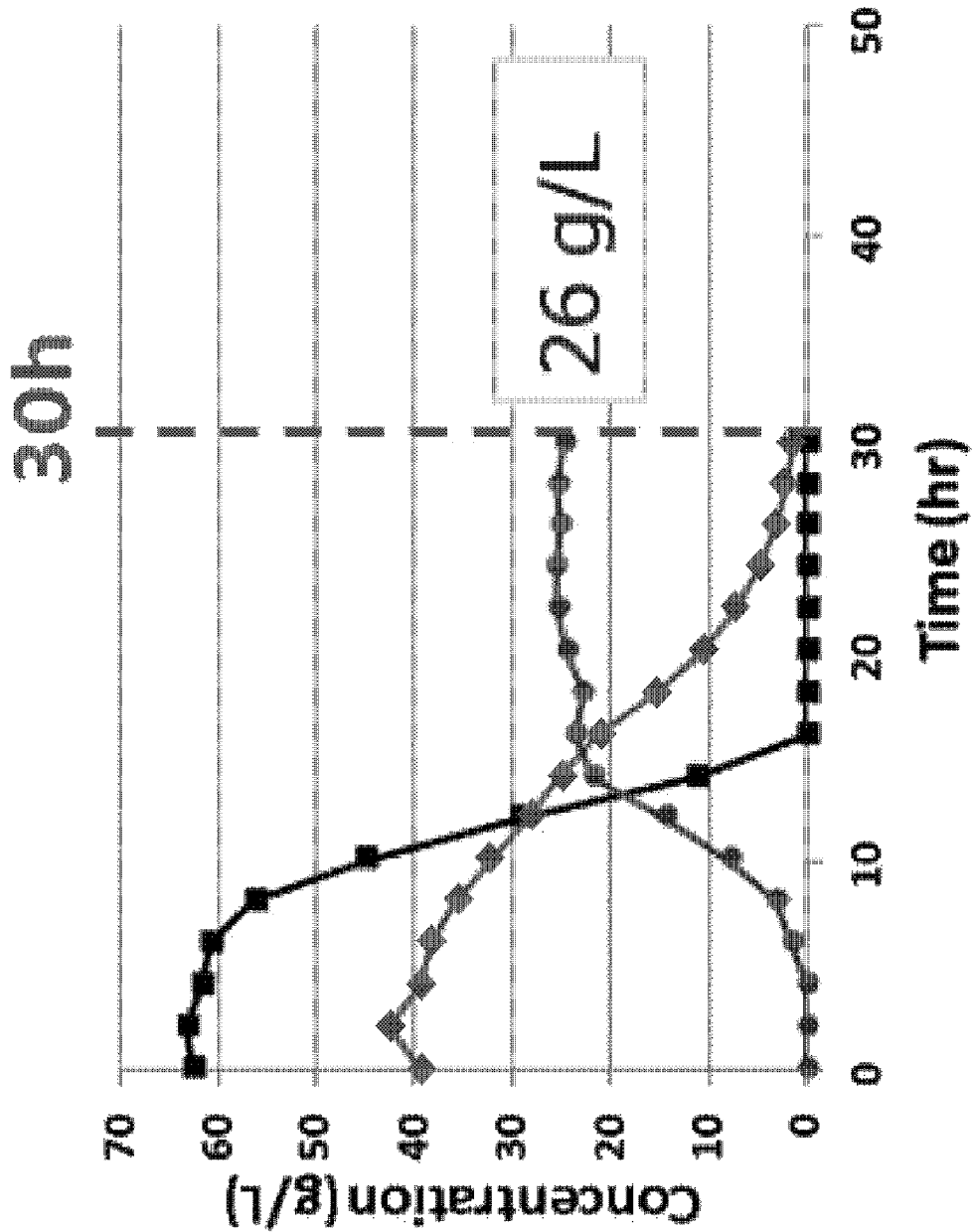
FIG. 14 shows a result of batch culture of a recombinant strain of Present Example 3 using simulated liquid.

As a result, it took more than 46 hours for the strain of Comparative Example 1 to have consumed both glucose and xylose (FIG. 13). To the contrary, it was identified that it took 30 hours for the strain of Present Example 3 to have consumed both glucose and xylose (FIG. 14), and thus the strain of Present Example 3 consumed the mixed sugars at high speed for metabolizing.

<3-2> Evaluation of Simultaneous Fermentation Ability of Glucose and Xylose when Using *Miscanthus sinensis*-Derived Hydrolysate The simultaneous fermentation performance of glucose and xylose by the recombinant *K. oxytoca* of each of Comparative Example 1 and Present Example 3 in a batch fermentation of lignocellulosic hydrolysate using *Miscanthus sinensis* was evaluated. These strains were inoculated into 250 ml of a complex medium containing 9 g/L glucose (50 mM glucose) and were cultured for 16 hours at 37° C., and then the culture solution was inoculated into 3 L complex medium. The fermentation conditions were as follows: aerobic condition (micro-aerobic condition; aerobic speed 1 vvm, stirring speed 550 rpm), 100 g/l, initial *Miscanthus sinensis*-derived sugar concentration, pH 6.5, culture temperature 37° C. (glucose and xylose were contained in a weight ratio of 7:3, 70 g/L glucose, 30 g/l, xylose). For adjustment of pH during the fermentation, 5N NaOH was used. Each recombinant *Klebsiella* was sampled during the fermentation. A growth speed thereof was evaluated by measuring OD600 (optical density) of each of the collected samples. Each of the collected samples was centrifuged at 13,000 rpm for 10 minutes, and then metabolite and 2,3-butanediol concentration of a supernatant were analyzed using liquid chromatography (HPLC).

Figure 15:
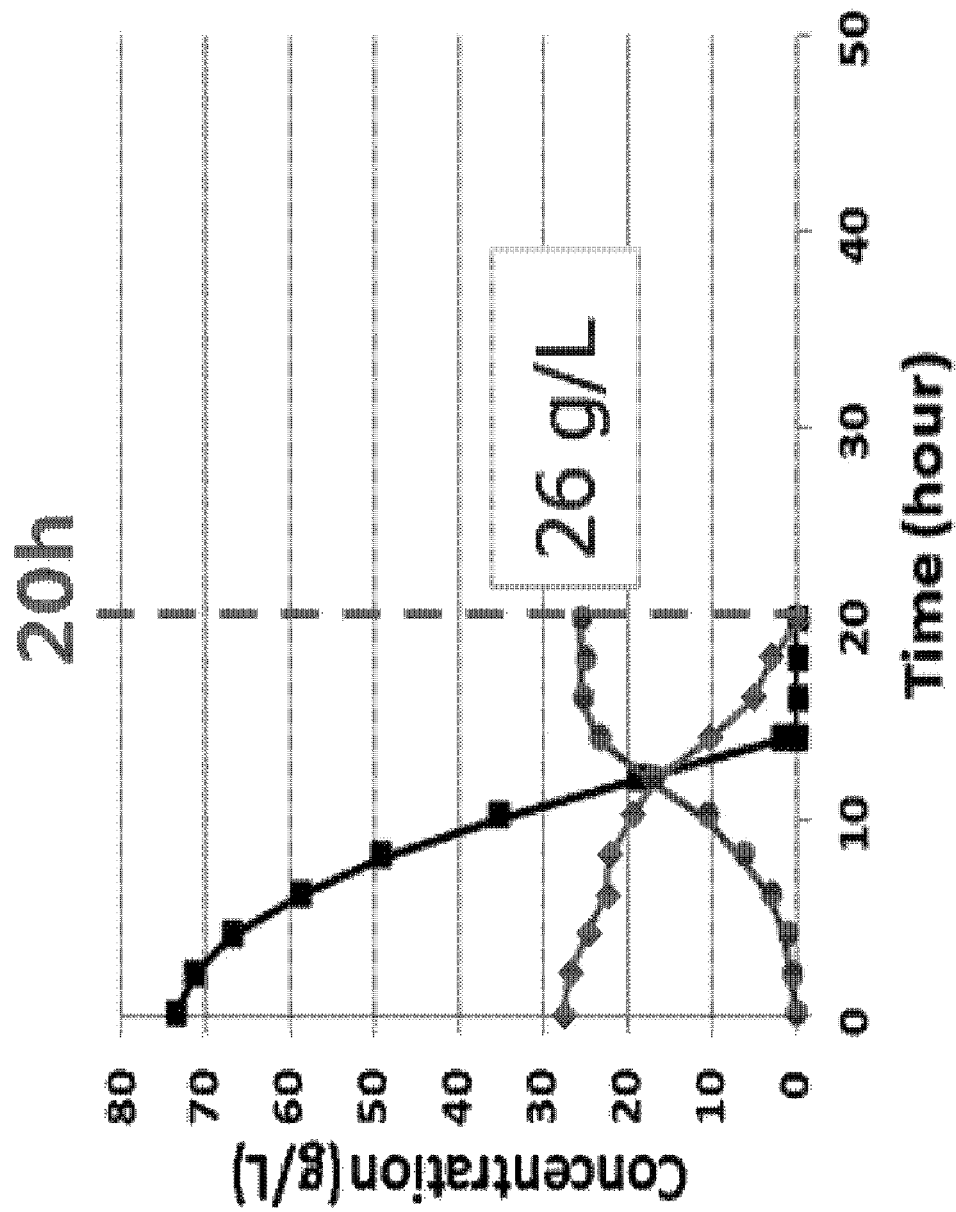
FIG. 15 shows a result of batch culture of a recombinant strain of Present Example 3 using *Miscanthus sinensis*-derived hydrolysate.

As a result, it was identified that it took 20 hours for the strain of Present Example 3 to have consumed both glucose and xylose (FIG. 15), and thus the strain of Present Example 3 consumed the mixed sugars at high speed for metabolizing.

<3-3> Evaluation of Simultaneous Fermentation Ability of Glucose and Xylose when Using Wood-Derived Hydrolysate The simultaneous fermentation performance of glucose and xylose by the recombinant *K. oxytoca* of each of Comparative Example 1 and Present Example 3 in a batch fermentation of lignocellulosic hydrolysate using wood was evaluated. These strains were inoculated into 250 ml of a complex medium containing 9 g/L glucose (50 mM glucose) and were cultured for 16 hours at 37° C., and then the culture solution was inoculated into 3 L complex medium. The fermentation conditions were as follows: aerobic condition (micro-aerobic condition; aerobic speed 1 vvm, stirring speed 550 rpm), 100 g/L initial wood-derived sugar concentration, pH 6.5, culture temperature 37° C. (glucose and xylose were contained in a weight ratio of 7:3, 70 g/L glucose, 30 g/L xylose). For adjustment of pH during the fermentation, 5N NaOH was used. Each recombinant *Klebsiella* was sampled during the fermentation. A growth speed thereof was evaluated by measuring OD600 (optical density) of each of the collected samples. Each of the collected samples was centrifuged at 13,000 rpm for 10 minutes, and then metabolite and 2,3-butanediol concentration of a supernatant were analyzed using liquid chromatography (HPLC).

Figure 16:
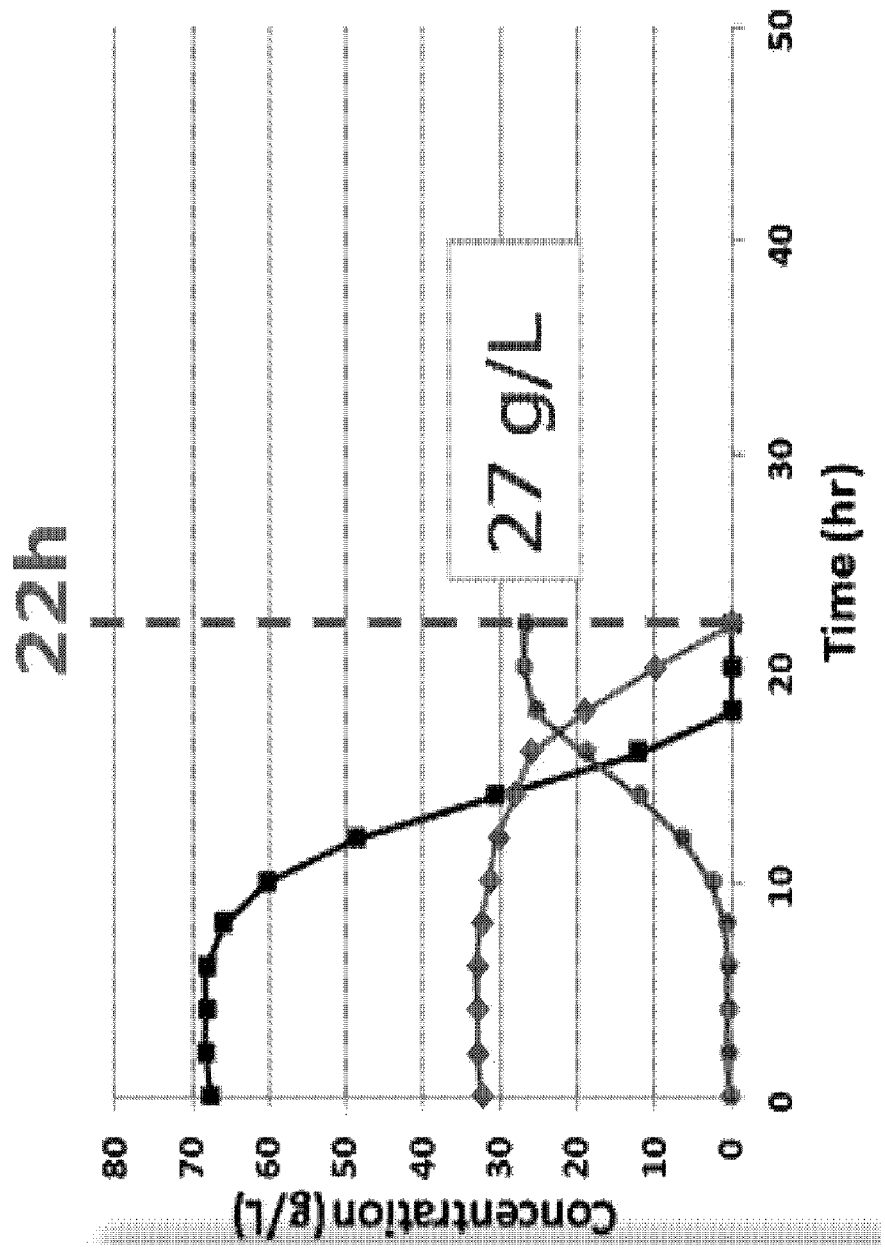
FIG. 16 shows a result of batch culture of a recombinant strain of Present Example 3 using wood-derived hydrolysate.

As a result, it was identified that it took 22 hours for the strain of Present Example 3 to have consumed both glucose and xylose (FIG. 16), and thus the strain of Present Example 3 consumed the mixed sugars at high speed for metabolizing.

<Experimental Example 4> Evaluation of Simultaneous Fermentation Ability of Glucose and Xylose in Fed-Batch Culture

<4-1> Fed-Batch Culture Using Simulated Liquid

The recombinant strains of Comparative Example 1 and Present Example 3 were fed-batch cultured using simulated liquid (glucose:xylose being mixed in a weight ratio of 6:4). Then, the simultaneous fermentation ability of glucose and xylose by the recombinant strains of Comparative Example 1 and Present Example 3 was evaluated. In this connection, a culture method was the same as in the <3-1> section, except that 50 g/L. of a mixture liquid of glucose and xylose was added as a feeding solution when a glucose or xylose concentration dropped to a level below 20 g/L.

Figure 17:
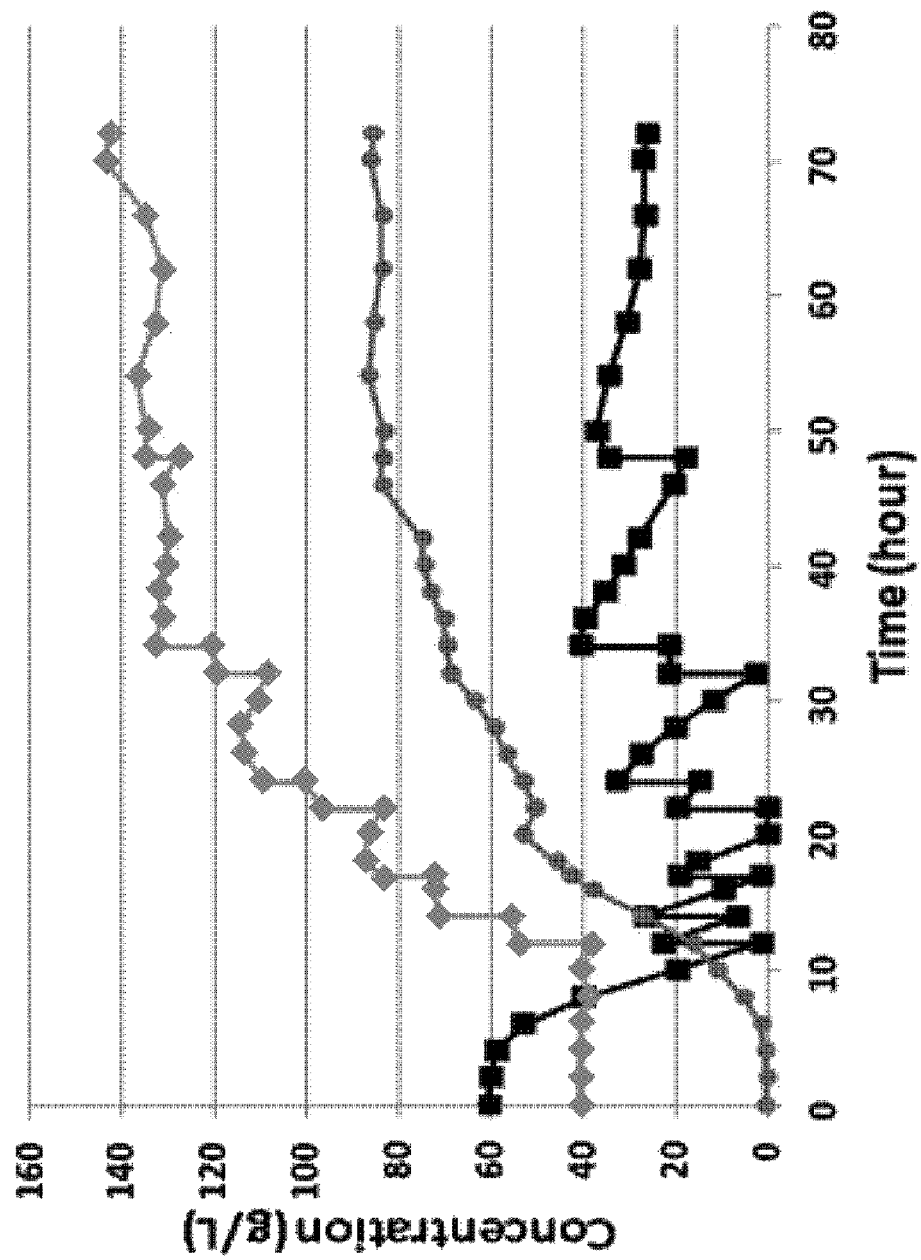
FIG. 17 shows a result of fed-batch culture of a recombinant strain of Comparative Example 1 using simulated liquid.
Figure 18:
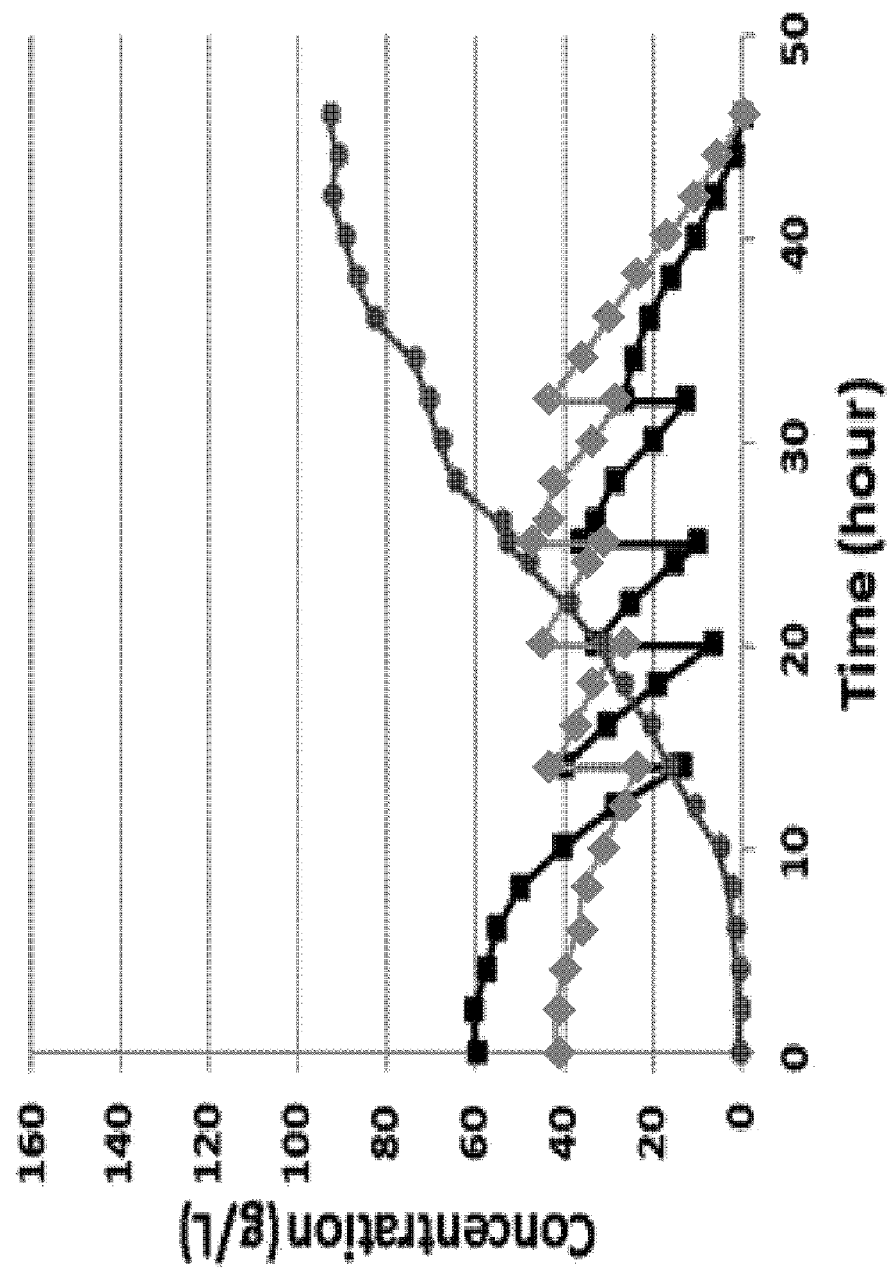
FIG. 18 shows a result of fed-batch culture of a recombinant strain of Present Example 3 using simulated liquid.

As a result, when using the recombinant strain of Comparative Example 1, xylose accumulated as a culture time elapsed. In 70 hours from the culture initiation, an amount of accumulated xylose was 140 g/L or greater. 2,3-butanedio production amount was 83.5 g/L. 2,3-butanedio productivity per hour was 1.67 g/L/h (FIG. 17). When using the recombinant strain of Present Example 3, 2,3-butanediol production amount was 93 g/L, and 2,3-butanediol productivity per hour was 2.02 g/L/h, and 2,3-butanediol yield was 40% (equal to 0.4 g 2,3-BDO/g total sugar amount). Xylose did not accumulate, and was consumed together with glucose (FIG. 18).

<4-2> Fed-Batch Culture Using Wood-Derived Hydrolysate

The recombinant strain of Present Example 3 was fed-batch cultured using wood-derived hydrolysate (glucose and xylose being contained in a weight ratio of 7:3). Then, the simultaneous fermentation ability of glucose and xylose by the recombinant strain of Present Example 3 was evaluated. In this connection, a culture method was the same as in the <3-3> section, except that 50 g/L of a mixture liquid of glucose and xylose was added as a feeding solution when a glucose or xylose concentration dropped to a level below 20 g/L.

Figure 19:
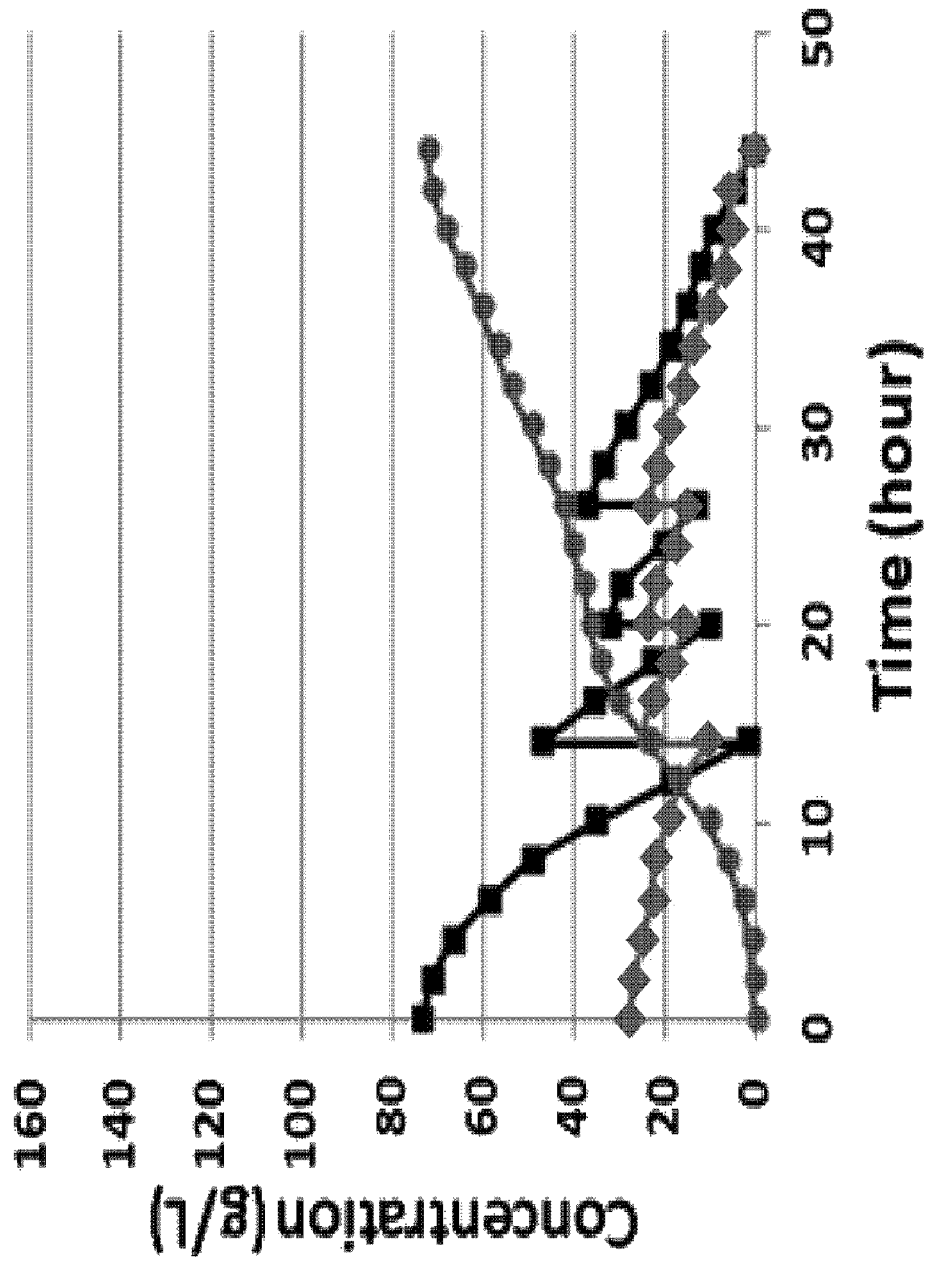
FIG. 19 shows a result of fed-batch culture of a recombinant strain of Present Example 3 using wood-derived hydrolysate.

When using the recombinant strain of Present Example 3, 2,3-butanediol production amount was 75 g/L, and 2,3-butanediol productivity per hour was 1.63 g/l h, and 2,3-butanediol yield was 40% (equal to 0.4 g 2,3-BDO/g total sugar amount). Xylose did not accumulate, and was consumed together with glucose (FIG. 19).

INDUSTRIAL AVAILABILITY

The present disclosure is directed to recombinant microorganisms having simultaneous fermentation ability of at least two sugars in lignocellulosic hydrolysate, and, further having diol production ability.

SEQUENCE LISTING FREE TEXT

SEQ ID NO: 1: nucleic acid sequence of homologous portion of ldhA.
SEQ ID NO: 2: nucleic acid sequence of homologous portion of pflB.
SEQ ID NO: 3: nucleic acid sequence of homologous portion of crr.
SEQ ID NO: 4: nucleic acid sequence of homologous portion of ptsG.
SEQ ID NO: 5: nucleic acid sequence of xylA.
SEQ ID NO: 6: nucleic acid sequence of xylB.
SEQ ID NO: 7: nucleic acid sequence of rpe.
SEQ ID NO: 8: nucleic acid sequence of rpiA.
SEQ ID NO: 9: nucleic acid sequence of talB.
SEQ ID NO: 10: nucleic acid sequence of tktA.
SEQ ID NO: 11: nucleic acid sequence of tktB.
SEQ ID NO: 12: nucleic acid sequence of tktAB.
SEQ ID NO: 13: nucleic acid sequence of crp(in)01.
SEQ ID NO: 14: nucleic acid sequence of crp(in)02.

DEPOSITION INFORMATION

Depository name: Korea Research Institute of Bioscience and Biotechnology
Accession number: KCTC12132BP
Date of Deposit: 20120208

---

What is claimed is:

1. A recombinant *Klebsiella* having simultaneous fermentation ability of glucose and xylose and ability to produce 2,3-butanediol, the recombinant *Klebsiella* is transformed to have a deletion of an ldhA gene having the nucleic acid of SEQ ID NO: 1 and a deletion of a pflB gene having the nucleic acid of SEQ ID NO: 2; and transformed to have a deletion of a crr gene having the nucleic acid of SEQ ID NO:3, and/or a deletion of a ptsG gene having the nucleic acid of SEQ ID NO: 4; and transformed to overexpress a plasmid comprising a xylA gene having the nucleic acid of SEQ ID NO: 5 and a xylE gene having the nucleic acid of SEQ ID NO: 6; overexpress a plasmid comprising a rpe gene having the nucleic acid of SEQ ID NO: 7; overexpress a plasmid comprising a rpiA gene having the nucleic acid of SEQ ID NO: 8; overexpress a plasmid comprising a talE gene having the nucleic acid of SEQ ID NO: 9; overexpress a plasmid comprising a tktAB gene having the nucleic acid of SEQ ID NO: 12; overexpress a plasmid comprising a crp(in)01 gene having the nucleic acid of SEQ ID NO: 13; and/or overexpress a plasmid comprising a crp(in)02 gene having the nucleic acid of SEQ ID NO: 14.

2. The recombinant microorganism of claim 1, wherein recombinant microorganism incorporates a gene according to SEQ ID NO. 13 for increasing inhibition of a catabolite repression mechanism when compared with the inhibition of the catabolite repression mechanism exhibited in the wild-type microorganism.

3. The recombinant microorganism of claim 1, wherein the recombinant microorganism has enhanced activity of at least one enzyme selected from a group consisting of xylose isomerase, xylulokinase, D-ribulose-5-phosphate 3-epimerase, ribose 5-phosphate isomerase, transaldolase, and transketolase.

4. The recombinant microorganism of claim 1, wherein the recombinant microorganism has inhibited activity of a receptor protein of cyclic adenosine monophosphate (cAMP).

5. The recombinant microorganism of claim 1, wherein the recombinant microorganism has a mutation in crp which is a gene for encoding a cAMP-activated global transcription factor.

6. A method for producing diols, the method comprising:
    preparing a medium comprising glucose and xylose;
    inoculating the recombinant microorganism of claim 1 to the medium; and
    culturing the recombinant microorganism.

7. The method of claim 6, wherein the medium comprises lignocellulosic hydrolysate.

* * * * *

```
                     SEQUENCE LISTING

<160> NUMBER OF SEQ ID NOS: 14

<210> SEQ ID NO 1
<211> LENGTH: 990
<212> TYPE: DNA
<213> ORGANISM: Klebsiella oxytoca

<400> SEQUENCE: 1
atgaaaatcg ctgtgtatag tacaaaacag tacgacaaga agtatctgca gcatgttaat      60
gatgcatatg gctttgaact ggagtttttt gacttcctgc taaccgaaaa aaccgccaaa     120
accgccaacg gctgtgaagc ggtgtgtatc ttcgtaaacg atgacggtag ccgcccggta     180
cttgaagaac tgaaagccca cggcgtgcag tacatcgcgc tgcgctgcgc ggggttcaac     240
aacgttgacc tcgatgccgc caaagagctg ggcctgcggg tggtgcgcgt cccggcctac     300
tcgccggaag cggtcgctga gcacgcgatc ggcatgatga tgtcgctgaa ccgccgcatt     360
caccgtgcct atcagcgcac ccgcgacgcg aacttctctc tggaagggct gaccggtttc     420
accatgcacg gtaaaaccgc cggcgttatt ggcaccggta aaatcggcgt cgccgcgctg     480
cgcattctta aaggcttcgg tatgcgtctg ctggcgtttg atccctaccc aagcgccgcc     540
gcgctggata tgggcgtgga gtatgtcgat cttgaaaccc tgtaccggga gtccgatgtt     600
atctcactgc actgcccact gaccgatgaa aactaccatt tgctgaacca tgccgcgttc     660
gatcgcatga agacgggggt gatgatcatc aacaccagcc gcggcgcgct catcgattcg     720
caggcagcga tcgacgccct gaagcatcag aaaattggcg cgctggggat ggacgtgtat     780
gagaacgaac gcgatctgtt ctttgaagat aagtctaatg acgtgattca ggatgatgtg     840
ttccgccgtc tctccgcctg ccataacgtc ctgtttaccg gtcaccaggc gtttctgacc     900
gcggaagcgt tgatcagcat ttcgcaaacc accctcgaca acctgcgtca agtggatgca     960
ggcgaaacct gtcctaacgc actggtctga                                     990

<210> SEQ ID NO 2
<211> LENGTH: 2283
<212> TYPE: DNA
<213> ORGANISM: Klebsiella oxytoca

<400> SEQUENCE: 2
atgtccgagc ttaatgaaaa gttagccaca gcctgggaag ttttgcgaa aggtgactgg      60 cagaacgaag tcaacgtccg cgacttcatc cagaaaaact ataccccgta cgaaggtgac     120
gagtccttcc tggctggcgc aactgacgcg accaccaagc tgtgggacac cgtaatggaa     180
ggcgttaaac aggaaaaccg cactcacgcg cctgttgatt ttgatacttc ccttgcatcc     240
accatcactt ctcatgacgc tggctacatc gagaaaggtc tcgagaaaat cgttggtctg     300
cagactgaag ctccgctgaa acgcgcgatt atcccgttcg gcggcatcaa aatggtcgaa     360
ggttcctgca aagcgtacga tcgcgagctg gacccgatgc tgaagaaaat cttcactgaa     420
taccgtaaaa ctcacaacca gggcgtgttt gacgtttaca ccaaagacat cctgaactgc     480
cgtaaatctg gtgttctgac cggtctgccg gatgcctatg gcgtggtcg tatcatcggt     540 gactaccgtc gcgttgcgct gtacggtatc gacttcctga tgaaagacaa atacgctcag     600
```

```
ttcgtttctc tgcaagagaa actggaaaac ggcgaagatc tggaagcaac catccgtctg    660
cgcgaagaaa tctctgaaca gcaccgcgcg ctgggtcaga tcaaagaaat ggcggctaaa    720
tatggctgcg atatctctgg tcctgctacc accgctcagg aagctatcca gtggacctac    780
ttcggttacc tggctgccgt aaaatctcag aacggcgcgg caatgtcctt cggtcgtacc    840
tccagcttcc tggacatctt catcgaacgt gacctgaaag ccggtaaaat caccgagcaa    900
gacgcacagg aaatgattga ccacctggtc atgaaactgc gtatggttcg tttcctgcgt    960 accccctgaat atgatgaact gttctctggc gacccgatct gggcaacaga atctatcggc   1020
ggtatgggcg ttgacggccg tactctggtc accaaaaaca gcttccgttt cctgaacacc   1080
ctgtacacca tggggccgtc tccggagccg aacatcacca ttctgtggtc tgaaaaactg   1140
ccgctgagct tcaaaaaata cgccgcgaaa gtgtccatcg atacctcttc tctgcagtac   1200
gagaacgatg acctgatgcg tcctgacttc aacaacgatg actacgctat cgcttgctgc   1260
gtaagcccga tggttgttgg taagcaaatg cagttcttcg gcgcgcgtgc taacctggcg   1320
aaaaccatgc tgtacgcaat caacggcggc gttgatgaaa actgaaaat gcaggttggt   1380 cctaaatctg aaccgatcaa aggcgacgtt ctgaacttcg acgaagtgat ggaccgcatg   1440
gatcacttca tggactggct ggctaaacag tacgtcactg cgctgaacat catccactac   1500
atgcacgaca gtacagcta cgaagcttcc ctgatggcgc tgcacgaccg tgatgttatc   1560
cgcaccatgg catgtggtat cgcaggtctt tccgttgcgg ctgactccct gtctgcaatc   1620
aaatatgcga agttaaacc gattcgtgac gaaaacggtc tggctgtcga cttcgaaatc   1680
gaaggcgaat cccgcagtt tggtaacaac gactctcgcg tcgatgatat ggccgttgac   1740
ctggttgaac gtttcatgaa gaaaattcag aaactgcaca cctaccgcaa cgctatcccg   1800
actcagtccg ttctgaccat cacctctaac gttgtgtatg gtaagaaaac cggcaacacc   1860
cctgacggtc gtcgcgctgg cgctccgttc ggaccaggtg ctaacccgat gcacggccgt   1920
gaccagaaag gcgctgttgc ctctctgacc tccgttgcaa aactgccgtt tgcttacgcg   1980
aaagatggta tttcttacac cttctctatc gtgccgaacg cgctgggtaa agacgacgaa   2040
gttcgtaaaa ctaacctcgc cggcctgatg gatggttact ccaccacga gcgtccatc    2100 gaaggcggtc agcatctgaa cgtcaacgtt atgaaccgcg aaatgctgct cgacgcgatg   2160
gaaaacccgg aaaaatatcc gcagctgacc atccgcgtat ccggctacgc agtacgtttt   2220
aactccctga ctaaagaaca gcagcaggac gttattactc gtaccttcac tcagaccatg   2280
taa                                                                 2283
```

<210> SEQ ID NO 3
<211> LENGTH: 510
<212> TYPE: DNA
<213> ORGANISM: Klebsiella oxytoca

<400> SEQUENCE: 3

```
atgggtttgt tcgataaatt gaaatctctg gtttctgatg acaaaaaaga caccggaact     60
attgagattg ttgccccgct ctctggcgag atcgtcaaca ttgaagacgt gccggatgta    120
gttttcgcgg aaaaaattgt gggtgatggc attgctatca aacctactgg caacaaaatg    180
gttgcgccgg tagatggtac catcggtaaa atttttgaaa ccaaccatgc ttttttcaatc    240 gaatctgata gcggcattga actgttcgtt cacttcggta ttgataccgt tgaactgaaa    300
ggcgaaggct tcaaacgtat cgctgaagaa ggccagcgcg tgaaagtcgg cgacccggtt    360
```

| | |
|---|---:|
| atcgaattcg atctgccgct gctggaagag aaagccaagt ctaccctgac tccggttgtt | 420 |
| atctccaaca tggacgagat caaagagctg atcaaactgt ccggtagcgt aaccgtgggt | 480 |
| gaaactccgg ttatccgcat caagaagtaa | 510 |

<210> SEQ ID NO 4
<211> LENGTH: 1434
<212> TYPE: DNA
<213> ORGANISM: Klebsiella oxytoca

<400> SEQUENCE: 4

| | |
|---|---:|
| atgtttaaga atgcatttgc taacctgcag aaggtcggta atcgctgat gctgccggta | 60 |
| tccgtactgc ctatcgcagg tatcctgctg ggcgtcggtt ccgcaaactt cagctggctg | 120 |
| ccagccgtag tttcccacgt catggcgaa gcgggcggtt cggtcttcgc taacatgccg | 180 |
| ctgatctttg ctatcggtgt cgcacttggc ttcactaaca acgacggcgt atccgctctg | 240 |
| gcatcggtcg tcgcttacgg catcatggtg aaaaccatgt ccgtggttgc acctctggtc | 300 |
| ctgcatttac ctgctgaaga gattgcggct aaacacctgg cggatactgg cgtactcggc | 360 |
| ggtattatct ccggtgccat cgcagcgtac atgttcaacc gcttctaccg catcaaattg | 420 |
| cctgagtatc tgggcttctt tgcgggcaag cgttttgtgc aattatctc cggtctggca | 480 |
| gcgatcttca ctggtgtgat cctgtccttt atctggccgc cgatcggtac cgcaatccag | 540 |
| actttctccc agtgggctgc ttaccagaac ccggttgtgg cgttcggtat ctacggcttc | 600 |
| attgaacgct gcctggtgcc gtttggtctg caccacatct ggaacgttcc tttccagatg | 660 |
| cagattggtg aatacaccaa cgcagccggt caggtcttcc acggcgatat ccgcgctac | 720 |
| atggcaggcg acccgaccgc gggcaaactg tccggcggct tcctgttcaa aatgtacggt | 780 |
| ctgccggccg ctgctatcgc tatctggcac tctgctaaac agaaaaccg cgcaaaagtg | 840 |
| ggcggtatca tgatctccgc agcgctgacc tcgttcctga ccggtatcac cgagccgatc | 900 |
| gagttctcct ttatgttcgt tgcgccgatc ctgtacgtta ccatgcgat ctggcaggc | 960 |
| ctggccttcc cgatctgtat cctgctgggt atgcgtgacg gtacttcgtt ctctcatggt | 1020 |
| ctgatcgact tcatcgtact gtccggcaac agcagcaaac tgtggctgtt cccgatagtc | 1080 |
| ggcatctgct atgcgatcgt ttactacgtg gtgttccgcg ttctgatcaa agcgctggat | 1140 |
| ctgaaaaccc cggtcgtga agatgcaacc gaagacagca agctggcgc caccagcgaa | 1200 |
| atggctccgg cactgattgc cgctttcggc ggtaaagaga acattactaa ccttgacgca | 1260 |
| tgtatcaccc gtctgcgcgt gagcgtagcg gatgtggcga agttgatca ggctggcctg | 1320 |
| aaaaaactgg gtgccgcagg cgtggttgtt gcaggttcag gcgttcaggc tattttcggt | 1380 |
| accaaatccg ataacctgaa aactgaaatg gatgaataca tccgcagcaa ctaa | 1434 |

<210> SEQ ID NO 5
<211> LENGTH: 1323
<212> TYPE: DNA
<213> ORGANISM: Klebsiella oxytoca

<400> SEQUENCE: 5

| | |
|---|---:|
| atgcagacct attttgacca gctcgatcgc gttcgttatg aaggcccgaa atccgctaac | 60 |
| ccactggctt tccgtcatta caacccggat gagctggtgc tgggcaaacg gatggaagac | 120 |
| catttacgct ttgcggcctg ctactggcac accttctgct ggaacggtgc cgatatgttc | 180 |
| ggcgtgggct cctttaaccg cccgtggcag cagccgggtg aagcaatgga aatggcgaaa | 240 |
| cgtaaagccg atgtcgcttt tgagtttttc cataaactga cgtaccgta ctactgcttc | 300 |

```
cacgacgtcg acgtttctcc tgaaggggca tcgctgaaag agtatgccaa taacttcgca    360
caaatggttg atgtgcttgc ggaaaaacag cagcaaagcg gcgtcaagct gctgtggggc    420
acggcaaact gctttacgaa cccgcgttac ggcgccggtg cggcaaccaa tccggatccg    480
gaagtgttca gctgggcggc gacccaggtg gtgaccgcga tggatgcgac ccacaaactg    540
ggcggtgaaa actacgtcct gtgggcggt cgcgaaggct atgaaaccct gctgaacacc    600
gacctgcgtc aggaacgcga gcagattggc cgcttcatgc agctggtcgt ggagcataaa    660
cataaaatcg gcttccaggg tacgctactg attgaaccga accgcagga gcccaccaag    720 catcagtacg attacgacgc gtctaccgtc tacggcttcc tgaaacagtt cggcctggaa    780
aaagagatca agctgaatat cgaagcgaac cacgcgacgc tggccggcca cacgttccac    840
cacgaaattg ctaccgccat cgccctcggc ctgtttggtt ccgttgacgc taaccgcggc    900
gacccgcagc tgggctggga tactgaccag ttcccgaaca gcgttgaaga gaacgcgctt    960
gtgatgtacg aaatccttaa agcgggcggc ttcaccaccg gcggcctgaa ctttgatgct   1020
aaagtgcgtc gtcagagcac cgacaaatac gacctgttct acggccacat cggtgcgatg   1080
gacaccatgg cgctggcgct gaaagtcgct gcccgtatga ttgaaggcgg cgagctggat   1140
aaacgcgttg ccaaacgcta tgccggctgg aacggcgagc tgggtcagca gatcctcaaa   1200
ggccagatga acctggcgga catcgcccag tatgccactc agcataacct ggcgccgcag   1260
caccagagcg gccatcagga actgcttgaa aacgtggtta accgctacct ctttgatcgc   1320
tga                                                                 1323

<210> SEQ ID NO 6
<211> LENGTH: 1455
<212> TYPE: DNA
<213> ORGANISM: Klebsiella oxytoca

<400> SEQUENCE: 6
atgtatatcg ggattgatct cggcacctcg ggcgttaagg ccattctgct caacgagcag     60
ggcgaggtcg tggcttcgca caccgaaaag ctcaacgtgt cgcgtccgca ccctttatgg    120
tctgaacaag atcctgagca ctggtggctg cgacggacc gcgcgatgaa agcgttgggc    180
gcgcagcact ctttgcgcgc ggttaaagcg ttgggcattg cgggtcagat gcacggcgcg    240
acgctgctcg ataagcaaca gcgcgtcttg cgcccgcgca tcttgtggaa tgatggccgc    300
tgcggcgagg agtgtgcgct gctggaggag gaagtcagcc gttcgcgaca gatcaccggt    360
aatctgatga tgccgggatt taccgcgccg aagctgttgt gggtgcaacg tcacgagcct    420 gagatttta ggcaagtcga taaggttctg ctgccaaaag attatttacg tttgcgtatg    480
accggtgagt ttgccagcga tatgtccgat gccgccggaa cgatgtggat ggacgtggcg    540
cgccgcgact ggagcgatga aatgctcgcc gcctgtgggt tgagccgcga taacatgcca    600
gcgcttttcg aaggatgcga agtgacgggc tcgctgcgtc cggccgtcgc gcaagcgtgg    660
aatatgccgg aagtattggt ggtggccggc ggcggcgaca acgggcggg agcggttggc    720 gtaggtatgg cggatgcggg ccaggcgatg ctgtcgctgg ggacctcggg cgtctacttt    780
gccgtcagcg acggctttct tagcaaaccg gaaagcgccg ttcacagctt ctgccacgcg    840
ttgcctggac gctggcatct gatgtcggtc atgctgagcg cggcttcctg ccttgattgg    900
gcggcgacat taactggcct gggcacggtt ccggcgctga ttgcggcagc ggaagcggcg    960
aacgacgatg ccgatccggt ctggttcttg ccttatctct cgggtgaacg cacgccgcac   1020
```

| | |
|---|---|
| aacaatccgc aggcgaaagg cgtctttttc ggcctgactc atcaacacgg tccggcggag | 1080 |
| ctggcgcggg cggtgctgga gggagttggt tatgctctgg cggacggcat ggatgtggtt | 1140 |
| cacgcctgcg gcgtcaaacc ggagagcgtc acgctgattg gcggcggcgc gcgcagcgcc | 1200 |
| tactggcgga aaatgctggc ggatataagc ggccagcagc ttgatttccg caccggcggc | 1260 |
| gatgtcggac cggcgcttgg cgcggcgcgg ctggcgcagc tggcgctgca tcgaaatgtc | 1320 |
| gcgttttccg atctgctccc gcagctcccg ctggaacagg ctcatcttcc ggatgccgaa | 1380 |
| cgctttgcgc gttacgcacc tcgtagggaa actttccgcc agatttatca gcagctttta | 1440 |
| ccgctgatgt cctga | 1455 |

<210> SEQ ID NO 7
<211> LENGTH: 678
<212> TYPE: DNA
<213> ORGANISM: Klebsiella oxytoca

<400> SEQUENCE: 7

| | |
|---|---|
| atgaagcagt atttgattgc cccttcgatt ctgtcggctg attttgcccg tctgggcgag | 60 |
| gacaccgcca atgcgttggc tgcgggtgcg gatgttgtgc actttgacgt gatggacaac | 120 |
| cactacgtgc cgaatctgac cattggcccg atggtgctga aatcactgcg aaattacggt | 180 |
| atcactgcgc cgattgacgt gcatttgatg gtcaagccgg ttgaccgcat cgtccctgat | 240 |
| tttgccgccg cgggcgccag catcattact ttccatccgg aagcttccga acacgttgac | 300 |
| cgcacgctgc agcttatcaa agagcacggc tgcaaagccg gtttggtgtt taacccggcg | 360 |
| acctccctga gctaccttga ttacgtaatg gataagctgg atgttattct gctgatgtcc | 420 |
| gtcaaccctg gctttggcgg tcagtctttt attccgcaca ccctggaaaa actgcgtgaa | 480 |
| gttcgtcgtc gcattgatga atccggctac gacatccgtc tggaagtcga cggcggcgta | 540 |
| aaagtcagca atatcgctga gattgccgcc gccggtgcgg atatgttgt tgctgggtcg | 600 |
| gccattttcg atcagcctga ctacaaaaaa gtggtcgatc aaatgcgcag cgaattagca | 660 |
| aaggttagcc atggataa | 678 |

<210> SEQ ID NO 8
<211> LENGTH: 678
<212> TYPE: DNA
<213> ORGANISM: Klebsiella oxytoca

<400> SEQUENCE: 8

| | |
|---|---|
| atgaagcagt atttgattgc cccttcgatt ctgtcggctg attttgcccg tctgggcgag | 60 |
| gacaccgcca atgcgttggc tgcgggtgcg gatgttgtgc actttgacgt gatggacaac | 120 |
| cactacgtgc cgaatctgac cattggcccg atggtgctga aatcactgcg aaattacggt | 180 |
| atcactgcgc cgattgacgt gcatttgatg gtcaagccgg ttgaccgcat cgtccctgat | 240 |
| tttgccgccg cgggcgccag catcattact ttccatccgg aagcttccga acacgttgac | 300 |
| cgcacgctgc agcttatcaa agagcacggc tgcaaagccg gtttggtgtt taacccggcg | 360 |
| acctccctga gctaccttga ttacgtaatg gataagctgg atgttattct gctgatgtcc | 420 |
| gtcaaccctg gctttggcgg tcagtctttt attccgcaca ccctggaaaa actgcgtgaa | 480 |
| gttcgtcgtc gcattgatga atccggctac gacatccgtc tggaagtcga cggcggcgta | 540 |
| aaagtcagca atatcgctga gattgccgcc gccggtgcgg atatgttgt tgctgggtcg | 600 |
| gccattttcg atcagcctga ctacaaaaaa gtggtcgatc aaatgcgcag cgaattagca | 660 |
| aaggttagcc atggataa | 678 |

<210> SEQ ID NO 9
<211> LENGTH: 954
<212> TYPE: DNA
<213> ORGANISM: Klebsiella oxytoca

<400> SEQUENCE: 9

| | | | | | |
|---|---|---|---|---|---|
| atgacggata | aattgacctc | tctgcgtcag | tacaccactg | tcgtagctga | taccggagat | 60 |
| atcgcggcaa | tgaagctgta | tcagcctcag | gacgccacga | ctaacccttc | tttgattctc | 120 |
| ggcgcggctc | agatccctga | gtaccgtaag | ctgatcgatg | acgctgttgc | ctgggctcgc | 180 |
| ggccagagca | gcgaccgcgc | gcagcagatt | atcgatgctt | ccgataagct | ggcggtgaac | 240 |
| attggtcttg | aaatccttaa | gctgatccct | ggccgtattt | ccaccgaagt | cgatgctcgc | 300 |
| ctgtcctatg | acaccgaggc | atctatcgcc | aaagctaagc | gccttatcaa | gctgtacaac | 360 |
| gatgccggca | tcggcaacga | tcgcattctg | atcaaactgg | cttcgacctg | cagggcatc | 420 |
| cgcgccgctg | agcagctgga | aaagaaggc | atcaactgca | acctgacgct | gctgttctcc | 480 |
| ttcgctcagg | cacgtgcctg | cgccgaagcg | ggcgtattcc | tgatttctcc | gttcgttggc | 540 |
| cgtatcctcg | actggtacaa | agccaatacc | gataagaaag | agtacgcgcc | ggcagaagat | 600 |
| ccgggcgtgg | tttcggtaag | cgaaatctac | gaatactaca | acagcacgg | ctacgagacg | 660 |
| gtggttatgg | gcgcaagctt | ccgtaacctc | ggcgagatcc | tggagctggc | tggctgtgac | 720 |
| cgcctgacta | tcgctccggc | cctgctgaaa | gagctggcgg | aaagcgaagg | cgctatcgag | 780 |
| cgtaaactgg | cctttagcgg | cgaagttaaa | gcgcgtccgg | ctcgtatcac | cgaatccgag | 840 |
| ttcctgtggc | agcacaacca | ggatccgatg | gcggtagaca | aactggcgga | aggtatccgc | 900 |
| aagtttgcga | tcgaccagga | aaaactggaa | aaaatgatcg | gcgatctgct | gtaa | 954 |

<210> SEQ ID NO 10
<211> LENGTH: 1992
<212> TYPE: DNA
<213> ORGANISM: Klebsiella oxytoca

<400> SEQUENCE: 10

| | | | | | |
|---|---|---|---|---|---|
| atgtcctcac | gtaaagagct | tgctaacgct | attcgtgcgc | tgagcatgga | cgcagtacag | 60 |
| aaagccaaat | ccggtcaccc | gggtgccccg | atgggtatgg | ctgacattgc | cgaagtcctg | 120 |
| tggcgtgatt | tcctgaatca | taacccgcag | aacccgtcct | gggccgaccg | cgaccgtttt | 180 |
| gtcctgtcca | acggccacgg | ttccatgctg | atttacagct | tgctgcacct | caccggttat | 240 |
| gatctgccga | ttgaagagct | gaagaacttc | cgtcagctgc | actctaaaac | gccgggtcac | 300 |
| ccggaagtcg | gctacaccgc | gggcgtggaa | accactaccg | gtccgctggg | cagggtatt | 360 |
| gcgaatgcgg | ttggtatggc | catcgcggag | aaaactctgg | cggcgcagtt | caaccgcccg | 420 |
| ggccacgaca | ttgttgacca | cttcacctac | gcgttcatgg | gcgacggctg | catgatggaa | 480 |
| ggtatctctc | acgaggtatg | ctccctgccc | ggtaccctga | gcttggcaa | gctggtggcg | 540 |
| ttctatgacg | acaacggcat | ctctatcgac | ggtcatgtag | aaggttggtt | caccgatgac | 600 |
| accgcgaagc | gttttgaagc | ctacggctgg | cacgtggtgc | gcggcgttga | cggccacgat | 660 |
| gctgactcga | ttaaacgcgc | ggtagaagaa | gcgcgtgcgg | tcaccgacaa | accgtccctg | 720 |
| ctgatgtgca | aaaccattat | tggtttcggt | tcgccgaaca | agccggtac | ccacgactcc | 780 |
| cacgcgcgc | cgctgggcga | cgcggaaatc | gcgctgaccc | gcgaagcgct | cggctggaaa | 840 |
| cacccggcat | ttgaaatccc | gtctgaaatc | tatgcccagt | gggatgccaa | agaagccggc | 900 |

```
caggcgaaag agtccgcgtg gaacgagaaa tttgccgcct acgccaaagc cttcccgcag    960
gaagccgccg agtttactcg tcgtatgaaa ggcgacatgc cggctgactt cgatgcgaaa   1020
gcgaacgagt tcatcgcgaa gctgcaggct aacccggcga aaatcgccag ccgtaaagca   1080
tctcagaacg ccattgaagc cttcggcccg ctgctgcctg agttccttgg cggttccgct   1140
gacctggcgc aagtaaccct gaccctgtgg tccggttcta aagcgatcaa cgaagacact   1200
gccggtaact acatccacta cggcgtgcgc gaattcggta tgaccgcgat tgccaacggt   1260
atcgctctgc acggcggttt cctgccgtac acctctacct tcctgatgtt cgtcgagtat   1320
gcgcgtaacg cggtacgtat ggccgcgctg atgaaacagc gtcaggtaat ggtctacacc   1380
cacgactcca tcggtctggg cgaagacggc ccgactcacc agccggtaga gcaggtggct   1440
tccctgcgcg tcacgccgaa catgtccaca tggcgtccgt gcgaccaggt ggaatccgcc   1500
atcgcgtgga aatatggcgt tgagcgtcag gacggcccga ccgcgctgat tctgtcccgt   1560
cagaacctgg cgcagcagga gcgtactgaa gagcagctgg cgaacgttgc ccgcggcggc   1620
tacgtgctga aggattgtgc cggtcagccg gaactgatct catcgccac cggctctgaa   1680
gttgagctgg cggttgccgc ttacgaaaaa ttgactgccg aaggcgtgaa ggcgcgcgtg   1740
gtttccatgc cgtccaccga cgcgttcgac aagcaggatg ccgcttaccg tgaagccgtg   1800
ctgccgaaag ccgtctctgc gcgcgtagct atcgaagcgg tatcgccga ctactggttc   1860
aaatacgtgg gcctgaacgg cgcgatcgtt ggcatgacca ctttcggtga gtctgcgccg   1920
gcggagctgc tgtttgaaga gtttggcttc accgtggata acgttgtcgc caaagcgaaa   1980
gcactgctgt ag                                                      1992

<210> SEQ ID NO 11
<211> LENGTH: 1995
<212> TYPE: DNA
<213> ORGANISM: Klebsiella oxytoca

<400> SEQUENCE: 11
atgtcccgta gagaactcgc taacgccatc cgcgccctga gtatggatgc agtccagaaa    60
gccaactccg ccaccccgg cgcgccgatg ggcatggccg atatcgcaga ggtgctgtgg   120
aacgatttcc ttaagcacaa tcctgaaaac ccgcaatggt acgatcgcga ccgctttatt   180
ctctccaacg gccacgcgtc gatgctgctc tacagcctgc tgcatctgac gggctatgac   240
ttgcccatcg aagagataaa aaacttccgt cagttgcatt ccaaaacgcc ggggcacccg   300
gaaatcggct ataccccggg ggttgaaacc accaccgggc cgctggggca gggctggcg   360
aacgcggtgg ggctggctat cgccgagcgt acgctggcgg cgcagtttaa tcagccagac   420
catgagatcg tcgatcactt tacctacgtg tttatgggcg atggctgtct gatggagggg   480
atttctcacg aagtctgctc tctggcgggt acgttaggac tgggtaagct catcggcttc   540
tacgaccaca acggtatttc cattgatggc gaaaccaaag ctggtttac cgatgacacg   600
gcaaaacgct tcgaggccta tcactggcat gtggttcatg aaattgacgg ccacgatccc   660
gaagccgtga agaaagcgat tctggaagcc cagagcgtga aggataaacc ttcgctgatt   720
atctgccgta cggtaatagg ttttggttca ccgaataaag ccgggaaaga agaggcccac   780
ggcgccgcgc tgggcgaaca ggaagtggcg ctggcgcgcc agcagctggg ctggcatcat   840
ccggcgtttg agatcccgaa agagatctac cgcgccctgg gacgcgcgtga aagggacaa   900
aaagcgcaga aaagctggga ggagaagttt gccgcctatc agcaggtcca tcctcagctg   960
gcagctgagt ttacgcggcg catgagcggc ggactgcctg agtcgtggga tgaaacaacg  1020
```

-continued

```
cggaaatata tcgctgagct gcaggccaac ccggcgaaaa tcgccacgcg taaggcttcg   1080
caaaacgccc ttgatgccta cggcccgcat ctaccagaac tgttgggcgg ctccgctgac   1140
ctcgcgccaa gtaacctgac tatctggaaa ggttcgactt cgctgaaaga agatccggcg   1200
ggcaactata ttcactacgg cgtacgtgaa ttcgggatga cggccatcgc caacggcatc   1260
gcccaccacg gcgggtttct accttatact gccaccttcc tgatgttcgt cgaatatgcc   1320
cgcaacgcgg cgcgtatggc ggcgttgatg aaagcgcggc aaatcatggt ctatacccac   1380
gactccatcg gtctcggcga agatggtccg acgcaccagg cggtagaaca gctggccagc   1440 ctgccgcctga cgccaaactt cagcacctgg cgaccatgcg atcaggtcga ggccgcggtg   1500
gcgtggaaac tggcggtaga gcgtcatagc gggccgacgg cgctaattct ctcaaggcaa   1560
aatctggcac aaatggcgcg cacgccggaa caggtacaga atatcgcccg cggcggctac   1620
gtactgaagg acgccggcgg caagccggac ctgatcctga tagccaccgg ttcagaggtc   1680
gagatcaccg tactggccgc agaaaagctg ctggccaaag gggtgaacgt gcgcgtggtc   1740
tccctgccat cgaccgacgt atttgatgcc caggatgaag cctatcggga gtccgtactg   1800
ccatcagacg tcagcgcccg cgttgccgtg gaggcaggga tcgccgacta ctggtataaa   1860
tatgtgggac tcaaaggaaa aattgtcggt atgaccggct acggtgaatc ggccccggcc   1920
gataaacttt tcccttactt cggcttcacc gttgagcata tcgtcaacgt aggggacgag   1980
gtacagaacg ggtaa                                                   1995

<210> SEQ ID NO 12
<211> LENGTH: 3987
<212> TYPE: DNA
<213> ORGANISM: Klebsiella oxytoca

<400> SEQUENCE: 12
atgtcctcac gtaaagagct tgctaacgct attcgtgcgc tgagcatgga cgcagtacag     60
aaagccaaat ccggtcaccc gggtgccccg atgggtatgg ctgacattgc cgaagtcctg    120
tggcgtgatt tcctgaatca taacccgcag aacccgtcct gggccgaccg cgaccgtttt    180
gtcctgtcca acgccacgg ttccatgctg atttacagct tgctgcacct caccggttat    240
gatctgccga ttgaagagct gaagaacttc cgtcagctgc actctaaaac gccgggtcac    300
ccggaagtcg gctacaccgc gggcgtggaa accactaccg gtccgctggg gcagggtatt    360
gcgaatgcgg ttggtatggc catcgcggag aaaactctgg cggcgcagtt caaccgcccg    420
ggccacgaca ttgttgacca cttcacctac gcgttcatgg gcgacggctg catgatggaa    480
ggtatctctc acgaggtatg ctccctggcc ggtaccctga gcttggcaa gctggtggcg    540 ttctatgacg acaacggcat ctctatcgac ggtcatgtag aaggttggtt caccgatgac    600
accgcgaagc gttttgaagc ctacggctgg cacgtggtgc gcggcgttga cggccacgat    660
gctgactcga ttaaacgcgc ggtagaagaa gcgcgtgcgg tcaccgacaa accgtccctg    720
ctgatgtgca aaaccattat tggtttcggt tcgccgaaca aagccggtac ccacgactcc    780
cacggcgcgc cgctgggcga cgcggaaatc gcgctgaccc gcgaagcgct cggctggaaa    840
cacccggcat ttgaaatccc gtctgaaatc tatgcccagt gggatgccaa agaagccggc    900
caggcgaaag agtccgcgtg gaacgagaaa tttgccgcct acgccaaagc cttcccgcag    960
gaagccgccg agtttactcg tcgtatgaaa ggcgacatgc cggctgactt cgatgcgaaa   1020
gcgaacgagt tcatcgcgaa gctgcaggct aacccggcga aaatcgccag ccgtaaagca   1080
```

```
tctcagaacg ccattgaagc cttcggcccg ctgctgcctg agttccttgg cggttccgct      1140
gacctggcgc caagtaacct gaccctgtgg tccggttcta aagcgatcaa cgaagacact      1200
gccggtaact acatccacta cggcgtgcgc gaattcggta tgaccgcgat tgccaacggt      1260
atcgctctgc acggcggttt cctgccgtac acctctacct tcctgatgtt cgtcgagtat      1320
gcgcgtaacg cggtacgtat ggccgcgctg atgaaacagc gtcaggtaat ggtctacacc      1380
cacgactcca tcggtctggg cgaagacggc ccgactcacc agccggtaga gcaggtggct      1440
tccctgcgcg tcacgccgaa catgtccaca tggcgtccgt gcgaccaggt ggaatccgcc      1500
atcgcgtgga atatggcgt tgagcgtcag gacggcccga ccgcgctgat tctgtcccgt       1560
cagaacctgg cgcagcagga gcgtactgaa gagcagctgg cgaacgttgc ccgcggcggc      1620
tacgtgctga aggattgtgc cggtcagccg gaactgatct tcatcgccac cggctctgaa      1680
gttgagctgg cggttgccgc ttacgaaaaa ttgactgccg aaggcgtgaa ggcgcgcgtg      1740
gtttccatgc cgtccaccga cgcgttcgac aagcaggatg ccgcttaccg tgaagccgtg      1800
ctgccgaaag ccgtctctgc gcgcgtagct atcgaagcgg gtatcgccga ctactggttc      1860
aaatacgtgg gcctgaacgg cgcgatcgtt ggcatgacca cttcggtga gtctgcgccg      1920 gcggagctgc tgtttgaaga gtttggcttc accgtgata acgttgtcgc caaagcgaaa      1980
gcactgctgt agatgtcccg tagagaactc gctaacgcca tccgcgccct gagtatggat      2040
gcagtccaga aagccaactc cggccacccc ggcgcgccga tgggcatggc cgatatcgca      2100
gaggtgctgt ggaacgattt ccttaagcac aatcctgaaa accgcaatg gtacgatcgc       2160 gaccgcttta ttctctccaa cggccacgcg tcgatgctgc tctacagcct gctgcatctg      2220
acgggctatg acttgcccat cgaagagata aaaaacttcc gtcagttgca ttccaaaacg      2280
ccggggcacc cggaaatcgg ctataccccg ggggttgaaa ccaccaccgg gccgctgggg      2340
caagggctgg cgaacgcggt ggggctggct atcgccgagc gtacgctggc ggcgcagttt      2400
aatcagccag accatgagat cgtcgatcac tttacctacg tgtttatggg cgatggctgt      2460
ctgatggagg ggatttctca cgaagtctgc tctctggcgg gtacgttagg actgggtaag      2520
ctcatcggct tctacgacca caacggtatt tccattgatg gcgaaaccaa aggctggttt      2580
accgatgaca cggcaaaacg cttcgaggcc tatcactggc atgtggttca tgaaattgac      2640
ggccacgatc ccgaagccgt gaagaaagcg attctggaag cccagagcgt gaaggataaa      2700
ccttcgctga ttatctgccg tacggtaata ggttttggtt caccgaataa agccgggaaa      2760
gaagaggccc acgcgccgc gctgggcgaa caggaagtgg cgctggcgcg ccagcagctg       2820
ggctggcatc atccggcgtt tgagatcccg aaagagatct accgcgcctg ggacgcgcgt      2880
gaaaagggac aaaagcgca gaaagctgg gaggagaagt tgccgcccta tcagcaggtc       2940
catcctcagc tggcagctga gtttacgcgg cgcatgagcg gcggactgcc tgagtcgtgg      3000
gatgaaacaa cgcggaaata tatcgctgag ctgcaggcca acccggcgaa atcgccacg       3060 cgtaaggctt cgcaaaacgc ccttgatgcc tacggcccgc atctaccaga actgttgggc      3120
ggctccgctg acctcgcgcc aagtaacctg actatctgga aaggttcgac ttcgctgaaa      3180
gaagatccgg cggcaactaa tattcactac ggcgtacgtg aattcgggat gacgccatc       3240 gccaacggca tcgcccacca cggcgggttt ctaccttata ctgccacctt cctgatgttc      3300
gtcgaatatg cccgcaacgc ggcgcgtatg gcggcgttga tgaaagcgcg gcaaatcatg      3360
gtctataccc acgactccat cggtctcggc gaagatggtc cgacgcacca ggcggtagaa      3420
cagctggcca gcctgcgcct gacgccaaac ttcagcacct ggcgaccatg cgatcaggtc      3480
```

```
gaggccgcgg tggcgtggaa actggcggta gagcgtcata gcgggccgac ggcgctaatt    3540
ctctcaaggc aaaatctggc acaaatggcg cgcacgccgg aacaggtaca gaatatcgcc    3600
cgcggcggct acgtactgaa ggacgccggc ggcaagccgg acctgatcct gatagccacc    3660
ggttcagagg tcgagatcac cgtactggcc gcagaaaagc tgctggccaa aggggtgaac    3720
gtgcgcgtgg tctccctgcc atcgaccgac gtatttgatg cccaggatga agcctatcgg    3780
gagtccgtac tgccatcaga cgtcagcgcc cgcgttgccg tggaggcagg gatcgccgac    3840
tactggtata aatatgtggg actcaaagga aaaattgtcg gtatgaccgg ctacggtgaa    3900 tcggcccegg ccgataaact tttcccttac ttcggcttca ccgttgagca tatcgtcaac    3960
gtaggggacg aggtacagaa cgggtaa                                        3987

<210> SEQ ID NO 13
<211> LENGTH: 633
<212> TYPE: DNA
<213> ORGANISM: Klebsiella oxytoca

<400> SEQUENCE: 13
atggtgcttg gcaaaccgca aacagaccct acccttgaat ggttcttgtc tcattgccac      60
attcataagt acccatcaaa gagcacgctg atccaccagg gtgagaaagc agaaacgttg     120
tactacatcg ttaaaggctc cgtggctgta ctcatcaagg atgaagaagg taagagatg      180 atcctctctt acctcaatca gggcgatttc atcggtaat taggcttgtt tgaagaaggc     240
caggagcgta gcgcttgggt acgtgcgaaa accgcatgtg aagtggccga aatctcctac     300
aaaaaattcc gtcagctgat ccaggttaac ccggacctcc tgatgcgtct ctcttcgcag     360
atggctcgtc gtctgcaggt catctctgag aaagtgggta acctcgcctt cctcgacgtt     420
accggtcgta tcacccagac gctgctgaac ctggctaaac agccggatgc gatgacccac     480
ccggacggta tgcaaattaa aattacccgc caggaaatcg gtcagatcgt cggatgctcc     540
cgcgagaccg ttggccgtat cctgaaaatg ctggaagatc aaaacctgat ctccgcgcac     600
ggtaaaacta tcgtcgtcta cggtacccgt taa                                   633

<210> SEQ ID NO 14
<211> LENGTH: 633
<212> TYPE: DNA
<213> ORGANISM: Klebsiella oxytoca

<400> SEQUENCE: 14
atggtgcttg gcaaaccgca aacagaccct acccttgaat ggttcttgtc tcattgccac      60
attcataagt acccatcaaa gagcacgctg atccaccagg gtgagaaagc agaaacgttg     120
tactacatcg ttaaaggctc cgtggctgta ctcatcaagg atgaagaagg taagagatg      180 atcctctctt acctcaatca gggcgatttc atcggtgcat taggcttgtt tgaagaaggc     240
caggagcgta gcgcttgggt acgtgcgaaa accgcatgtg aagtggccga aatctcctac     300
aaaaaattcc gtcagctgat ccaggttaac ccggacatcc tgatgcgtct ctcttcgcag     360
atggctcgtc gtctgcaggt cacgtctgag aaagtgggta acctcgcctt cctcgacgtt     420
accggtcgta tcacccagac gctgctgaac ctggctaaac agccggatgc gatgacccac     480
ccggacggta tgcaaattaa aattacccgc caggaaatcg gtcagatcgt cggatgctcc     540
cgcgagaccg ttggccgtat cctgaaaatg ctggaagatc aaaacctgat ctccgcgcac     600
ggtaaaacta tcgtcgtcta cggtacccgt taa                                   633
```